(12) United States Patent
Kadi et al.

(10) Patent No.: US 10,570,379 B2
(45) Date of Patent: Feb. 25, 2020

(54) POLYPEPTIDES FOR CARBON-CARBON BOND FORMATION AND USES THEREOF

(71) Applicant: INVISTA North America S.à.r.l., Wilmington, DE (US)

(72) Inventors: Nadia Kadi, Middlesbrough (GB); Adriana Leonora Botes, Rosedale East (GB)

(73) Assignee: INVISTA North America S.a.r.l., Wilmington, DE (US)

( * ) Notice: Subject to any disclaimer, the term of this patent is extended or adjusted under 35 U.S.C. 154(b) by 0 days.

(21) Appl. No.: 15/349,303

(22) Filed: Nov. 11, 2016

(65) Prior Publication Data

US 2017/0159031 A1   Jun. 8, 2017

Related U.S. Application Data

(60) Provisional application No. 62/255,276, filed on Nov. 13, 2015.

(51) Int. Cl.
| | |
|---|---|
| *C12P 7/16* | (2006.01) |
| *C12P 5/02* | (2006.01) |
| *C12P 7/42* | (2006.01) |
| *C12N 9/04* | (2006.01) |
| *C12N 9/10* | (2006.01) |
| *C12P 11/00* | (2006.01) |
| *C12P 7/40* | (2006.01) |
| *C12P 7/04* | (2006.01) |
| *C12P 7/26* | (2006.01) |
| *C12P 19/32* | (2006.01) |

(52) U.S. Cl.
CPC ............ *C12N 9/1029* (2013.01); *C12N 9/13* (2013.01); *C12P 5/026* (2013.01); *C12P 7/04* (2013.01); *C12P 7/26* (2013.01); *C12P 7/40* (2013.01); *C12P 11/00* (2013.01); *C12P 19/32* (2013.01); *C12Y 101/01* (2013.01); *C12Y 101/01001* (2013.01); *C12Y 203/01016* (2013.01); *C12Y 208/03* (2013.01); *C12Y 401/01* (2013.01); *C12Y 402/01* (2013.01); *Y02E 50/343* (2013.01)

(58) Field of Classification Search
CPC . C12N 9/88; C12N 9/1025; C12P 7/44; C12P 7/04; C12P 7/62; C12Y 101/01035; C12Y 402/01
USPC .................. 435/252.33, 254.2, 135, 142, 146
See application file for complete search history.

(56) References Cited

U.S. PATENT DOCUMENTS

| | | |
|---|---|---|
| 9,422,578 B2 | 8/2016 | Pearlman et al. |
| 9,422,580 B2 | 8/2016 | Pearlman et al. |
| 2009/0226989 A1 | 9/2009 | Suominen et al. |
| 2013/0109064 A1* | 5/2013 | Osterhout ............... C12P 7/18 435/135 |
| 2014/0296571 A1* | 10/2014 | Green et al. |
| 2015/0064759 A1* | 3/2015 | Perez et al. |
| 2016/0138052 A1* | 5/2016 | Mordaka ............... C12P 19/30 435/89 |

FOREIGN PATENT DOCUMENTS

| | | | |
|---|---|---|---|
| JP | 2012-235729 | A | 12/2012 |
| KR | 10-2008-0028902 | A | 4/2008 |
| KR | 10-2014-0001165 | A | 1/2014 |
| WO | 2014/047407 | A1 | 3/2014 |
| WO | 2015/017404 | A1 | 2/2015 |
| WO | 2015/031653 | A2 | 3/2015 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Becker et al., "Metabolic Flux Engineering of I-lysine Production in Corynebacterium Glutamicum—Over Expression and Modification of G6P Dehydrogenase", Journal of Biotechnology, vol. 132, Oct. 31, 2007, pp. 99-109.
Beld et al., "The Phosphopantetheinyl Transferases: Catalysis of a Posttranslational Modification Crucial for Life", Nat Prod Rep., vol. 31, No. 1, Jan. 2014, pp. 61-108.
Brigham et al., "Engineering Ralstonia Eutropha for Production of Isobutanol from CO2, H2, and O2", Advanced Biofuels and Bioproducts, Chapter 39, Jan. 2013, pp. 1065-1090.
Bugg et al., "The Emerging Role for Bacteria in Lignin Degradation and Bio-product Formation", Current Opinion in Biotechnology, vol. 22, 2011, pp. 394-400.
Cintolesi et al., "In Silico Assessment of the Metabolic Capabilities of an Engineered Functional Reversal of the B-Oxidation Cycle for the Synthesis of Longer-Chain (C≥4) Products", Metabolic Engineering, vol. 23, May 2014, pp. 100-115.
Clomburg et al., "Integrated Engineering of Beta-Oxidation Reversal and Omega-Oxidation Pathways for the Synthesis of Medium Chain Omega-Functionalized Carboxylic Acids", Metabolic Engineering, vol. 28, Mar. 2015, pp. 202-212.
Davis et al., "Biosynthetic Thiolase from Zoogloea Ramigera. II. Inactivation with Haloacetyl CoA Analogs", The Journal of Biological Chemistry, vol. 262, No. 1, Jan. 5, 1987, pp. 90-96.
Dellomonaco et al., "Engineered Reversal of the β-Oxidation Cycle for the Synthesis of Fuels and Chemicals", Nature, vol. 476, Aug. 18, 2011, pp. 355-359.
Hermann, Thomas, "Industrial Production of Amino Acids by Coryneform Bacteria", Journal of Biotechnology, vol. 104, 2003, pp. 155-172.

(Continued)

*Primary Examiner* — Robert B Mondesi
*Assistant Examiner* — Mohammad Y Meah
(74) *Attorney, Agent, or Firm* — Invista North America S.A.R.L.

(57) ABSTRACT

This document describes polypeptides with dual CoA transferase and β-ketothiolase activities and variants thereof, use of such polypeptides in biosynthetic methods, and non-naturally occurring hosts comprising such polypeptides.

8 Claims, 16 Drawing Sheets

Specification includes a Sequence Listing.

(56) References Cited

OTHER PUBLICATIONS

Hou et al., "Haloarchaeal-Type β-Ketothiolases Involved in Poly (3-Hydroxybutyrate-co-3-Hydroxyvalerate) Synthesis in Haloferax Mediterranei", Applied and Environmental Microbiology, vol. 79, No. 17, Sep. 2013, pp. 5104-5111.

Janßen et al., "Fatty Acid Synthesis in Escherichia coli and its Applications Towards the Production of Fatty Acid Based Biofuels", Biotechnology for Biofuels, vol. 7, No. 7, 2014, 26 pages.

Jaremko et al., "The Initial Metabolic Conversion of Levulinic Acid in Cupriavidus Necator", Journal of Biotechnology, vol. 155, 2011, pp. 293-298.

Kim et al., "Crystal Structure and Biochemical Characterization of Beta-Keto Thiolase B from Polyhydroxyalkanoate-Producing Bacterium Ralstonia Eutropha H16", Biochemical and Biophysical Research Communications, vol. 444, No. 3, 2014, pp. 365-369.

Klein et al., "Heterologous Expression and Characterisation of a Biosynthetic Thiolase from Clostridium Butyricum DSM 10702", Enzyme and Microbial Technology, vol. 45, 2009, pp. 361-366.

Kopke et al., "2,3-Butanediol Production by Acetogenic Bacteria, an Alternative Route to Chemical Synthesis, Using Industrial Waste Gas", Applied and Environmental Microbiology, vol. 77, No. 15, Aug. 2011, pp. 5467-5475.

Lee et al., "Metabolic Engineering of Pentose Phosphate Pathway in Ralstoniaeutropha for Enhanced Biosynthesis of Poly-β-Hydroxybutyrate", Biotechnology Progress, vol. 19, Issue 5, 2003, pp. 1444-1449.

Lee et al., "Synthesis of Pure Meso-2,3-Butanediol from Crude Glycerol Using an Engineered Metabolic Pathway in Escherichia coli", Applied Biochemistry and Biotechnology, vol. 166, No. 7, 2012, pp. 1801-1813.

Li et al.,"Cupriavidus Necator JMP134 Rapidly Reduces Furfural with a Zn-Dependent Alcohol Dehydrogenase", Biodegradation, vol. 22, No. 6, 2011, pp. 1215-1225.

Lim et al., "Amplification of the NADPH-Related Genes zwf and gnd for the Oddball Biosynthesis of PHB in an E. coli Transformant Harboring a Cloned phbCAB Operon", Journal of Bioscience and Bioengineering, vol. 93, No. 6, 2002, pp. 543-549.

Martin et al., "High-Titer Production of Monomeric Hydroxyvalerates from Levulinic Acid in Pseudomonas Putida", Journal of Biotechnology, vol. 139, No. 1, 2009, pp. 61-67.

Meijnen et al., "Improved p-Hydroxybenzoate Production by Engineered Pseudomonas Putida S12 by Using a Mixed-Substrate Feeding Strategy", Applied Microbiology and Biotechnology, vol. 90, No. 3, 2011, pp. 885-893.

Modis et al., "A Biosynthetic Thiolase in Complex With a Reaction Intermediate: The Crystal Structure Provides New Insights Into the Catalytic Mechanism", Structure, vol. 7, Issue 10, 1999, pp. 1279-1290.

Ohashi et al., "Continuous Production of Lactic Acid from Molasses by Perfusion Culture of Lactococcus Lactis Using a Stirred Ceramic Membrane Reactor", Journal of Bioscience and Bioengineering, vol. 87, No. 5, 1999, pp. 647-654.

Palmer et al., "Biosynthetic Thiolase From Zoogloea Ramigera. Evidence for a Mechanism Involving Cys-378 as the Active Site Base", The Journal of Biological Chemistry, vol. 266, No. 13, 1991, pp. 8369-8375.

Papanikolaou et al., "Citric Acid Production by Yarrowia Lipolytica Cultivated on Olive-Mill Wastewater-Based Media", Bioresource Technology, vol. 99, No. 7, 2008, pp. 2419-2428.

Perez-Pantoja et al., "Metabolic Reconstruction of Aromatic Compounds Degradation from the Genome of the Amazing Pollutant-Degrading Bacterium Cupriavidus Necator JMP134", FEMS Microbiology Reviews, vol. 32, Aug. 7, 2008, pp. 736-794.

Przybylski et al., "Third-Generation Feed Stocks for the Clean and Sustainable Biotechnological Production of Bulk Chemicals: Synthesis of 2-Hydroxyisobutyric Acid", Energy, Sustainability and Society, vol. 2, No. 11, 2012, 9 pages.

Ramsay et al., "Use of a Nylon Manufacturing Waste as an Industrial Fermentation Substrate", Applied and Environmental Microbiology, vol. 52, No. 1, Jul. 1986, pp. 152-156.

Satoh et al., "Enzyme-Catalyzed Poly (3-hydroxybutyrate) Synthesis from Acetate with CoA Recycling and NADPH Regeneration in Vitro", Journal of Bioscience and Bioengineering, vol. 95, No. 4, 2003, pp. 335-341.

Seedorf et al., "The Genome of Clostridium Kluyveri, a Strict Anaerobe with Unique Metabolic Features", PNAS USA, vol. 105, No. 6, Feb. 12, 2008, pp. 2128-2133.

Selmer et al., Propionate CoA-Transferase from Clostridium Propionicum Cloning of the Gene and Identification of Glutamate 324 at the Active Site, Eur. J. Biochem, vol. 269, Jan. 2002, pp. 372-380.

Shen et al., "Driving Forces Enable High-Titer Anaerobic 1-Butanol Synthesis in Escherichia coli", Applied and Environmental Microbiology, vol. 77, No. 9, May 2011, pp. 2905-2915.

Sunbul et al., "Using Phosphopantetheinyl Transferases for Enzyme Posttranslational Activation, Site Specific Protein Labeling and Identification of Natural Product Biosynthetic Gene Clusters from Bacterial Genomes", Methods in Enzymology, vol. 458, Ch. 10, 2009, pp. 255-275.

Wee et al., "Biotechnological Production of Lactic Acid and Its Recent Applications", Food Technology and Biotechnology, vol. 44, No. 2, 2006, pp. 163-172.

Yang et al., "Value-Added Uses for Crude Glycerol—a Byproduct of Biodiesel Production", Biotechnology for Biofuels, vol. 5, No. 13, 2012, pp. 1-10.

Yu et al., "Production of Fatty Acid-Derived Valuable Chemicals in Synthetic Microbes", Frontiers in Bioengineering and Biotechnology, vol. 2, Article 78, Dec. 2014, pp. 1-12.

International Search Report and the Written Opinion in PCT US2016/061539 dated Mar. 20, 2017.

International Preliminary Report on Patentability in PCT US2016/061539 dated May 24, 2018.

Abdel-Rahman et al. (Apr. 24, 2013) "Recent advances in lactic acid production by microbial fermentation processes," Biotechnol. Adv. 31(6):877-902.

Dandi et al. (Nov. 21, 2012) "Bioprospecting of thermo- and osmo-tolerant fungi from mango pulp-peel compost for bioethanol production," Antonie Van Leeuwenhoek. 103(4):723-736.

Gallardo et al. (2011) "Enrichment of a continuous culture of Saccharomyces cerevisiae with the yeast Issatchenkia orientalis in the production of ethanol at increasing temperatures," J Ind Microbiol Biotechnol. 38 (3):405-414.

Kitagawa et al. (2010) "Construction of a β-glucosidase expression system using the multistress-tolerant yeast Issatchenkia orientalis," Appl. Microbiol. Biotechnol. 87(5):1841-1853.

Qiu et al. (1997) "The Escherichia coli polB locus is identical to dinA, the structural gene for DNA polymerase II Characterization of Pol II purified from a polB mutant," Journal of Biological Chemistry. 272:8611-8617.

Sauer et al. (2010) "16 years research on lactic acid production with yeast—ready for the market?" Biotechnol Genet Eng Rev. 27:229-256.

Toivari et al. (Feb. 7, 2013) "Low pH D-xylonate production with Pichia kudriavzevii," Bioresour. Technol. 133:555-562.

International Search Report with Written Opinion corresponding to International Patent Application No. PCT/KR2015/006314, dated Sep. 24, 2015.

\* cited by examiner

Fig. 1B
(i)
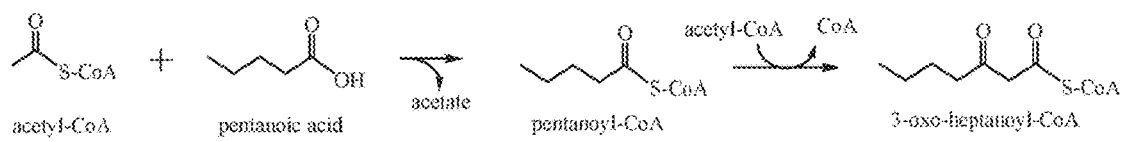
(ii)
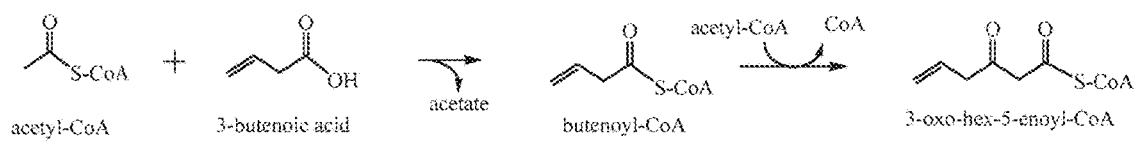
(iii)
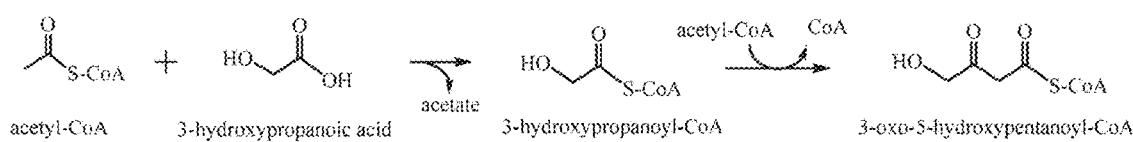
(iv)
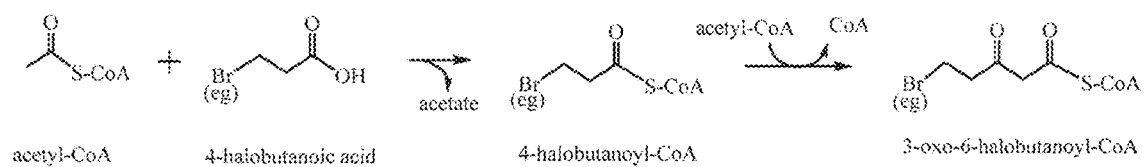

Fig. 1C
(i)
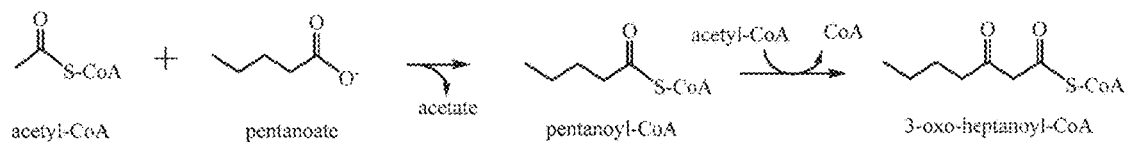
(ii)
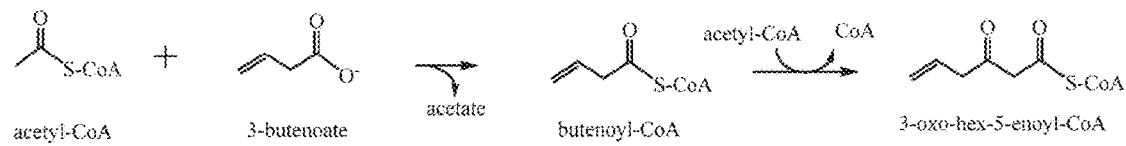
(iii)
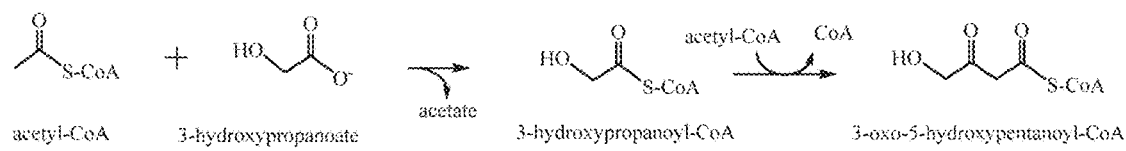
(iv)
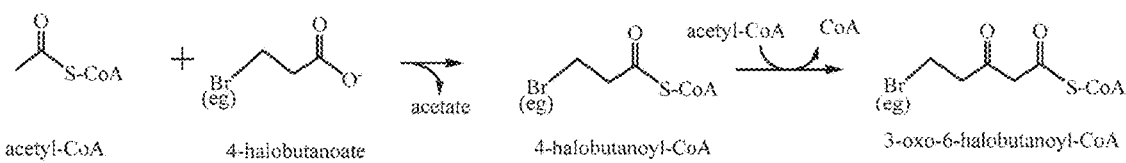

Fig. 2A

| SEQ ID NO | Source | Sequence |
|---|---|---|
| 1 | Clostridium propionicum, YdiF | MRKVPIITADEAAKLIKDGDTVTTSGFVGNAIPEALDRAVEKRFLETGEPKNITY VYCGSQGNRDGRGAEHFAHEGLLKRYIAGHWATVPALGKMAMENKMEAYNV SQGALCHLFRDIASHKPGVFTKVGIGTFIDPRNGGKVNDITKEDIVELVEIKGQ EYLFYPAFPIHVALIRGTYADESGNITFEKEVAPLEGTSVCQAVKNSGGIVVQ VERVVKAGTLDPRHVKVPGIYVDYVVVADPEDHQQSLDCEYDPALSGEHRRP EVVGEPLPLSAKKVIGRRGAIELEKDVAVNLGVGAPEYVASVADEEGIVDFMTL TAESGAIGGVPAGGVRFGASYNADALIDQGYQFDYDGGGLDLCYLGLAECD EKGNINVSRFGPRIAGCGGFINITQNTPKVFFCGTFTAGGLKVKIEDGKVIIVQE GKQKKFLKAVEQITFNGDVALANKQQVTYITERCVFLLKEDGLHLSEIAPGIDLQ TQILDVMDFAPIIDRDANGQIKLMDAALFAEGLMGLKEMKS |

Fig. 2B

| SEQ ID NO | Source | Sequence |
|---|---|---|
| 2 | Modified *Clostridium propionicum*, where 2 amino acids were added to the N-terminal sequence followed by 6xHis-tag, a linker 3 amino acids in length and a specific proteolytic cleavage site (thrombin site, underlined) | MGHHHHHHSSGLVPRGSMRKVPIITADEAAKLIKDGDTVTTSGFVGNAIPEAL DRAVEKRFLETGEPKNITYVYCGSQGNRDGRGAEHFAHEGLLKRYIAGHWAT VPALGKMAMENKMEAYNVSQGALCHLFRDIASHKPGVFTKVGIGTFIDPRNG GGKVNDITKEDIVELVEIKGQEYLFYPAFPIHVALIRGTYADESGNITFEKEVAPL EGTSVCQAVKNSGGIVVVQVERVVKAGTLDPRHVKVPGIYVDYVVADPEDH QQSLDCEYDPALSGEHRRPEVVGEPLPLSAKKVIGRGAIELEKDVAVNLGVG APEYVASVADEEGIVDFMTLTAESGAIGGVPAGGVRFGASYNADALIDQGYQF DYYDGGGLDLCYLGLAECDEKGNINVSRFGPRIAGCGGFINITQNTPKVFFCG TFTAGGLKVKIEDGKVIIVQEGKQKKFLKAVEQITFNGDVALANKQQVTYITERC VFLLKEDGLHLSEIAPGIDLQTQILDVMDFAPIIDRDANGQIKLMDAALFAEGLM GLKEMKS |

Fig. 2C

| SEQ ID NO | Source | Sequence |
|---|---|---|
| 3 | YdiF mutant E324G (numbering as based on SEQ ID NO: 1, position 324 underlined) | MGHHHHHHSSGLVPRGSMRKVPIITADEAAKLIKDGTVTTSGFVGNAIPEAL DRAVEKRFLETGEPKNITYVVCGSQGNRDGRGAEHFAHEGLLKRYIAGHWAT VPALGKMAMENKMEAYNVSQGALCHLFRDIASHKPGVFTKVGIGTFIDPRNG GGKVNDITKEDIVELVEIKGQEYLFYPAFPIHVALIRGTYADESGNITFEKEVAPL EGTSVCQAVKNSGGIVVVQVERVVKAGTLDPRHVKVPGIYVDYVVADPEDH QQSLDCEYDPALSGEHRRPEVVGEPLPLSAKKVIGRRGAIELEKDVAVNLGVG APEYVASVADEEGIVDFMTLTAGSGAIGGVPAGGVRFGASYNADALIDQGYQF DYYDGGGLDLCYLGLAE<u>G</u>DEKGNINVSRFGPRIAGCGGFINITQNTPKVFFCG TFTAGGLKVKIEDGKVIIVQEGKQKKFLKAVEQITFNGDVALANKQQVTYITERC VFLLKEDGLHLSEIAPGIDLQTQILDVMDFAPIIDRDANGQIKLMDAALFAEGLM GLKEMKS |

Fig. 2D

| SEQ ID NO | Source | Sequence |
|---|---|---|
| 4 | YdiF mutant E324L (numbering as based on SEQ ID NO: 1, position 324 underlined) | MGHHHHHHSSGLVPRGSMRKVPITADEAAKLIKDGDTVTTSGFVGNAIPEAL DRAVEKRFLETGEPKNITYVYCGSQGNRDGRGAEHFAHEGLLKRYIAGHWAT VPALGKMAMENKMEAYNVSQGALCHLFRDIASHKPGVFTKVGIGTFIDPRNG GGKVNDITKEDIVELVEIKGQEYLFYPAFPIHVALIRGTYADESGNITFEKEVAPL EGTSVCQAVKNSGGIVVQVERVVKAGTLDPRHVKVPGIYVDYVVVADPEDH QQSLDCEYDPALSGEHRRPEVVGEPLPLSAKKVIGRRGAIELEKDVAVNLGVG APEYVASVADEEGIVDFMTLTA<u>L</u>SGAIGGVPAGGVRFGASYNADALIDQGYQF DYYDGGGLDLCYLGLAECDEKGNINVSRFGPRIAGCGGFINITQNTPKVFFCG TFTAGGLKVKIEDGKVIIVQEGKQKKFLKAVEQITFNGDVALANKQQVTYITERC VFLLKEDGLHLSEIAPGIDLQTQILDVMDFAPIIDRDANGQIKLMDAALFAEGLM GLKEMKS |
| 5 | *Peptostreptococcaceae* bacterium, Uniprot Accession No. U2L5C9 | MAKFVTLEEAVSVVKNGDTVATTGFVQVANPEALEWALGKRFEETKEPRDLT LFYCAGQGDGDCRAVNHFAKEGMLKRVVAGHFNMAPLLRQFISDNKCEAYN VPQGVLCNMVRDIAAKKPGVISHVGLNTFADPRIEGCKINLVTKEDIVELMMIN GEEKLFYKTFPLTIAFIKGTYADERGNVTLENEGIPSEATSIAQSVHNCGGKVIV QVEKVVAAGTLDPKLVKVPGIYVDYIVQVDDPSMRQQCYGVDYEPELAGNVYI PLSDIPLKTPLNERKIIARRGAFEIRKGNVGNLGIGVPEVVSEVVSEEGITDWLT LTVEVGPVGGSPQGKNRFGTAINAEAILDQPYQFDFYDGGGLDIAYLGLAOAD AKGNLNVSKFGDRVAGCGFIDISQNSKAVVFCGSFTAGGLKVEVNDGKLNIV QEGKVKKFVNKVQQITFSGEYARKTGQRVFYVTERAVFQMKPEGLTLEIAPG VDLEKDVLNQMEFKPLIAKDLKLMDERIFRPGPMGIKNDN |

Fig. 2E

| SEQ ID NO | Source | Sequence |
|---|---|---|
| 6 | *Firmicutes bacterium* CAG:102, Uniprot Accession No. R5ADR5 | MARQVKVITAAEEAAALIKNGDTVTTSGFVASAIPEALDRAVEERFLATGEPRDIT YVYCGSQGNKDGRGAEHFAHEGLLKRYIAGHWATVPALQKMALENKMEAYN VSQGALCHLFRDIAAHRPGCFTKVGLGTFIDPRNGGKVNDVTKEDIIELVNIK GQDYLFYPAFPINVALIRGTYADESGNISFEKEVSPLEGTSVCQAVKNSGGIVV VQVEKLVKAGTLDPRLVKVPGIYVDYVVADPKDHQQTLDCDYDPALSGEMR NPDVAPEPLPLSAKKIIGRRGAVELEKDVAVNLGVGAPEYVASVANEEGIGDF MTLTVEGGAVGGVPAGGIRFGSAYNADALLDQGYQFDFYDGGGLDLCYLGLA ECDPHGSINVSRFGPRIAGCGGFINITQCTPKVFFCGTFTAGGLKVKVEDGKV VIAQEGKNKKFVKSVEQVTFNGDIANKNGQHVMYITERCVFVLKEDGLHLTEIA PGIDLQTQILDQMEFEPIDRNADGSITLMDAKLFADGLMGLKEMKEGK |
| 7 | *Megasphaera elsdenii*, Uniprot Accession No. G0VND6 | MRKVEIITAEQAAQLVKDNDTITSIGFVSSAHPEALTKALEKRFLDTNTPQNLTYI YAGSQGKRDGRAAEHLAHTGLLKRAIIGHWQTVPAIGKLAVENKIEAYNFSQG TLVHWFRALAGHKLGVFTDIGLETFLDPRQLGGKLNDVTKEDLVKLIEVDGHE QLFYPTFPVNVAFLRGTYADESGNITMDEEIGPFESTSVAQAVHNCGGKVVVQ VKDVVAHGSLDPRMVKIPGIYVDYVVAAPEDHQOTYDCEYDPSLSGEHRAP EGATDAALPMSAKKIIGRRGALELTENAVVNLGVGAPEYVASVAGEEGIADTIT LTVEGGAIGGVPQGGARFGSSRNADAIIDHTYQFDFYDGGGLDIAYLGLAQCD GSGNINVSKFGTNVAGCGGFPNISQQTPNVYFCGTFTAGGLKIAVEDGKVKIL QEGKAKKFIKAVDQITFNGSYAARNGKHVLYITERCVFELTKEGLKLIEVAPGIDI EKDILAHMDFKPIIDNPKLMDARLFQDGPMGLKK |

Fig. 2F

| SEQ ID NO | Source | Sequence |
|---|---|---|
| 8 | Dyadobacter fermentans (strain ATCC 700827 / DSM 18053 / NS114), Uniprot Accession No. C6VTZ3 | MNAYIVAGYRTAVGKAPRGGFRFTRPDDLGAAVIKHLLEKTPQLDPTRVDDVI VGNAVPEAEQGMQMGRYVALLSLPKNVSGITINRYCGSGVEAIAMASAKIHAG MAECIIAGGTESMSLVPTMGWKTALNYEIAHTNPDYYLSMGLTAEQVAQDFKI SREAQDNFSFQSHQKALRAQKEGWFAEGIVPVTVKETYFDQASGKKKTKETV ISQDEGPRADTLEALNKLKPVFAAGGSVTAGNSSQTSDGAAFVLVMSERLVN ELGLKPIARMMSYATAGVDPRVMGIGPVAAVPLALKQAGLQLKDIQQVELNEA FAAQSLAVIQELGIDPEIVNPNGGAIALGHALGSTGARLSVQLFNEMKRRDQKY GMVTACVGGGQGVAGIYERLN |
| 9 | Salmonella enterica subsp. houtenaeserovar, Uniprot Accession No. V1HBS2 | MLSTKQFTAQQAVELIQDGDKVILGGFIGAVVPEAIEKAIEDKFLAEGHPCNLGL IFAAGQGDAKEKAINRLAHEGLVSSAIGGHWGLIPGLQRLASEGKITGYNLPQG VICHLLRDSAAGKAGTLTHVGLGTFVDPRIEGGKINAKTEDIVTYININDVENLL YKKLDANIAILRGTTADTHGNITMEDECLILENLAAQLVHNQGGKVIVQVKRIV PKGSLDPLQVKIPGIFVDALVVADGEAHMQTFAEAMNENYVGRGEKGIRERKI RPLDVKKVIARRAAMELKKNAIVNYGIGIPEIIAQVADEENVTQELIATVEPGAIG GSPAGGLSFGASAFPEAIITQDQMFDFYDGGGLDQAFLGLAETDAKGDLNVS KFGVKIAGCGGFINITQNAKHVFFCGSFTAGDSDIIVEEGKLIRRDGQIKKFIKH VQQITFSSDTARKNHKPVLYITERAVFRLAAETIELIEIAPGIDLQHDILDKMEFR PTISPALKEMDKRIFSEALMSLSLK |

Fig. 2G

| SEQ ID NO | Source | Sequence |
|---|---|---|
| 10 and 11 | Escherichia coli, see GenBank Accession Nos. AAC75282.1 & AAC75281.1, respectively | MDAKQRIARRVAQELRDGDIVNLGIGLPTMVANYLPEGIHITLQSENGFLGLGP VTTAHPDLVNAGGQPCGVLPGAAMFDSAMSFALIRGGHIDACVLGGLQVDEE ANLANWVVPGKMVPGMGGAMDLVTGSRKVIIAMEHCAKDGSAKILRRCTMPL TAQHAVHMLVTELAVFRFIDGKMWLTEIADGCDLATVRAKTEARFEVAADLNT QRGDL (SEQ ID NO:10, beta subunit)<br><br>MKTKLMTLQDATGFFRDGMTIMVGGFMGIGTPSRLVEALLESGVRDLTLIAND TAFVDTGIGPLIVNGRVRKVIASHIGTNPETGRRMISGEMDVVLVPQGTLIEQIR CGGAGLGGFLTPTGVGTVEEGKQTLTLDGKTWLLERPLRADLALIRAHRCDT LGNLTYQLSARNFNPLIALAADITLVEPDELVETGELQPDHIVTPGAVIDHIIVSQ ESK (SEQ ID NO: 11, alpha subunit) |

Fig. 2H

| SEQ ID NO | Source | Sequence |
|---|---|---|
| 12 and 13 | *Pseudomonas putida* GenBank Accession No. ACA73091.1 (A subunit) and ACA73090.1 (B subunit) | MINKTYESIASAVEGITDGSTIMVGGFGTAGMPSELIDALIDTGTRDLTIISNNAG NGEIGLAALLKAGSVRKVVCSFPRQSDSYVFDELYRAGKIELEVPQGNLAERI RAAGSSGIGAFFSPTGYGTLLSEGKETREIDGRQVLEMPLHADFALIKAYKGD RWGNLIYRKAARNFGPIMAMAAKTAIAQVDQIVELGELDPEHITPGIFVQRVVA VTGAASSIANAV (SEQ ID NO:12, A subunit)<br><br>MTITTKLSRTQMAQRVAADIQEGAYVNLGIGAPTLVANFLGDKEVFLHSENGLL GMGPSPAPGEEDDLINAGKQHVTLLTGGAFFHHADSFSMMRGGHLDIAVLG AFQVSVKGDLANWHTGAEGSIPAVGGAMDLATGARQVFVMMDHLTKSGESKI VPECTYPLTGIGCVSRIYTDLAVLEVTSDGLKVVEICADIDFDELQKLSGVPLIK (SEQ ID NO: 13, B subunit) |
| 14 | *Chromobacterium violaceum*, see GenBank Accession No. AAQ61181.1 | MKQQEVRQRAFAMPLTSPAFPPGPYRFVNREYMIITYRTDPAAIEAVLPEPLQ MAEPVVRYEFIRMPDSTGFGDYSESGQVIPVTFRGERGSYTLAMFLDDQPPL AGGRELWGFPKKAGKPRLEVHQDTLVGSLDFGPVRIATGTMGYKYEALDRSA LLASLAEPNFLLKIIPHVDGSPRICELVRYHTTDVAIKGAWSAPGSLELHPHALA PVAALPVLEVLSARHFVCDLTLDLGTVVFDYLRQ |
| 15 | *Clostridium acetobutylicum*, see GenBank Accession No. AAA63761.1 | MLKDEVIKQISTPLTSPAFPRGPYKFHNREYFNIVYRTDMDALRKVVPEPLEID EPLVRFEIMAMHDTSGLGCYTESGQAIPVSFNGVKGDYLHMMYLDNEPAIAVG RELSAYPKKLGYPKLFVDSDTLVGTLDYGKLRVATATMGYKHKALDANEAKD QICRPNYMLKIIPNYDGSPRICELINAKITDVVHEAWTGPTRLQLFDHAMAPLN DLPVKEIVSSSHILADIILPRAEVIYDYLK |

Fig. 21

| SEQ ID NO | Source | Sequence |
|---|---|---|
| 16 | *Nocardia rhamnosiphila*, see GenBank accession No. WP_030525792 | MRIRGAVLERIGAPVPYAESAPITISELELADPGPGEILVRIEAAGLCHSDLSVV DGNRVRPVPMLLGHEASGKVVQAGPGVDLPVGRRVAMTFLPRCGECAGCAS GGRTPCIPGSAANNAGELLGGGRRLHRDGAEVQHHLGVSGFATHAVVDRRS VVPVDDDVPPEVAAVLGCAVLTGGALLNSAKPAATDRVMVGLGGVGMAA VLVAVSLGVREVIAVDTVPDKLALARELGAGSAHTPAEVADRGVQAEVVVEAV GSARAFESAVAATAPGGVTVTVGLPAPDARATISPLGLVAQGRSIVGSYLGSA VPSRDIPEYVRMWREGRLPVEKLISARIGLADINGAMDELAAGHALRQVIMF |
| 17 | *Rhodococcus sp. ST-10*, see Uniprot Accession No. Q9ZN85 | MKAIQYTRIGAEPELTEIPKPEPGPGEVLLEVTAAGVCHSDDFIMSLPEEQYTY GLPLTLGHEGAGKVAAVGEGVEGLDIGTNVVVYGPWGCGNCWHCSQGLENY CSRAQELGINPPGLGAPGALAEFMIVDSPRHLVPIGDLDPVKTVPLTDAGLTPY HAIKRSLPKLRGGSYAVVIGTGGLGHVAIQLLRHLSAATVIALDVSADKLELATK VGAHEVVLSDKDAAENVRKITGSQAALVLDFVGYQPTIDTAMAVAGVGSDVT IVGIGDGQAHAKVGFFQSPYEASVTVPYWGARNELIELIDLAHAGIFDIAVETFS LDNGAEAYRRLAAGTLSGRAVVVPGL |

Fig. 2J

| SEQ ID NO | Source | Sequence |
|---|---|---|
| 18 | *Castellaniella defragrans*, see Uniprot Accession No. E1XUJ2 | MRFTLKTTAIVSAAALLAGF GPPPRAAELP PGRLATTEDY FAQQAKQAVT PDVMAQLAYM NYIDFISPFY SRGCSFEAWE LKHTPQRVIK YSIAFYAYGL ASVALIDPKL RALAGHDLDI AVSKMKCKRV WGDWEEDGFG TDPIEKENIM YKGHLNLMYG LYQLVTGSRR YEAEHAHLTR IIHDEIAANP FAGIVCEPDN YFVQCNSVAY LSLWVYDRLH GTDYRAATRA WLDFIQKDLI DPERGAFYLS YHPESGAVKP WISAYTTAWT LAMVHGMDPA FSERYYPRFK QTFVEVYDEG RKARVRETAG TDDADGGVGL ASAFTLLLAR EMGDQQLFDQ LLNHLEPPAK PSIVSASLRY EHPGSLLFDE LLFLAKVHAG FGALLRMPPP AAKLAGK |
| 19 | *Clostridium aminobutyricum*, see Uniprot Accession No. Q9RM86 | MDWKKIYEDRTCTADEAVKSIKSGDRVLFAHCVAEPPVLVEAMVANAAAYKN VTVSHMVTLGKGEYSKPEYKENFTFEGWFTSPSTRGSIAEGHGQFVPVFFHE VPSLIRKDIFHVDVFMVMVSPPDHNGFCCVGVSSDYTMQAIKSAKIVLAEVND QVPVVYGDTFVHVSEIDKFVETSHPLPEIGLPKIGEVEAAIGKHCASLIEDGSTL QLGIGAIPDAVLSQLKDKKHLGIHSEMISDGVVDLYEAGVIDCSQKSIDKGKMAI TFLMGTKRLYDFAANNPKVELKPVDYINHPSVVAQCSKMVCINACLQVDFMG QIVSDSIGTKQFSGVGGQVDFVRGASMSIDGKGKAIIAMPSVAKKKDGSMISKI VPFIDHGAAVTTSRNDADYVVTEYGIAEMKGKSLQDRARALINIAHPDFKDELK AEFEKRFNAAF |

Fig. 2K

| SEQ ID NO | Source | Sequence |
|---|---|---|
| 20 | *Candida parapsilosis*, see Uniprot Accession No. B2KJ46 | MGEIESYCNK ELGPLPTKAP TLSKNVLDLF SLKGKVASVT GSSGGIGWAV AEAYAQAGAD VAIWYNSHPA DEKAEHLQKT YGVHSKAYKC NISDPKSVEE TISQQEKDFG TIDVFVANAG VTWTQGPEID VDNYDSWNKI ISVDLNGVYY CSHNIGKIFK KNGKGSLIIT SSISGKIVNI PQLQAPYNTA KAACTHLAKS LAIEWAPFAR VNTISPGYID TDITDFASKD MKAKWWQLTP LGREGLTQEL VGGYLYLASN ASTFTTGSDV VIDGGYTCP |

SEQUENCE LISTING

<160> NUMBER OF SEQ ID NOS: 33

<210> SEQ ID NO 1
<211> LENGTH: 524
<212> TYPE: PRT
<213> ORGANISM: Clostridium propionicum

<400> SEQUENCE: 1

```
Met Arg Lys Val Pro Ile Ile Thr Ala Asp Glu Ala Ala Lys Leu Ile
1               5                   10                  15

Lys Asp Gly Asp Thr Val Thr Thr Ser Gly Phe Val Gly Asn Ala Ile
                20                  25                  30

Pro Glu Ala Leu Asp Arg Ala Val Glu Lys Arg Phe Leu Glu Thr Gly
            35                  40                  45

Glu Pro Lys Asn Ile Thr Tyr Val Tyr Cys Gly Ser Gln Gly Asn Arg
        50                  55                  60

Asp Gly Arg Gly Ala Glu His Phe Ala His Glu Gly Leu Leu Lys Arg
65                  70                  75                  80

Tyr Ile Ala Gly His Trp Ala Thr Val Pro Ala Leu Gly Lys Met Ala
                85                  90                  95

Met Glu Asn Lys Met Glu Ala Tyr Asn Val Ser Gln Gly Ala Leu Cys
            100                 105                 110

His Leu Phe Arg Asp Ile Ala Ser His Lys Pro Gly Val Phe Thr Lys
        115                 120                 125

Val Gly Ile Gly Thr Phe Ile Asp Pro Arg Asn Gly Gly Gly Lys Val
    130                 135                 140

Asn Asp Ile Thr Lys Glu Asp Ile Val Glu Leu Val Glu Ile Lys Gly
```

```
            145                 150                 155                 160

Gln Glu Tyr Leu Phe Tyr Pro Ala Phe Pro Ile His Val Ala Leu Ile
                        165                 170                 175

Arg Gly Thr Tyr Ala Asp Glu Ser Gly Asn Ile Thr Phe Glu Lys Glu
                    180                 185                 190

Val Ala Pro Leu Glu Gly Thr Ser Val Cys Gln Ala Val Lys Asn Ser
                195                 200                 205

Gly Gly Ile Val Val Gln Val Glu Arg Val Val Lys Ala Gly Thr
            210                 215                 220

Leu Asp Pro Arg His Val Lys Val Pro Gly Ile Tyr Val Asp Tyr Val
        225                 230                 235                 240

Val Val Ala Asp Pro Glu Asp His Gln Gln Ser Leu Asp Cys Glu Tyr
                        245                 250                 255

Asp Pro Ala Leu Ser Gly Glu His Arg Arg Pro Glu Val Val Gly Glu
                    260                 265                 270

Pro Leu Pro Leu Ser Ala Lys Lys Val Ile Gly Arg Arg Gly Ala Ile
                275                 280                 285

Glu Leu Glu Lys Asp Val Ala Val Asn Leu Gly Val Gly Ala Pro Glu
            290                 295                 300

Tyr Val Ala Ser Val Ala Asp Glu Glu Gly Ile Val Asp Phe Met Thr
        305                 310                 315                 320

Leu Thr Ala Glu Ser Gly Ala Ile Gly Gly Val Pro Ala Gly Gly Val
                        325                 330                 335

Arg Phe Gly Ala Ser Tyr Asn Ala Asp Ala Leu Ile Asp Gln Gly Tyr
                    340                 345                 350

Gln Phe Asp Tyr Tyr Asp Gly Gly Leu Asp Leu Cys Tyr Leu Gly
                355                 360                 365

Leu Ala Glu Cys Asp Glu Lys Gly Asn Ile Asn Val Ser Arg Phe Gly
            370                 375                 380

Pro Arg Ile Ala Gly Cys Gly Gly Phe Ile Asn Ile Thr Gln Asn Thr
        385                 390                 395                 400

Pro Lys Val Phe Phe Cys Gly Thr Phe Thr Ala Gly Gly Leu Lys Val
                        405                 410                 415

Lys Ile Glu Asp Gly Lys Val Ile Ile Val Gln Glu Gly Lys Gln Lys
                    420                 425                 430

Lys Phe Leu Lys Ala Val Glu Gln Ile Thr Phe Asn Gly Asp Val Ala
                435                 440                 445

Leu Ala Asn Lys Gln Gln Val Thr Tyr Ile Thr Glu Arg Cys Val Phe
            450                 455                 460

Leu Leu Lys Glu Asp Gly Leu His Leu Ser Glu Ile Ala Pro Gly Ile
        465                 470                 475                 480

Asp Leu Gln Thr Gln Ile Leu Asp Val Met Asp Phe Ala Pro Ile Ile
                        485                 490                 495

Asp Arg Asp Ala Asn Gly Gln Ile Lys Leu Met Asp Ala Ala Leu Phe
                    500                 505                 510

Ala Glu Gly Leu Met Gly Leu Lys Glu Met Lys Ser
                515                 520

<210> SEQ ID NO 2
<211> LENGTH: 541
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 2

```
Met Gly His His His His His Ser Ser Gly Leu Val Pro Arg Gly
1               5                   10                  15

Ser Met Arg Lys Val Pro Ile Ile Thr Ala Asp Glu Ala Ala Lys Leu
            20                  25                  30

Ile Lys Asp Gly Asp Thr Val Thr Thr Ser Gly Phe Val Gly Asn Ala
            35                  40                  45

Ile Pro Glu Ala Leu Asp Arg Ala Val Glu Lys Arg Phe Leu Glu Thr
        50                  55                  60

Gly Glu Pro Lys Asn Ile Thr Tyr Val Tyr Cys Gly Ser Gln Gly Asn
65                  70                  75                  80

Arg Asp Gly Arg Gly Ala Glu His Phe Ala His Glu Gly Leu Leu Lys
                85                  90                  95

Arg Tyr Ile Ala Gly His Trp Ala Thr Val Pro Ala Leu Gly Lys Met
            100                 105                 110

Ala Met Glu Asn Lys Met Glu Ala Tyr Asn Val Ser Gln Gly Ala Leu
        115                 120                 125

Cys His Leu Phe Arg Asp Ile Ala Ser His Lys Pro Gly Val Phe Thr
130                 135                 140

Lys Val Gly Ile Gly Thr Phe Ile Asp Pro Arg Asn Gly Gly Gly Lys
145                 150                 155                 160

Val Asn Asp Ile Thr Lys Glu Asp Ile Val Glu Leu Val Glu Ile Lys
                165                 170                 175

Gly Gln Glu Tyr Leu Phe Tyr Pro Ala Phe Pro Ile His Val Ala Leu
            180                 185                 190

Ile Arg Gly Thr Tyr Ala Asp Glu Ser Gly Asn Ile Thr Phe Glu Lys
        195                 200                 205

Glu Val Ala Pro Leu Glu Gly Thr Ser Val Cys Gln Ala Val Lys Asn
210                 215                 220

Ser Gly Gly Ile Val Val Val Gln Val Glu Arg Val Lys Ala Gly
225                 230                 235                 240

Thr Leu Asp Pro Arg His Val Lys Val Pro Gly Ile Tyr Val Asp Tyr
                245                 250                 255

Val Val Val Ala Asp Pro Glu Asp His Gln Gln Ser Leu Asp Cys Glu
            260                 265                 270

Tyr Asp Pro Ala Leu Ser Gly Glu His Arg Arg Pro Glu Val Val Gly
        275                 280                 285

Glu Pro Leu Pro Leu Ser Ala Lys Lys Val Ile Gly Arg Arg Gly Ala
290                 295                 300

Ile Glu Leu Glu Lys Asp Val Ala Val Asn Leu Gly Val Gly Ala Pro
305                 310                 315                 320

Glu Tyr Val Ala Ser Val Ala Asp Glu Glu Gly Ile Val Asp Phe Met
                325                 330                 335

Thr Leu Thr Ala Glu Ser Gly Ala Ile Gly Gly Val Pro Ala Gly Gly
            340                 345                 350

Val Arg Phe Gly Ala Ser Tyr Asn Ala Asp Ala Leu Ile Asp Gln Gly
        355                 360                 365

Tyr Gln Phe Asp Tyr Tyr Asp Gly Gly Gly Leu Asp Leu Cys Tyr Leu
370                 375                 380

Gly Leu Ala Glu Cys Asp Glu Lys Gly Asn Ile Asn Val Ser Arg Phe
385                 390                 395                 400

Gly Pro Arg Ile Ala Gly Cys Gly Gly Phe Ile Asn Ile Thr Gln Asn
```

```
                    405                 410                 415
Thr Pro Lys Val Phe Cys Gly Thr Phe Thr Ala Gly Gly Leu Lys
            420                 425                 430

Val Lys Ile Glu Asp Gly Lys Val Ile Val Gln Glu Gly Lys Gln
            435                 440                 445

Lys Lys Phe Leu Lys Ala Val Glu Gln Ile Thr Phe Asn Gly Asp Val
            450                 455                 460

Ala Leu Ala Asn Lys Gln Gln Val Thr Tyr Ile Thr Glu Arg Cys Val
465                 470                 475                 480

Phe Leu Leu Lys Glu Asp Gly Leu His Leu Ser Glu Ile Ala Pro Gly
            485                 490                 495

Ile Asp Leu Gln Thr Gln Ile Leu Asp Val Met Asp Phe Ala Pro Ile
            500                 505                 510

Ile Asp Arg Asp Ala Asn Gly Gln Ile Lys Leu Met Asp Ala Ala Leu
            515                 520                 525

Phe Ala Glu Gly Leu Met Gly Leu Lys Glu Met Lys Ser
            530                 535                 540

<210> SEQ ID NO 3
<211> LENGTH: 541
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gly His His His His His His Ser Ser Gly Leu Val Pro Arg Gly
1               5                   10                  15

Ser Met Arg Lys Val Pro Ile Ile Thr Ala Asp Glu Ala Ala Lys Leu
            20                  25                  30

Ile Lys Asp Gly Asp Thr Val Thr Thr Ser Gly Phe Val Gly Asn Ala
            35                  40                  45

Ile Pro Glu Ala Leu Asp Arg Ala Val Glu Lys Arg Phe Leu Glu Thr
        50                  55                  60

Gly Glu Pro Lys Asn Ile Thr Tyr Val Tyr Cys Gly Ser Gln Gly Asn
65                  70                  75                  80

Arg Asp Gly Arg Gly Ala Glu His Phe Ala His Glu Gly Leu Leu Lys
            85                  90                  95

Arg Tyr Ile Ala Gly His Trp Ala Thr Val Pro Ala Leu Gly Lys Met
            100                 105                 110

Ala Met Glu Asn Lys Met Glu Ala Tyr Asn Val Ser Gln Gly Ala Leu
            115                 120                 125

Cys His Leu Phe Arg Asp Ile Ala Ser His Lys Pro Gly Val Phe Thr
        130                 135                 140

Lys Val Gly Ile Gly Thr Phe Ile Asp Pro Arg Asn Gly Gly Gly Lys
145                 150                 155                 160

Val Asn Asp Ile Thr Lys Glu Asp Ile Val Glu Leu Val Glu Ile Lys
            165                 170                 175

Gly Gln Glu Tyr Leu Phe Tyr Pro Ala Phe Pro Ile His Val Ala Leu
            180                 185                 190

Ile Arg Gly Thr Tyr Ala Asp Glu Ser Gly Asn Ile Thr Phe Glu Lys
            195                 200                 205

Glu Val Ala Pro Leu Glu Gly Thr Ser Val Cys Gln Ala Val Lys Asn
        210                 215                 220
```

```
Ser Gly Gly Ile Val Val Gln Val Glu Arg Val Lys Ala Gly
225                 230                 235                 240

Thr Leu Asp Pro Arg His Val Lys Val Pro Gly Ile Tyr Val Asp Tyr
            245                 250                 255

Val Val Val Ala Asp Pro Glu Asp His Gln Gln Ser Leu Asp Cys Glu
        260                 265                 270

Tyr Asp Pro Ala Leu Ser Gly Glu His Arg Arg Pro Glu Val Val Gly
    275                 280                 285

Glu Pro Leu Pro Leu Ser Ala Lys Lys Val Ile Gly Arg Arg Gly Ala
    290                 295                 300

Ile Glu Leu Glu Lys Asp Val Ala Val Asn Leu Gly Val Gly Ala Pro
305                 310                 315                 320

Glu Tyr Val Ala Ser Val Ala Asp Glu Glu Gly Ile Val Asp Phe Met
                325                 330                 335

Thr Leu Thr Ala Gly Ser Gly Ala Ile Gly Gly Val Pro Ala Gly Gly
            340                 345                 350

Val Arg Phe Gly Ala Ser Tyr Asn Ala Asp Ala Leu Ile Asp Gln Gly
        355                 360                 365

Tyr Gln Phe Asp Tyr Tyr Asp Gly Gly Gly Leu Asp Leu Cys Tyr Leu
    370                 375                 380

Gly Leu Ala Glu Cys Asp Glu Lys Gly Asn Ile Asn Val Ser Arg Phe
385                 390                 395                 400

Gly Pro Arg Ile Ala Gly Cys Gly Gly Phe Ile Asn Ile Thr Gln Asn
                405                 410                 415

Thr Pro Lys Val Phe Phe Cys Gly Thr Phe Thr Ala Gly Gly Leu Lys
            420                 425                 430

Val Lys Ile Glu Asp Gly Lys Val Ile Ile Val Gln Glu Gly Lys Gln
        435                 440                 445

Lys Lys Phe Leu Lys Ala Val Glu Gln Ile Thr Phe Asn Gly Asp Val
    450                 455                 460

Ala Leu Ala Asn Lys Gln Gln Val Thr Tyr Ile Thr Glu Arg Cys Val
465                 470                 475                 480

Phe Leu Leu Lys Glu Asp Gly Leu His Leu Ser Glu Ile Ala Pro Gly
                485                 490                 495

Ile Asp Leu Gln Thr Gln Ile Leu Asp Val Met Asp Phe Ala Pro Ile
            500                 505                 510

Ile Asp Arg Asp Ala Asn Gly Gln Ile Lys Leu Met Asp Ala Ala Leu
        515                 520                 525

Phe Ala Glu Gly Leu Met Gly Leu Lys Glu Met Lys Ser
    530                 535                 540

<210> SEQ ID NO 4
<211> LENGTH: 541
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly His His His His His Ser Ser Gly Leu Val Pro Arg Gly
1               5                   10                  15

Ser Met Arg Lys Val Pro Ile Ile Thr Ala Asp Glu Ala Ala Lys Leu
                20                  25                  30

Ile Lys Asp Gly Asp Thr Val Thr Ser Gly Phe Val Gly Asn Ala
            35                  40                  45
```

-continued

Ile Pro Glu Ala Leu Asp Arg Ala Val Glu Lys Arg Phe Leu Glu Thr
 50                  55                  60

Gly Glu Pro Lys Asn Ile Thr Tyr Val Tyr Cys Gly Ser Gln Gly Asn
 65                  70                  75                  80

Arg Asp Gly Arg Gly Ala Glu His Phe Ala His Glu Gly Leu Leu Lys
                 85                  90                  95

Arg Tyr Ile Ala Gly His Trp Ala Thr Val Pro Ala Leu Gly Lys Met
                100                 105                 110

Ala Met Glu Asn Lys Met Glu Ala Tyr Asn Val Ser Gln Gly Ala Leu
            115                 120                 125

Cys His Leu Phe Arg Asp Ile Ala Ser His Lys Pro Gly Val Phe Thr
        130                 135                 140

Lys Val Gly Ile Gly Thr Phe Ile Asp Pro Arg Asn Gly Gly Lys
145                 150                 155                 160

Val Asn Asp Ile Thr Lys Glu Asp Ile Val Glu Leu Val Glu Ile Lys
                165                 170                 175

Gly Gln Glu Tyr Leu Phe Tyr Pro Ala Phe Pro Ile His Val Ala Leu
                180                 185                 190

Ile Arg Gly Thr Tyr Ala Asp Glu Ser Gly Asn Ile Thr Phe Glu Lys
        195                 200                 205

Glu Val Ala Pro Leu Glu Gly Thr Ser Val Cys Gln Ala Val Lys Asn
    210                 215                 220

Ser Gly Gly Ile Val Val Gln Val Glu Arg Val Val Lys Ala Gly
225                 230                 235                 240

Thr Leu Asp Pro Arg His Val Lys Val Pro Gly Ile Tyr Val Asp Tyr
                245                 250                 255

Val Val Val Ala Asp Pro Glu Asp His Gln Gln Ser Leu Asp Cys Glu
            260                 265                 270

Tyr Asp Pro Ala Leu Ser Gly Glu His Arg Arg Pro Glu Val Val Gly
        275                 280                 285

Glu Pro Leu Pro Leu Ser Ala Lys Lys Val Ile Gly Arg Arg Gly Ala
    290                 295                 300

Ile Glu Leu Glu Lys Asp Val Ala Val Asn Leu Gly Val Gly Ala Pro
305                 310                 315                 320

Glu Tyr Val Ala Ser Val Ala Asp Glu Glu Gly Ile Val Asp Phe Met
                325                 330                 335

Thr Leu Thr Ala Leu Ser Gly Ala Ile Gly Gly Val Pro Ala Gly Gly
            340                 345                 350

Val Arg Phe Gly Ala Ser Tyr Asn Ala Asp Ala Leu Ile Asp Gln Gly
        355                 360                 365

Tyr Gln Phe Asp Tyr Tyr Asp Gly Gly Gly Leu Asp Leu Cys Tyr Leu
    370                 375                 380

Gly Leu Ala Glu Cys Asp Glu Lys Gly Asn Ile Asn Val Ser Arg Phe
385                 390                 395                 400

Gly Pro Arg Ile Ala Gly Cys Gly Gly Phe Ile Asn Ile Thr Gln Asn
                405                 410                 415

Thr Pro Lys Val Phe Phe Cys Gly Thr Phe Thr Ala Gly Gly Leu Lys
            420                 425                 430

Val Lys Ile Glu Asp Gly Lys Val Ile Val Gln Glu Gly Lys Gln
        435                 440                 445

Lys Lys Phe Leu Lys Ala Val Glu Gln Ile Thr Phe Asn Gly Asp Val
    450                 455                 460

-continued

```
Ala Leu Ala Asn Lys Gln Gln Val Thr Tyr Ile Thr Glu Arg Cys Val
465                 470                 475                 480

Phe Leu Leu Lys Glu Asp Gly Leu His Leu Ser Glu Ile Ala Pro Gly
                485                 490                 495

Ile Asp Leu Gln Thr Gln Ile Leu Asp Val Met Asp Phe Ala Pro Ile
            500                 505                 510

Ile Asp Arg Asp Ala Asn Gly Gln Ile Lys Leu Met Asp Ala Ala Leu
        515                 520                 525

Phe Ala Glu Gly Leu Met Gly Leu Lys Glu Met Lys Ser
530                 535                 540

<210> SEQ ID NO 5
<211> LENGTH: 519
<212> TYPE: PRT
<213> ORGANISM: Unknown
<220> FEATURE:
<223> OTHER INFORMATION: Description of Unknown: Peptostreptococcaceae
      bacterium polypeptide

<400> SEQUENCE: 5

Met Ala Lys Phe Val Thr Leu Glu Glu Ala Val Ser Val Val Lys Asn
1               5                   10                  15

Gly Asp Thr Val Ala Thr Thr Gly Phe Val Gln Val Ala Asn Pro Glu
            20                  25                  30

Ala Leu Glu Trp Ala Leu Gly Lys Arg Phe Glu Glu Thr Lys Glu Pro
        35                  40                  45

Arg Asp Leu Thr Leu Phe Tyr Cys Ala Gly Gln Gly Asp Gly Asp Cys
    50                  55                  60

Arg Ala Val Asn His Phe Ala Lys Glu Gly Met Leu Lys Arg Val Val
65                  70                  75                  80

Ala Gly His Phe Asn Met Ala Pro Leu Leu Arg Gln Phe Ile Ser Asp
                85                  90                  95

Asn Lys Cys Glu Ala Tyr Asn Val Pro Gln Gly Val Leu Cys Asn Met
            100                 105                 110

Val Arg Asp Ile Ala Ala Lys Lys Pro Gly Val Ile Ser His Val Gly
        115                 120                 125

Leu Asn Thr Phe Ala Asp Pro Arg Ile Glu Gly Cys Lys Ile Asn Leu
    130                 135                 140

Val Thr Lys Glu Asp Ile Val Glu Leu Met Met Ile Asn Gly Glu Glu
145                 150                 155                 160

Lys Leu Phe Tyr Lys Thr Phe Pro Leu Thr Ile Ala Phe Ile Lys Gly
                165                 170                 175

Thr Tyr Ala Asp Glu Arg Gly Asn Val Thr Leu Glu Asn Glu Gly Ile
            180                 185                 190

Pro Ser Glu Ala Thr Ser Ile Ala Gln Ser Val His Asn Cys Gly Gly
        195                 200                 205

Lys Val Ile Val Gln Val Glu Lys Val Val Ala Gly Thr Leu Asp
    210                 215                 220

Pro Lys Leu Val Lys Val Pro Gly Ile Tyr Val Asp Tyr Ile Val Gln
225                 230                 235                 240

Val Asp Asp Pro Ser Met Arg Gln Gln Cys Tyr Gly Val Asp Tyr Glu
                245                 250                 255

Pro Glu Leu Ala Gly Asn Val Tyr Ile Pro Leu Ser Asp Ile Pro Leu
            260                 265                 270

Lys Thr Pro Leu Asn Glu Arg Lys Ile Ile Ala Arg Arg Gly Ala Phe
        275                 280                 285
```

Glu Ile Arg Lys Gly Asn Val Gly Asn Leu Gly Ile Gly Val Pro Glu
    290                 295                 300

Val Val Ser Glu Val Val Ser Glu Glu Gly Ile Thr Asp Trp Leu Thr
305                 310                 315                 320

Leu Thr Val Glu Val Gly Pro Val Gly Gly Ser Pro Gln Gly Lys Asn
            325                 330                 335

Arg Phe Gly Thr Ala Ile Asn Ala Glu Ala Ile Leu Asp Gln Pro Tyr
                340                 345                 350

Gln Phe Asp Phe Tyr Asp Gly Gly Leu Asp Ile Ala Tyr Leu Gly
            355                 360                 365

Leu Ala Gln Ala Asp Ala Lys Gly Asn Leu Asn Val Ser Lys Phe Gly
    370                 375                 380

Asp Arg Val Ala Gly Cys Gly Gly Phe Ile Asp Ile Ser Gln Asn Ser
385                 390                 395                 400

Lys Ala Val Val Phe Cys Gly Ser Phe Thr Ala Gly Gly Leu Lys Val
            405                 410                 415

Glu Val Asn Asp Gly Lys Leu Asn Ile Val Gln Glu Gly Lys Val Lys
                420                 425                 430

Lys Phe Val Asn Lys Val Gln Gln Ile Thr Phe Ser Gly Glu Tyr Ala
    435                 440                 445

Arg Lys Thr Gly Gln Arg Val Phe Tyr Val Thr Glu Arg Ala Val Phe
450                 455                 460

Gln Met Lys Pro Glu Gly Leu Thr Leu Ile Glu Ile Ala Pro Gly Val
465                 470                 475                 480

Asp Leu Glu Lys Asp Val Leu Asn Gln Met Glu Phe Lys Pro Leu Ile
            485                 490                 495

Ala Lys Asp Leu Lys Leu Met Asp Glu Arg Ile Phe Arg Pro Gly Pro
                500                 505                 510

Met Gly Ile Lys Asn Asp Asn
        515

<210> SEQ ID NO 6
<211> LENGTH: 527
<212> TYPE: PRT
<213> ORGANISM: Unknown
<220> FEATURE:
<223> OTHER INFORMATION: Description of Unknown: Firmicutes bacterium
      polypeptide

<400> SEQUENCE: 6

Met Ala Arg Gln Val Lys Val Ile Thr Ala Ala Glu Ala Ala Ala Leu
1               5                   10                  15

Ile Lys Asn Gly Asp Thr Val Thr Thr Ser Gly Phe Val Ala Ser Ala
            20                  25                  30

Ile Pro Glu Ala Leu Asp Arg Ala Val Glu Glu Arg Phe Leu Ala Thr
        35                  40                  45

Gly Glu Pro Arg Asp Ile Thr Tyr Val Tyr Cys Gly Ser Gln Gly Asn
    50                  55                  60

Lys Asp Gly Arg Gly Ala Glu His Phe Ala His Glu Gly Leu Leu Lys
65                  70                  75                  80

Arg Tyr Ile Ala Gly His Trp Ala Thr Val Pro Ala Leu Gln Lys Met
                85                  90                  95

Ala Leu Glu Asn Lys Met Glu Ala Tyr Asn Val Ser Gln Gly Ala Leu
            100                 105                 110

Cys His Leu Phe Arg Asp Ile Ala Ala His Arg Pro Gly Cys Phe Thr

```
            115                 120                 125
Lys Val Gly Leu Gly Thr Phe Ile Asp Pro Arg Asn Gly Gly Lys
        130                 135                 140

Val Asn Asp Val Thr Lys Glu Asp Ile Ile Glu Leu Val Asn Ile Lys
145                 150                 155                 160

Gly Gln Asp Tyr Leu Phe Tyr Pro Ala Phe Pro Ile Asn Val Ala Leu
                165                 170                 175

Ile Arg Gly Thr Tyr Ala Asp Glu Ser Gly Asn Ile Ser Phe Glu Lys
            180                 185                 190

Glu Val Ser Pro Leu Glu Gly Thr Ser Val Cys Gln Ala Val Lys Asn
            195                 200                 205

Ser Gly Gly Ile Val Val Gln Val Glu Lys Leu Val Lys Ala Gly
        210                 215                 220

Thr Leu Asp Pro Arg Leu Val Lys Val Pro Gly Ile Tyr Val Asp Tyr
225                 230                 235                 240

Val Val Val Ala Asp Pro Lys Asp His Gln Gln Thr Leu Asp Cys Asp
                245                 250                 255

Tyr Asp Pro Ala Leu Ser Gly Glu Met Arg Asn Pro Asp Val Ala Pro
            260                 265                 270

Glu Pro Leu Pro Leu Ser Ala Lys Lys Ile Ile Gly Arg Arg Gly Ala
            275                 280                 285

Val Glu Leu Glu Lys Asp Val Ala Val Asn Leu Gly Val Gly Ala Pro
        290                 295                 300

Glu Tyr Val Ala Ser Val Ala Asn Glu Glu Gly Ile Gly Asp Phe Met
305                 310                 315                 320

Thr Leu Thr Val Glu Gly Ala Val Gly Gly Val Pro Ala Gly Gly
                325                 330                 335

Ile Arg Phe Gly Ser Ala Tyr Asn Ala Asp Ala Leu Leu Asp Gln Gly
            340                 345                 350

Tyr Gln Phe Asp Phe Tyr Asp Gly Gly Gly Leu Asp Leu Cys Tyr Leu
            355                 360                 365

Gly Leu Ala Glu Cys Asp Pro His Gly Ser Ile Asn Val Ser Arg Phe
        370                 375                 380

Gly Pro Arg Ile Ala Gly Cys Gly Gly Phe Ile Asn Ile Thr Gln Cys
385                 390                 395                 400

Thr Pro Lys Val Phe Phe Cys Gly Thr Phe Thr Ala Gly Gly Leu Lys
                405                 410                 415

Val Lys Val Glu Asp Gly Lys Val Val Ile Ala Gln Glu Gly Lys Asn
            420                 425                 430

Lys Lys Phe Val Lys Ser Val Glu Gln Val Thr Phe Asn Gly Asp Ile
            435                 440                 445

Ala Asn Lys Asn Gly Gln His Val Met Tyr Ile Thr Glu Arg Cys Val
        450                 455                 460

Phe Val Leu Lys Glu Asp Gly Leu His Leu Thr Glu Ile Ala Pro Gly
465                 470                 475                 480

Ile Asp Leu Gln Thr Gln Ile Leu Asp Gln Met Glu Phe Glu Pro Ile
                485                 490                 495

Ile Asp Arg Asn Ala Asp Gly Ser Ile Thr Leu Met Ala Lys Leu
            500                 505                 510

Phe Ala Asp Gly Leu Met Gly Leu Lys Glu Met Lys Glu Gly Lys
            515                 520                 525

<210> SEQ ID NO 7
```

<211> LENGTH: 517
<212> TYPE: PRT
<213> ORGANISM: Megasphaera elsdenii

<400> SEQUENCE: 7

```
Met Arg Lys Val Glu Ile Ile Thr Ala Glu Gln Ala Ala Gln Leu Val
1               5                   10                  15

Lys Asp Asn Asp Thr Ile Thr Ser Ile Gly Phe Val Ser Ser Ala His
            20                  25                  30

Pro Glu Ala Leu Thr Lys Ala Leu Glu Lys Arg Phe Leu Asp Thr Asn
        35                  40                  45

Thr Pro Gln Asn Leu Thr Tyr Ile Tyr Ala Gly Ser Gln Gly Lys Arg
    50                  55                  60

Asp Gly Arg Ala Ala Glu His Leu Ala His Thr Gly Leu Leu Lys Arg
65                  70                  75                  80

Ala Ile Ile Gly His Trp Gln Thr Val Pro Ala Ile Gly Lys Leu Ala
                85                  90                  95

Val Glu Asn Lys Ile Glu Ala Tyr Asn Phe Ser Gln Gly Thr Leu Val
            100                 105                 110

His Trp Phe Arg Ala Leu Ala Gly His Lys Leu Gly Val Phe Thr Asp
        115                 120                 125

Ile Gly Leu Glu Thr Phe Leu Asp Pro Arg Gln Leu Gly Gly Lys Leu
    130                 135                 140

Asn Asp Val Thr Lys Glu Asp Leu Val Lys Leu Ile Glu Val Asp Gly
145                 150                 155                 160

His Glu Gln Leu Phe Tyr Pro Thr Phe Pro Val Asn Val Ala Phe Leu
                165                 170                 175

Arg Gly Thr Tyr Ala Asp Glu Ser Gly Asn Ile Thr Met Asp Glu Glu
            180                 185                 190

Ile Gly Pro Phe Glu Ser Thr Ser Val Ala Gln Ala Val His Asn Cys
        195                 200                 205

Gly Gly Lys Val Val Gln Val Lys Asp Val Val Ala His Gly Ser
    210                 215                 220

Leu Asp Pro Arg Met Val Lys Ile Pro Gly Ile Tyr Val Asp Tyr Val
225                 230                 235                 240

Val Val Ala Ala Pro Glu Asp His Gln Gln Thr Tyr Asp Cys Glu Tyr
                245                 250                 255

Asp Pro Ser Leu Ser Gly Glu His Arg Ala Pro Glu Gly Ala Thr Asp
            260                 265                 270

Ala Ala Leu Pro Met Ser Ala Lys Lys Ile Ile Gly Arg Arg Gly Ala
        275                 280                 285

Leu Glu Leu Thr Glu Asn Ala Val Val Asn Leu Gly Val Gly Ala Pro
    290                 295                 300

Glu Tyr Val Ala Ser Val Ala Gly Glu Glu Gly Ile Ala Asp Thr Ile
305                 310                 315                 320

Thr Leu Thr Val Glu Gly Gly Ala Ile Gly Gly Val Pro Gln Gly Gly
                325                 330                 335

Ala Arg Phe Gly Ser Ser Arg Asn Ala Asp Ala Ile Ile Asp His Thr
            340                 345                 350

Tyr Gln Phe Asp Phe Tyr Asp Gly Gly Leu Asp Ile Ala Tyr Leu
        355                 360                 365

Gly Leu Ala Gln Cys Asp Gly Ser Gly Asn Ile Asn Val Ser Lys Phe
    370                 375                 380

Gly Thr Asn Val Ala Gly Cys Gly Gly Phe Pro Asn Ile Ser Gln Gln
```

```
            385                 390                 395                 400
Thr Pro Asn Val Tyr Phe Cys Gly Thr Phe Thr Ala Gly Gly Leu Lys
                    405                 410                 415

Ile Ala Val Glu Asp Gly Lys Val Lys Ile Leu Gln Glu Gly Lys Ala
                420                 425                 430

Lys Lys Phe Ile Lys Ala Val Asp Gln Ile Thr Phe Asn Gly Ser Tyr
            435                 440                 445

Ala Ala Arg Asn Gly Lys His Val Leu Tyr Ile Thr Glu Arg Cys Val
        450                 455                 460

Phe Glu Leu Thr Lys Glu Gly Leu Lys Leu Ile Glu Val Ala Pro Gly
465                 470                 475                 480

Ile Asp Ile Glu Lys Asp Ile Leu Ala His Met Asp Phe Lys Pro Ile
                485                 490                 495

Ile Asp Asn Pro Lys Leu Met Asp Ala Arg Leu Phe Gln Asp Gly Pro
            500                 505                 510

Met Gly Leu Lys Lys
            515

<210> SEQ ID NO 8
<211> LENGTH: 392
<212> TYPE: PRT
<213> ORGANISM: Dyadobacter fermentans

<400> SEQUENCE: 8

Met Asn Ala Tyr Ile Val Ala Gly Tyr Arg Thr Ala Val Gly Lys Ala
1               5                   10                  15

Pro Arg Gly Gly Phe Arg Phe Thr Arg Pro Asp Asp Leu Gly Ala Ala
                20                  25                  30

Val Ile Lys His Leu Leu Glu Lys Thr Pro Gln Leu Asp Pro Thr Arg
            35                  40                  45

Val Asp Asp Val Ile Val Gly Asn Ala Val Pro Glu Ala Glu Gln Gly
        50                  55                  60

Met Gln Met Gly Arg Tyr Val Ala Leu Leu Ser Leu Pro Lys Asn Val
65                  70                  75                  80

Ser Gly Ile Thr Ile Asn Arg Tyr Cys Gly Ser Gly Val Glu Ala Ile
                85                  90                  95

Ala Met Ala Ser Ala Lys Ile His Ala Gly Met Ala Glu Cys Ile Ile
                100                 105                 110

Ala Gly Gly Thr Glu Ser Met Ser Leu Val Pro Thr Met Gly Trp Lys
            115                 120                 125

Thr Ala Leu Asn Tyr Glu Ile Ala His Thr Asn Pro Asp Tyr Tyr Leu
        130                 135                 140

Ser Met Gly Leu Thr Ala Glu Gln Val Ala Gln Asp Phe Lys Ile Ser
145                 150                 155                 160

Arg Glu Ala Gln Asp Asn Phe Ser Phe Gln Ser His Gln Lys Ala Leu
                165                 170                 175

Arg Ala Gln Lys Glu Gly Trp Phe Ala Glu Gly Ile Val Pro Val Thr
            180                 185                 190

Val Lys Glu Thr Tyr Phe Asp Gln Ala Ser Gly Lys Lys Lys Thr Lys
        195                 200                 205

Glu Thr Val Ile Ser Gln Asp Glu Gly Pro Arg Ala Asp Thr Thr Leu
    210                 215                 220

Glu Ala Leu Asn Lys Leu Lys Pro Val Phe Ala Ala Gly Gly Ser Val
225                 230                 235                 240
```

```
Thr Ala Gly Asn Ser Ser Gln Thr Ser Asp Gly Ala Ala Phe Val Leu
                245                 250                 255

Val Met Ser Glu Arg Leu Val Asn Glu Leu Gly Leu Lys Pro Ile Ala
            260                 265                 270

Arg Met Met Ser Tyr Ala Thr Ala Gly Val Asp Pro Arg Val Met Gly
        275                 280                 285

Ile Gly Pro Val Ala Ala Val Pro Leu Ala Leu Lys Gln Ala Gly Leu
    290                 295                 300

Gln Leu Lys Asp Ile Gln Val Glu Leu Asn Glu Ala Phe Ala Ala
305                 310                 315                 320

Gln Ser Leu Ala Val Ile Gln Glu Leu Gly Ile Asp Pro Glu Ile Val
                325                 330                 335

Asn Pro Asn Gly Gly Ala Ile Ala Leu Gly His Ala Leu Gly Ser Thr
            340                 345                 350

Gly Ala Arg Leu Ser Val Gln Leu Phe Asn Glu Met Lys Arg Arg Asp
        355                 360                 365

Gln Lys Tyr Gly Met Val Thr Ala Cys Val Gly Gly Gln Gly Val
    370                 375                 380

Ala Gly Ile Tyr Glu Arg Leu Asn
385                 390

<210> SEQ ID NO 9
<211> LENGTH: 518
<212> TYPE: PRT
<213> ORGANISM: Salmonella enterica

<400> SEQUENCE: 9

Met Leu Ser Thr Lys Gln Phe Thr Ala Gln Gln Ala Val Glu Leu Ile
1               5                   10                  15

Gln Asp Gly Asp Lys Val Ile Leu Gly Gly Phe Ile Gly Ala Val Val
            20                  25                  30

Pro Glu Ala Ile Glu Lys Ala Ile Glu Asp Lys Phe Leu Ala Glu Gly
        35                  40                  45

His Pro Cys Asn Leu Gly Leu Ile Phe Ala Ala Gly Gln Gly Asp Ala
    50                  55                  60

Lys Glu Lys Ala Ile Asn Arg Leu Ala His Glu Gly Leu Val Ser Ser
65                  70                  75                  80

Ala Ile Gly Gly His Trp Gly Leu Ile Pro Gly Leu Gln Arg Leu Ala
                85                  90                  95

Ser Glu Gly Lys Ile Thr Gly Tyr Asn Leu Pro Gln Gly Val Ile Cys
            100                 105                 110

His Leu Leu Arg Asp Ser Ala Ala Gly Lys Ala Gly Thr Leu Thr His
        115                 120                 125

Val Gly Leu Gly Thr Phe Val Asp Pro Arg Ile Glu Gly Gly Lys Ile
    130                 135                 140

Asn Ala Lys Thr Thr Glu Asp Ile Val Thr Tyr Ile Asn Ile Asn Asp
145                 150                 155                 160

Val Glu Asn Leu Leu Tyr Lys Lys Leu Asp Ala Asn Ile Ala Ile Leu
                165                 170                 175

Arg Gly Thr Thr Ala Asp Thr His Gly Asn Ile Thr Met Glu Asp Glu
            180                 185                 190

Cys Leu Ile Leu Glu Asn Leu Ala Ala Ala Gln Leu Val His Asn Gln
        195                 200                 205

Gly Gly Lys Val Ile Val Gln Val Lys Arg Ile Val Pro Lys Gly Ser
    210                 215                 220
```

Leu Asp Pro Leu Gln Val Lys Ile Pro Gly Ile Phe Val Asp Ala Leu
225                 230                 235                 240

Val Val Ala Asp Gly Glu Ala His Met Gln Thr Phe Ala Glu Ala Met
            245                 250                 255

Asn Glu Asn Tyr Val Gly Arg Gly Lys Gly Ile Arg Glu Arg Lys
        260                 265                 270

Ile Arg Pro Leu Asp Val Lys Lys Val Ile Ala Arg Arg Ala Ala Met
    275                 280                 285

Glu Leu Lys Lys Asn Ala Ile Val Asn Tyr Gly Ile Gly Ile Pro Glu
        290                 295                 300

Ile Ile Ala Gln Val Ala Asp Glu Glu Asn Val Thr Gln Glu Leu Ile
305                 310                 315                 320

Ala Thr Val Glu Pro Gly Ala Ile Gly Gly Ser Pro Ala Gly Gly Leu
            325                 330                 335

Ser Phe Gly Ala Ser Ala Phe Pro Glu Ala Ile Ile Thr Gln Asp Gln
            340                 345                 350

Met Phe Asp Phe Tyr Asp Gly Gly Gly Leu Asp Gln Ala Phe Leu Gly
            355                 360                 365

Leu Ala Glu Thr Asp Ala Lys Gly Asp Leu Asn Val Ser Lys Phe Gly
370                 375                 380

Val Lys Ile Ala Gly Cys Gly Gly Phe Ile Asn Ile Thr Gln Asn Ala
385                 390                 395                 400

Lys His Val Phe Phe Cys Gly Ser Phe Thr Ala Gly Asp Ser Asp Ile
            405                 410                 415

Ile Val Glu Glu Gly Lys Leu Ile Ile Arg Arg Asp Gly Gln Ile Lys
            420                 425                 430

Lys Phe Ile Lys His Val Gln Gln Ile Thr Phe Ser Ser Asp Thr Ala
            435                 440                 445

Arg Lys Asn His Lys Pro Val Leu Tyr Ile Thr Glu Arg Ala Val Phe
450                 455                 460

Arg Leu Ala Ala Glu Thr Ile Glu Leu Ile Glu Ile Ala Pro Gly Ile
465                 470                 475                 480

Asp Leu Gln His Asp Ile Leu Asp Lys Met Glu Phe Arg Pro Thr Ile
            485                 490                 495

Ser Pro Ala Leu Lys Glu Met Asp Lys Arg Ile Phe Ser Glu Ala Leu
            500                 505                 510

Met Ser Leu Ser Leu Lys
        515

<210> SEQ ID NO 10
<211> LENGTH: 216
<212> TYPE: PRT
<213> ORGANISM: Escherichia coli

<400> SEQUENCE: 10

Met Asp Ala Lys Gln Arg Ile Ala Arg Val Ala Gln Glu Leu Arg
1               5                   10                  15

Asp Gly Asp Ile Val Asn Leu Gly Ile Gly Leu Pro Thr Met Val Ala
            20                  25                  30

Asn Tyr Leu Pro Glu Gly Ile His Ile Thr Leu Gln Ser Glu Asn Gly
        35                  40                  45

Phe Leu Gly Leu Gly Pro Val Thr Thr Ala His Pro Asp Leu Val Asn
50                  55                  60

Ala Gly Gly Gln Pro Cys Gly Val Leu Pro Gly Ala Ala Met Phe Asp

```
                 65                  70                  75                  80
Ser Ala Met Ser Phe Ala Leu Ile Arg Gly Gly His Ile Asp Ala Cys
                     85                  90                  95

Val Leu Gly Gly Leu Gln Val Asp Glu Glu Ala Asn Leu Ala Asn Trp
                100                 105                 110

Val Val Pro Gly Lys Met Val Pro Gly Met Gly Ala Met Asp Leu
            115                 120                 125

Val Thr Gly Ser Arg Lys Val Ile Ile Ala Met Glu His Cys Ala Lys
            130                 135                 140

Asp Gly Ser Ala Lys Ile Leu Arg Arg Cys Thr Met Pro Leu Thr Ala
145                 150                 155                 160

Gln His Ala Val His Met Leu Val Thr Glu Leu Ala Val Phe Arg Phe
                165                 170                 175

Ile Asp Gly Lys Met Trp Leu Thr Glu Ile Ala Asp Gly Cys Asp Leu
            180                 185                 190

Ala Thr Val Arg Ala Lys Thr Glu Ala Arg Phe Glu Val Ala Ala Asp
            195                 200                 205

Leu Asn Thr Gln Arg Gly Asp Leu
    210                 215

<210> SEQ ID NO 11
<211> LENGTH: 220
<212> TYPE: PRT
<213> ORGANISM: Escherichia coli

<400> SEQUENCE: 11

Met Lys Thr Lys Leu Met Thr Leu Gln Asp Ala Thr Gly Phe Phe Arg
1               5                   10                  15

Asp Gly Met Thr Ile Met Val Gly Gly Phe Met Gly Ile Gly Thr Pro
                20                  25                  30

Ser Arg Leu Val Glu Ala Leu Leu Glu Ser Gly Val Arg Asp Leu Thr
            35                  40                  45

Leu Ile Ala Asn Asp Thr Ala Phe Val Asp Thr Gly Ile Gly Pro Leu
    50                  55                  60

Ile Val Asn Gly Arg Val Arg Lys Val Ile Ala Ser His Ile Gly Thr
65                  70                  75                  80

Asn Pro Glu Thr Gly Arg Arg Met Ile Ser Gly Glu Met Asp Val Val
                85                  90                  95

Leu Val Pro Gln Gly Thr Leu Ile Glu Gln Ile Arg Cys Gly Gly Ala
                100                 105                 110

Gly Leu Gly Gly Phe Leu Thr Pro Thr Gly Val Gly Thr Val Val Glu
            115                 120                 125

Glu Gly Lys Gln Thr Leu Thr Leu Asp Gly Lys Thr Trp Leu Leu Glu
            130                 135                 140

Arg Pro Leu Arg Ala Asp Leu Ala Leu Ile Arg Ala His Arg Cys Asp
145                 150                 155                 160

Thr Leu Gly Asn Leu Thr Tyr Gln Leu Ser Ala Arg Asn Phe Asn Pro
                165                 170                 175

Leu Ile Ala Leu Ala Ala Asp Ile Thr Leu Val Glu Pro Asp Glu Leu
            180                 185                 190

Val Glu Thr Gly Glu Leu Gln Pro Asp His Ile Val Thr Pro Gly Ala
            195                 200                 205

Val Ile Asp His Ile Ile Val Ser Gln Glu Ser Lys
    210                 215                 220
```

```
<210> SEQ ID NO 12
<211> LENGTH: 230
<212> TYPE: PRT
<213> ORGANISM: Pseudomonas putida

<400> SEQUENCE: 12

Met Ile Asn Lys Thr Tyr Glu Ser Ile Ala Ser Val Glu Gly Ile
1               5                   10                  15

Thr Asp Gly Ser Thr Ile Met Val Gly Gly Phe Gly Thr Ala Gly Met
                20                  25                  30

Pro Ser Glu Leu Ile Asp Ala Leu Ile Asp Thr Gly Thr Arg Asp Leu
            35                  40                  45

Thr Ile Ile Ser Asn Asn Ala Gly Asn Gly Glu Ile Gly Leu Ala Ala
    50                  55                  60

Leu Leu Lys Ala Gly Ser Val Arg Lys Val Cys Ser Phe Pro Arg
65                  70                  75                  80

Gln Ser Asp Ser Tyr Val Phe Asp Glu Leu Tyr Arg Ala Gly Lys Ile
                85                  90                  95

Glu Leu Glu Val Val Pro Gln Gly Asn Leu Ala Glu Arg Ile Arg Ala
            100                 105                 110

Ala Gly Ser Gly Ile Gly Ala Phe Phe Ser Pro Thr Gly Tyr Gly Thr
        115                 120                 125

Leu Leu Ser Glu Gly Lys Glu Thr Arg Glu Ile Asp Gly Arg Gln Tyr
    130                 135                 140

Val Leu Glu Met Pro Leu His Ala Asp Phe Ala Leu Ile Lys Ala Tyr
145                 150                 155                 160

Lys Gly Asp Arg Trp Gly Asn Leu Ile Tyr Arg Lys Ala Ala Arg Asn
                165                 170                 175

Phe Gly Pro Ile Met Ala Met Ala Ala Lys Thr Ala Ile Ala Gln Val
            180                 185                 190

Asp Gln Ile Val Glu Leu Gly Glu Leu Asp Pro Glu His Ile Ile Thr
        195                 200                 205

Pro Gly Ile Phe Val Gln Arg Val Val Ala Val Thr Gly Ala Ala Ser
    210                 215                 220

Ser Ile Ala Asn Ala Val
225                 230

<210> SEQ ID NO 13
<211> LENGTH: 213
<212> TYPE: PRT
<213> ORGANISM: Pseudomonas putida

<400> SEQUENCE: 13

Met Thr Ile Thr Thr Lys Leu Ser Arg Thr Gln Met Ala Gln Arg Val
1               5                   10                  15

Ala Ala Asp Ile Gln Glu Gly Ala Tyr Val Asn Leu Gly Ile Gly Ala
                20                  25                  30

Pro Thr Leu Val Ala Asn Phe Leu Gly Asp Lys Glu Val Phe Leu His
            35                  40                  45

Ser Glu Asn Gly Leu Leu Gly Met Gly Pro Ser Pro Ala Pro Gly Glu
    50                  55                  60

Glu Asp Asp Asp Leu Ile Asn Ala Gly Lys Gln His Val Thr Leu Leu
65                  70                  75                  80

Thr Gly Gly Ala Phe Phe His His Ala Asp Ser Phe Ser Met Met Arg
                85                  90                  95
```

```
Gly Gly His Leu Asp Ile Ala Val Leu Gly Ala Phe Gln Val Ser Val
            100                 105                 110

Lys Gly Asp Leu Ala Asn Trp His Thr Gly Ala Glu Gly Ser Ile Pro
        115                 120                 125

Ala Val Gly Gly Ala Met Asp Leu Ala Thr Gly Ala Arg Gln Val Phe
    130                 135                 140

Val Met Met Asp His Leu Thr Lys Ser Gly Glu Ser Lys Ile Val Pro
145                 150                 155                 160

Glu Cys Thr Tyr Pro Leu Thr Gly Ile Gly Cys Val Ser Arg Ile Tyr
                165                 170                 175

Thr Asp Leu Ala Val Leu Glu Val Thr Ser Asp Gly Leu Lys Val Val
            180                 185                 190

Glu Ile Cys Ala Asp Ile Asp Phe Asp Glu Leu Gln Lys Leu Ser Gly
        195                 200                 205

Val Pro Leu Ile Lys
    210

<210> SEQ ID NO 14
<211> LENGTH: 246
<212> TYPE: PRT
<213> ORGANISM: Chromobacterium violaceum

<400> SEQUENCE: 14

Met Lys Gln Gln Glu Val Arg Gln Arg Ala Phe Ala Met Pro Leu Thr
1               5                   10                  15

Ser Pro Ala Phe Pro Gly Pro Tyr Arg Phe Val Asn Arg Glu Tyr
            20                  25                  30

Met Ile Ile Thr Tyr Arg Thr Asp Pro Ala Ala Ile Glu Ala Val Leu
            35                  40                  45

Pro Glu Pro Leu Gln Met Ala Glu Pro Val Val Arg Tyr Glu Phe Ile
    50                  55                  60

Arg Met Pro Asp Ser Thr Gly Phe Gly Asp Tyr Ser Glu Ser Gly Gln
65                  70                  75                  80

Val Ile Pro Val Thr Phe Arg Gly Glu Arg Gly Ser Tyr Thr Leu Ala
                85                  90                  95

Met Phe Leu Asp Asp Gln Pro Pro Leu Ala Gly Gly Arg Glu Leu Trp
            100                 105                 110

Gly Phe Pro Lys Lys Ala Gly Lys Pro Arg Leu Glu Val His Gln Asp
        115                 120                 125

Thr Leu Val Gly Ser Leu Asp Phe Gly Pro Val Arg Ile Ala Thr Gly
    130                 135                 140

Thr Met Gly Tyr Lys Tyr Glu Ala Leu Asp Arg Ser Ala Leu Leu Ala
145                 150                 155                 160

Ser Leu Ala Glu Pro Asn Phe Leu Leu Lys Ile Ile Pro His Val Asp
                165                 170                 175

Gly Ser Pro Arg Ile Cys Glu Leu Val Arg Tyr His Thr Thr Asp Val
            180                 185                 190

Ala Ile Lys Gly Ala Trp Ser Ala Pro Gly Ser Leu Glu Leu His Pro
        195                 200                 205

His Ala Leu Ala Pro Val Ala Ala Leu Pro Val Leu Glu Val Leu Ser
    210                 215                 220

Ala Arg His Phe Val Cys Asp Leu Thr Leu Asp Leu Gly Thr Val Val
225                 230                 235                 240

Phe Asp Tyr Leu Arg Gln
                245
```

<210> SEQ ID NO 15
<211> LENGTH: 244
<212> TYPE: PRT
<213> ORGANISM: Clostridium acetobutylicum

<400> SEQUENCE: 15

Met Leu Lys Asp Glu Val Ile Lys Gln Ile Ser Thr Pro Leu Thr Ser
1               5                   10                  15

Pro Ala Phe Pro Arg Gly Pro Tyr Lys Phe His Asn Arg Glu Tyr Phe
            20                  25                  30

Asn Ile Val Tyr Arg Thr Asp Met Asp Ala Leu Arg Lys Val Val Pro
        35                  40                  45

Glu Pro Leu Glu Ile Asp Glu Pro Leu Val Arg Phe Glu Ile Met Ala
    50                  55                  60

Met His Asp Thr Ser Gly Leu Gly Cys Tyr Thr Glu Ser Gly Gln Ala
65                  70                  75                  80

Ile Pro Val Ser Phe Asn Gly Val Lys Gly Asp Tyr Leu His Met Met
                85                  90                  95

Tyr Leu Asp Asn Glu Pro Ala Ile Ala Val Gly Arg Glu Leu Ser Ala
            100                 105                 110

Tyr Pro Lys Lys Leu Gly Tyr Pro Lys Leu Phe Val Asp Ser Asp Thr
        115                 120                 125

Leu Val Gly Thr Leu Asp Tyr Gly Lys Leu Arg Val Ala Thr Ala Thr
    130                 135                 140

Met Gly Tyr Lys His Lys Ala Leu Asp Ala Asn Glu Ala Lys Asp Gln
145                 150                 155                 160

Ile Cys Arg Pro Asn Tyr Met Leu Lys Ile Ile Pro Asn Tyr Asp Gly
                165                 170                 175

Ser Pro Arg Ile Cys Glu Leu Ile Asn Ala Lys Ile Thr Asp Val Thr
            180                 185                 190

Val His Glu Ala Trp Thr Gly Pro Thr Arg Leu Gln Leu Phe Asp His
        195                 200                 205

Ala Met Ala Pro Leu Asn Asp Leu Pro Val Lys Glu Ile Val Ser Ser
    210                 215                 220

Ser His Ile Leu Ala Asp Ile Ile Leu Pro Arg Ala Glu Val Ile Tyr
225                 230                 235                 240

Asp Tyr Leu Lys

<210> SEQ ID NO 16
<211> LENGTH: 366
<212> TYPE: PRT
<213> ORGANISM: Nocardia rhamnosiphila

<400> SEQUENCE: 16

Met Arg Ile Arg Gly Ala Val Leu Glu Arg Ile Gly Ala Pro Val Pro
1               5                   10                  15

Tyr Ala Glu Ser Ala Pro Ile Thr Ile Ser Glu Leu Glu Leu Ala Asp
            20                  25                  30

Pro Gly Pro Gly Glu Ile Leu Val Arg Ile Glu Ala Ala Gly Leu Cys
        35                  40                  45

His Ser Asp Leu Ser Val Val Asp Gly Asn Arg Val Arg Pro Val Pro
    50                  55                  60

Met Leu Leu Gly His Glu Ala Ser Gly Lys Val Val Gln Ala Gly Pro
65                  70                  75                  80

-continued

Gly Val Asp Leu Pro Val Gly Arg Arg Val Ala Met Thr Phe Leu Pro
                85                  90                  95

Arg Cys Gly Glu Cys Ala Gly Cys Ala Ser Gly Gly Arg Thr Pro Cys
            100                 105                 110

Ile Pro Gly Ser Ala Ala Asn Asn Ala Gly Glu Leu Leu Gly Gly Gly
            115                 120                 125

Arg Arg Leu His Arg Asp Gly Ala Glu Val Gln His His Leu Gly Val
        130                 135                 140

Ser Gly Phe Ala Thr His Ala Val Val Asp Arg Ser Val Val Pro
145                 150                 155                 160

Val Asp Asp Val Pro Pro Glu Val Ala Val Leu Gly Cys Ala
                165                 170                 175

Val Leu Thr Gly Gly Ala Leu Leu Asn Ser Ala Lys Pro Ala Ala
            180                 185                 190

Thr Asp Arg Val Met Val Val Gly Leu Gly Gly Val Gly Met Ala Ala
        195                 200                 205

Val Leu Val Ala Val Ser Leu Gly Val Arg Glu Val Ile Ala Val Asp
        210                 215                 220

Thr Val Pro Asp Lys Leu Ala Leu Ala Arg Glu Leu Gly Ala Gly Ser
225                 230                 235                 240

Ala His Thr Pro Ala Glu Val Ala Asp Arg Gly Val Gln Ala Glu Val
                245                 250                 255

Val Val Glu Ala Val Gly Ser Ala Arg Ala Phe Glu Ser Ala Val Ala
            260                 265                 270

Ala Thr Ala Pro Gly Val Thr Val Thr Val Gly Leu Pro Ala Pro
            275                 280                 285

Asp Ala Arg Ala Thr Ile Ser Pro Leu Gly Leu Val Ala Gln Gly Arg
        290                 295                 300

Ser Ile Val Gly Ser Tyr Leu Gly Ser Ala Val Pro Ser Arg Asp Ile
305                 310                 315                 320

Pro Glu Tyr Val Arg Met Trp Arg Glu Gly Arg Leu Pro Val Glu Lys
                325                 330                 335

Leu Ile Ser Ala Arg Ile Gly Leu Ala Asp Ile Asn Gly Ala Met Asp
            340                 345                 350

Glu Leu Ala Ala Gly His Ala Leu Arg Gln Val Ile Met Phe
        355                 360                 365

<210> SEQ ID NO 17
<211> LENGTH: 348
<212> TYPE: PRT
<213> ORGANISM: Rhodococcus sp.

<400> SEQUENCE: 17

Met Lys Ala Ile Gln Tyr Thr Arg Ile Gly Ala Glu Pro Glu Leu Thr
1               5                   10                  15

Glu Ile Pro Lys Pro Glu Pro Gly Pro Gly Glu Val Leu Leu Glu Val
            20                  25                  30

Thr Ala Ala Gly Val Cys His Ser Asp Asp Phe Ile Met Ser Leu Pro
        35                  40                  45

Glu Glu Gln Tyr Thr Tyr Gly Leu Pro Leu Thr Leu Gly His Glu Gly
    50                  55                  60

Ala Gly Lys Val Ala Ala Val Gly Glu Gly Val Glu Gly Leu Asp Ile
65                  70                  75                  80

Gly Thr Asn Val Val Val Tyr Gly Pro Trp Gly Cys Gly Asn Cys Trp
                85                  90                  95

His Cys Ser Gln Gly Leu Glu Asn Tyr Cys Ser Arg Ala Gln Glu Leu
            100                 105                 110

Gly Ile Asn Pro Pro Gly Leu Gly Ala Pro Gly Ala Leu Ala Glu Phe
        115                 120                 125

Met Ile Val Asp Ser Pro Arg His Leu Val Pro Ile Gly Asp Leu Asp
130                 135                 140

Pro Val Lys Thr Val Pro Leu Thr Asp Ala Gly Leu Thr Pro Tyr His
145                 150                 155                 160

Ala Ile Lys Arg Ser Leu Pro Lys Leu Arg Gly Gly Ser Tyr Ala Val
                165                 170                 175

Val Ile Gly Thr Gly Gly Leu Gly His Val Ala Ile Gln Leu Leu Arg
            180                 185                 190

His Leu Ser Ala Ala Thr Val Ile Ala Leu Asp Val Ser Ala Asp Lys
        195                 200                 205

Leu Glu Leu Ala Thr Lys Val Gly Ala His Glu Val Val Leu Ser Asp
    210                 215                 220

Lys Asp Ala Ala Glu Asn Val Arg Lys Ile Thr Gly Ser Gln Gly Ala
225                 230                 235                 240

Ala Leu Val Leu Asp Phe Val Gly Tyr Gln Pro Thr Ile Asp Thr Ala
                245                 250                 255

Met Ala Val Ala Gly Val Gly Ser Asp Val Thr Ile Val Gly Ile Gly
            260                 265                 270

Asp Gly Gln Ala His Ala Lys Val Gly Phe Phe Gln Ser Pro Tyr Glu
        275                 280                 285

Ala Ser Val Thr Val Pro Tyr Trp Gly Ala Arg Asn Glu Leu Ile Glu
    290                 295                 300

Leu Ile Asp Leu Ala His Ala Gly Ile Phe Asp Ile Ala Val Glu Thr
305                 310                 315                 320

Phe Ser Leu Asp Asn Gly Ala Glu Ala Tyr Arg Arg Leu Ala Ala Gly
                325                 330                 335

Thr Leu Ser Gly Arg Ala Val Val Val Pro Gly Leu
            340                 345

<210> SEQ ID NO 18
<211> LENGTH: 397
<212> TYPE: PRT
<213> ORGANISM: Castellaniella defragrans

<400> SEQUENCE: 18

Met Arg Phe Thr Leu Lys Thr Thr Ala Ile Val Ser Ala Ala Ala Leu
1               5                   10                  15

Leu Ala Gly Phe Gly Pro Pro Arg Ala Ala Glu Leu Pro Pro Gly
            20                  25                  30

Arg Leu Ala Thr Thr Glu Asp Tyr Phe Ala Gln Gln Ala Lys Gln Ala
        35                  40                  45

Val Thr Pro Asp Val Met Ala Gln Leu Ala Tyr Met Asn Tyr Ile Asp
    50                  55                  60

Phe Ile Ser Pro Phe Tyr Ser Arg Gly Cys Ser Phe Glu Ala Trp Glu
65                  70                  75                  80

Leu Lys His Thr Pro Gln Arg Val Ile Lys Tyr Ser Ile Ala Phe Tyr
                85                  90                  95

Ala Tyr Gly Leu Ala Ser Val Ala Leu Ile Asp Pro Lys Leu Arg Ala
            100                 105                 110

Leu Ala Gly His Asp Leu Asp Ile Ala Val Ser Lys Met Lys Cys Lys

-continued

```
        115                 120                 125

Arg Val Trp Gly Asp Trp Glu Glu Asp Gly Phe Gly Thr Asp Pro Ile
    130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Arg Tyr Glu Ala Glu His Ala
                165                 170                 175

His Leu Thr Arg Ile Ile His Asp Glu Ile Ala Ala Asn Pro Phe Ala
            180                 185                 190

Gly Ile Val Cys Glu Pro Asp Asn Tyr Phe Val Gln Cys Asn Ser Val
        195                 200                 205

Ala Tyr Leu Ser Leu Trp Val Tyr Asp Arg Leu His Gly Thr Asp Tyr
    210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
                245                 250                 255

Ala Val Lys Pro Trp Ile Ser Ala Tyr Thr Thr Ala Trp Thr Leu Ala
            260                 265                 270

Met Val His Gly Met Asp Pro Ala Phe Ser Glu Arg Tyr Tyr Pro Arg
        275                 280                 285

Phe Lys Gln Thr Phe Val Glu Val Tyr Asp Glu Gly Arg Lys Ala Arg
    290                 295                 300

Val Arg Glu Thr Ala Gly Thr Asp Asp Ala Asp Gly Gly Val Gly Leu
305                 310                 315                 320

Ala Ser Ala Phe Thr Leu Leu Leu Ala Arg Glu Met Gly Asp Gln Gln
                325                 330                 335

Leu Phe Asp Gln Leu Leu Asn His Leu Glu Pro Pro Ala Lys Pro Ser
            340                 345                 350

Ile Val Ser Ala Ser Leu Arg Tyr Glu His Pro Gly Ser Leu Leu Phe
        355                 360                 365

Asp Glu Leu Leu Phe Leu Ala Lys Val His Ala Gly Phe Gly Ala Leu
    370                 375                 380

Leu Arg Met Pro Pro Pro Ala Ala Lys Leu Ala Gly Lys
385                 390                 395

<210> SEQ ID NO 19
<211> LENGTH: 438
<212> TYPE: PRT
<213> ORGANISM: Clostridium aminobutyricum

<400> SEQUENCE: 19

Met Asp Trp Lys Lys Ile Tyr Glu Asp Arg Thr Cys Thr Ala Asp Glu
1               5                   10                  15

Ala Val Lys Ser Ile Lys Ser Gly Asp Arg Val Leu Phe Ala His Cys
            20                  25                  30

Val Ala Glu Pro Pro Val Leu Val Glu Ala Met Val Ala Asn Ala Ala
        35                  40                  45

Ala Tyr Lys Asn Val Thr Val Ser His Met Val Thr Leu Gly Lys Gly
    50                  55                  60

Glu Tyr Ser Lys Pro Glu Tyr Lys Glu Asn Phe Thr Phe Glu Gly Trp
65                  70                  75                  80

Phe Thr Ser Pro Ser Thr Arg Gly Ser Ile Ala Glu Gly His Gly Gln
                85                  90                  95
```

Phe Val Pro Val Phe His Glu Val Pro Ser Leu Ile Arg Lys Asp
            100                 105                 110

Ile Phe His Val Asp Val Phe Met Val Met Val Ser Pro Pro Asp His
        115                 120                 125

Asn Gly Phe Cys Cys Val Gly Val Ser Ser Asp Tyr Thr Met Gln Ala
    130                 135                 140

Ile Lys Ser Ala Lys Ile Val Leu Ala Glu Val Asn Asp Gln Val Pro
145                 150                 155                 160

Val Val Tyr Gly Asp Thr Phe Val His Val Ser Glu Ile Asp Lys Phe
                165                 170                 175

Val Glu Thr Ser His Pro Leu Pro Glu Ile Gly Leu Pro Lys Ile Gly
            180                 185                 190

Glu Val Glu Ala Ala Ile Gly Lys His Cys Ala Ser Leu Ile Glu Asp
        195                 200                 205

Gly Ser Thr Leu Gln Leu Gly Ile Gly Ala Ile Pro Asp Ala Val Leu
    210                 215                 220

Ser Gln Leu Lys Asp Lys Lys His Leu Gly Ile His Ser Glu Met Ile
225                 230                 235                 240

Ser Asp Gly Val Val Asp Leu Tyr Glu Ala Gly Val Ile Asp Cys Ser
                245                 250                 255

Gln Lys Ser Ile Asp Lys Gly Lys Met Ala Ile Thr Phe Leu Met Gly
            260                 265                 270

Thr Lys Arg Leu Tyr Asp Phe Ala Ala Asn Asn Pro Lys Val Glu Leu
        275                 280                 285

Lys Pro Val Asp Tyr Ile Asn His Pro Ser Val Val Ala Gln Cys Ser
290                 295                 300

Lys Met Val Cys Ile Asn Ala Cys Leu Gln Val Asp Phe Met Gly Gln
305                 310                 315                 320

Ile Val Ser Asp Ser Ile Gly Thr Lys Gln Phe Ser Val Gly Gly
                325                 330                 335

Gln Val Asp Phe Val Arg Gly Ala Ser Met Ser Ile Asp Gly Lys Gly
            340                 345                 350

Lys Ala Ile Ile Ala Met Pro Ser Val Ala Lys Lys Asp Gly Ser
        355                 360                 365

Met Ile Ser Lys Ile Val Pro Phe Ile Asp His Gly Ala Ala Val Thr
    370                 375                 380

Thr Ser Arg Asn Asp Ala Asp Tyr Val Val Thr Glu Tyr Gly Ile Ala
385                 390                 395                 400

Glu Met Lys Gly Lys Ser Leu Gln Asp Arg Ala Arg Ala Leu Ile Asn
                405                 410                 415

Ile Ala His Pro Asp Phe Lys Asp Glu Leu Lys Ala Glu Phe Glu Lys
            420                 425                 430

Arg Phe Asn Ala Ala Phe
        435

<210> SEQ ID NO 20
<211> LENGTH: 279
<212> TYPE: PRT
<213> ORGANISM: Candida parapsilosis

<400> SEQUENCE: 20

Met Gly Glu Ile Glu Ser Tyr Cys Asn Lys Glu Leu Gly Pro Leu Pro
1               5                   10                  15

Thr Lys Ala Pro Thr Leu Ser Lys Asn Val Leu Asp Leu Phe Ser Leu
            20                  25                  30

-continued

```
Lys Gly Lys Val Ala Ser Val Thr Gly Ser Ser Gly Ile Gly Trp
        35                  40                  45

Ala Val Ala Glu Ala Tyr Ala Gln Ala Gly Ala Asp Val Ala Ile Trp
    50                  55                  60

Tyr Asn Ser His Pro Ala Asp Glu Lys Ala Glu His Leu Gln Lys Thr
65                  70                  75                  80

Tyr Gly Val His Ser Lys Ala Tyr Lys Cys Asn Ile Ser Asp Pro Lys
                85                  90                  95

Ser Val Glu Glu Thr Ile Ser Gln Gln Glu Lys Asp Phe Gly Thr Ile
            100                 105                 110

Asp Val Phe Val Ala Asn Ala Gly Val Thr Trp Thr Gln Gly Pro Glu
        115                 120                 125

Ile Asp Val Asp Asn Tyr Asp Ser Trp Asn Lys Ile Ile Ser Val Asp
    130                 135                 140

Leu Asn Gly Val Tyr Tyr Cys Ser His Asn Ile Gly Lys Ile Phe Lys
145                 150                 155                 160

Lys Asn Gly Lys Gly Ser Leu Ile Ile Thr Ser Ser Ile Ser Gly Lys
                165                 170                 175

Ile Val Asn Ile Pro Gln Leu Gln Ala Pro Tyr Asn Thr Ala Lys Ala
            180                 185                 190

Ala Cys Thr His Leu Ala Lys Ser Leu Ala Ile Glu Trp Ala Pro Phe
        195                 200                 205

Ala Arg Val Asn Thr Ile Ser Pro Gly Tyr Ile Asp Thr Asp Ile Thr
    210                 215                 220

Asp Phe Ala Ser Lys Asp Met Lys Ala Lys Trp Gln Leu Thr Pro
225                 230                 235                 240

Leu Gly Arg Glu Gly Leu Thr Gln Glu Leu Val Gly Gly Tyr Leu Tyr
                245                 250                 255

Leu Ala Ser Asn Ala Ser Thr Phe Thr Thr Gly Ser Asp Val Val Ile
            260                 265                 270

Asp Gly Gly Tyr Thr Cys Pro
        275

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 21

His His His His His His
1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Gly His His His His His His Ser Ser Gly Leu Val Pro Arg Gly
1               5                   10                  15

Ser
```

```
<210> SEQ ID NO 23
<211> LENGTH: 526
<212> TYPE: PRT
<213> ORGANISM: Escherichia coli
<220> FEATURE:
<221> NAME/KEY: MOD_RES
<222> LOCATION: (274)..(280)
<223> OTHER INFORMATION: Any amino acid
<220> FEATURE:
<221> NAME/KEY: MOD_RES
<222> LOCATION: (339)..(345)
<223> OTHER INFORMATION: Any amino acid

<400> SEQUENCE: 23

Val Lys Pro Pro Arg Ile Asn Gly Arg Val Pro Val Leu Ser Ala Gln
1               5                   10                  15

Glu Ala Val Asn Tyr Ile Pro Asp Glu Ala Thr Leu Cys Val Leu Gly
            20                  25                  30

Ala Gly Gly Gly Ile Leu Glu Ala Thr Thr Leu Ile Thr Ala Leu Ala
        35                  40                  45

Asp Lys Tyr Lys Gln Thr Gln Thr Pro Arg Asn Leu Ser Ile Ile Ser
    50                  55                  60

Pro Thr Gly Leu Gly Asp Arg Ala Asp Arg Gly Ile Ser Pro Leu Ala
65                  70                  75                  80

Gln Glu Gly Leu Val Lys Trp Ala Leu Cys Gly His Trp Gly Gln Ser
                85                  90                  95

Pro Arg Ile Ser Asp Leu Ala Glu Gln Asn Lys Ile Ile Ala Tyr Asn
            100                 105                 110

Tyr Pro Gln Gly Val Leu Thr Gln Thr Leu Arg Ala Ala Ala Ala His
        115                 120                 125

Gln Pro Gly Ile Ile Ser Asp Ile Gly Ile Gly Thr Phe Val Asp Pro
    130                 135                 140

Arg Gln Gln Gly Gly Lys Leu Asn Glu Val Thr Lys Glu Asp Leu Ile
145                 150                 155                 160

Lys Leu Val Glu Phe Asp Asn Lys Glu Tyr Leu Tyr Lys Ala Ile
                165                 170                 175

Ala Pro Asp Ile Ala Phe Ile Arg Ala Thr Thr Cys Asp Ser Glu Gly
            180                 185                 190

Tyr Ala Thr Phe Glu Asp Glu Val Met Tyr Leu Asp Ala Leu Val Ile
        195                 200                 205

Ala Gln Ala Val His Asn Asn Gly Gly Ile Val Met Met Gln Val Gln
    210                 215                 220

Lys Met Val Lys Lys Ala Thr Leu His Pro Lys Ser Val Arg Ile Pro
225                 230                 235                 240

Gly Tyr Leu Val Asp Ile Val Val Asp Pro Asp Gln Ser Gln Leu
                245                 250                 255

Tyr Gly Gly Ala Pro Val Asn Arg Phe Ile Ser Gly Asp Phe Thr Leu
            260                 265                 270

Asp Xaa Xaa Xaa Xaa Xaa Xaa Pro Leu Asn Gln Arg Lys Leu Val
    275                 280                 285

Ala Arg Arg Ala Leu Phe Glu Met Arg Lys Gly Ala Val Gly Asn Val
290                 295                 300

Gly Val Gly Ile Ala Asp Gly Ile Gly Leu Val Ala Arg Glu Glu Gly
305                 310                 315                 320

Cys Ala Asp Asp Phe Ile Leu Thr Val Glu Thr Gly Pro Ile Gly Gly
                325                 330                 335
```

-continued

```
Ile Thr Xaa Xaa Xaa Xaa Xaa Xaa Ala Asn Val Asn Thr Arg Ala
            340                 345                 350

Ile Leu Asp Met Thr Ser Gln Phe Asp Phe Tyr His Gly Gly Gly Leu
            355                 360                 365

Asp Val Cys Tyr Leu Ser Phe Ala Glu Val Asp Gln His Gly Asn Val
        370                 375                 380

Gly Val His Lys Phe Asn Gly Lys Ile Met Gly Thr Gly Gly Phe Ile
385                 390                 395                 400

Asp Ile Ser Ala Thr Ser Lys Lys Ile Ile Phe Cys Gly Thr Leu Thr
                405                 410                 415

Ala Gly Ser Leu Lys Thr Glu Ile Ala Asp Gly Lys Leu Asn Ile Val
            420                 425                 430

Gln Glu Gly Arg Val Lys Lys Phe Ile Arg Glu Leu Pro Glu Ile Thr
        435                 440                 445

Phe Ser Gly Lys Ile Ala Leu Glu Arg Gly Leu Asp Val Arg Tyr Ile
    450                 455                 460

Thr Glu Arg Ala Val Phe Thr Leu Lys Glu Asp Gly Leu His Leu Ile
465                 470                 475                 480

Glu Ile Ala Pro Gly Val Asp Leu Gln Lys Asp Ile Leu Asp Lys Met
                485                 490                 495

Asp Phe Thr Pro Val Ile Ser Pro Glu Leu Lys Leu Met Asp Glu Arg
            500                 505                 510

Leu Phe Ile Asp Ala Ala Met Gly Phe Val Leu Pro Glu Ala
        515                 520                 525
```

<210> SEQ ID NO 24
<211> LENGTH: 526
<212> TYPE: PRT
<213> ORGANISM: Escherichia coli
<220> FEATURE:
<221> NAME/KEY: MOD_RES
<222> LOCATION: (201)..(201)
<223> OTHER INFORMATION: Any amino acid
<220> FEATURE:
<221> NAME/KEY: MOD_RES
<222> LOCATION: (220)..(221)
<223> OTHER INFORMATION: Any amino acid
<220> FEATURE:
<221> NAME/KEY: MOD_RES
<222> LOCATION: (226)..(226)
<223> OTHER INFORMATION: Any amino acid
<220> FEATURE:
<221> NAME/KEY: MOD_RES
<222> LOCATION: (296)..(296)
<223> OTHER INFORMATION: Any amino acid
<220> FEATURE:
<221> NAME/KEY: MOD_RES
<222> LOCATION: (356)..(356)
<223> OTHER INFORMATION: Any amino acid
<220> FEATURE:
<221> NAME/KEY: MOD_RES
<222> LOCATION: (394)..(394)
<223> OTHER INFORMATION: Any amino acid
<220> FEATURE:
<221> NAME/KEY: MOD_RES
<222> LOCATION: (496)..(496)
<223> OTHER INFORMATION: Any amino acid
<220> FEATURE:
<221> NAME/KEY: MOD_RES
<222> LOCATION: (509)..(509)
<223> OTHER INFORMATION: Any amino acid
<220> FEATURE:
<221> NAME/KEY: MOD_RES
<222> LOCATION: (519)..(519)
<223> OTHER INFORMATION: Any amino acid

<400> SEQUENCE: 24

```
Val Lys Pro Pro Arg Ile Asn Gly Arg Val Pro Val Leu Ser Ala Gln
1               5                   10                  15

Glu Ala Val Asn Tyr Ile Pro Asp Glu Ala Thr Leu Cys Val Leu Gly
                20                  25                  30

Ala Gly Gly Ile Leu Glu Ala Thr Thr Leu Ile Thr Ala Leu Ala
            35                  40                  45

Asp Lys Tyr Lys Gln Thr Gln Thr Pro Arg Asn Leu Ser Ile Ile Ser
    50                  55                  60

Pro Thr Gly Leu Gly Asp Arg Ala Asp Arg Gly Ile Ser Pro Leu Ala
65                  70                  75                  80

Gln Glu Gly Leu Val Lys Trp Ala Leu Cys Gly His Trp Gly Gln Ser
                85                  90                  95

Pro Arg Ile Ser Asp Leu Ala Glu Gln Asn Lys Ile Ile Ala Tyr Asn
                100                 105                 110

Tyr Pro Gln Gly Val Leu Thr Gln Thr Leu Arg Ala Ala Ala His
        115                 120                 125

Gln Pro Gly Ile Ile Ser Asp Ile Gly Ile Gly Thr Phe Val Asp Pro
    130                 135                 140

Arg Gln Gln Gly Gly Lys Leu Asn Glu Val Thr Lys Glu Asp Leu Ile
145                 150                 155                 160

Lys Leu Val Glu Phe Asp Asn Lys Glu Tyr Leu Tyr Tyr Lys Ala Ile
                165                 170                 175

Ala Pro Asp Ile Ala Phe Ile Arg Ala Thr Thr Cys Asp Ser Glu Gly
                180                 185                 190

Tyr Ala Thr Phe Glu Asp Glu Val Xaa Tyr Leu Asp Ala Leu Val Ile
        195                 200                 205

Ala Gln Ala Val His Asn Asn Gly Gly Ile Val Xaa Xaa Gln Val Gln
    210                 215                 220

Lys Xaa Val Lys Lys Ala Thr Leu His Pro Lys Ser Val Arg Ile Pro
225                 230                 235                 240

Gly Tyr Leu Val Asp Ile Val Val Asp Pro Asp Gln Ser Gln Leu
            245                 250                 255

Tyr Gly Gly Ala Pro Val Asn Arg Phe Ile Ser Gly Asp Phe Thr Leu
        260                 265                 270

Asp Asp Ser Thr Lys Leu Ser Leu Pro Leu Asn Gln Arg Lys Leu Val
        275                 280                 285

Ala Arg Arg Ala Leu Phe Glu Xaa Arg Lys Gly Ala Val Gly Asn Val
    290                 295                 300

Gly Val Gly Ile Ala Asp Gly Ile Gly Leu Val Ala Arg Glu Glu Gly
305                 310                 315                 320

Cys Ala Asp Asp Phe Ile Leu Thr Val Glu Thr Gly Pro Ile Gly Gly
                325                 330                 335

Ile Thr Ser Gln Gly Ile Ala Phe Gly Ala Asn Val Asn Thr Arg Ala
            340                 345                 350

Ile Leu Asp Xaa Thr Ser Gln Phe Asp Phe Tyr His Gly Gly Leu
            355                 360                 365

Asp Val Cys Tyr Leu Ser Phe Ala Glu Val Asp Gln His Gly Asn Val
    370                 375                 380

Gly Val His Lys Phe Asn Gly Lys Ile Xaa Gly Thr Gly Gly Phe Ile
385                 390                 395                 400

Asp Ile Ser Ala Thr Ser Lys Lys Ile Ile Phe Cys Gly Thr Leu Thr
                405                 410                 415
```

```
Ala Gly Ser Leu Lys Thr Glu Ile Ala Asp Gly Lys Leu Asn Ile Val
            420                 425                 430

Gln Glu Gly Arg Val Lys Lys Phe Ile Arg Glu Leu Pro Glu Ile Thr
        435                 440                 445

Phe Ser Gly Lys Ile Ala Leu Glu Arg Gly Leu Asp Val Arg Tyr Ile
    450                 455                 460

Thr Glu Arg Ala Val Phe Thr Leu Lys Glu Asp Gly Leu His Leu Ile
465                 470                 475                 480

Glu Ile Ala Pro Gly Val Asp Leu Gln Lys Asp Ile Leu Asp Lys Xaa
                485                 490                 495

Asp Phe Thr Pro Val Ile Ser Pro Glu Leu Lys Leu Xaa Asp Glu Arg
            500                 505                 510

Leu Phe Ile Asp Ala Ala Xaa Gly Phe Val Leu Pro Glu Ala
        515                 520                 525

<210> SEQ ID NO 25
<211> LENGTH: 220
<212> TYPE: PRT
<213> ORGANISM: Escherichia coli

<400> SEQUENCE: 25

Met Lys Thr Lys Leu Met Thr Leu Gln Asp Ala Thr Gly Phe Phe Arg
1               5                   10                  15

Asp Gly Met Thr Ile Met Val Gly Gly Phe Met Gly Ile Gly Thr Pro
            20                  25                  30

Ser Arg Leu Val Glu Ala Leu Leu Glu Ser Gly Val Arg Asp Leu Thr
        35                  40                  45

Leu Ile Ala Asn Asp Thr Ala Phe Val Asp Thr Gly Ile Gly Pro Leu
    50                  55                  60

Ile Val Asn Gly Arg Val Arg Lys Val Ile Ala Ser His Ile Gly Thr
65                  70                  75                  80

Asn Pro Glu Thr Gly Arg Arg Met Ile Ser Gly Glu Met Asp Val Val
                85                  90                  95

Leu Val Pro Gln Gly Thr Leu Ile Glu Gln Ile Arg Cys Gly Gly Ala
            100                 105                 110

Gly Leu Gly Gly Phe Leu Thr Pro Thr Gly Val Gly Thr Val Val Glu
        115                 120                 125

Glu Gly Lys Gln Thr Leu Thr Leu Asp Gly Lys Thr Trp Leu Leu Glu
    130                 135                 140

Arg Pro Leu Arg Ala Asp Leu Ala Leu Ile Arg Ala His Arg Cys Asp
145                 150                 155                 160

Thr Leu Gly Asn Leu Thr Tyr Gln Leu Ser Ala Arg Asn Phe Asn Pro
                165                 170                 175

Leu Ile Ala Leu Ala Ala Asp Ile Thr Leu Val Glu Pro Asp Glu Leu
            180                 185                 190

Val Glu Thr Gly Glu Leu Gln Pro Asp His Ile Val Thr Pro Gly Ala
        195                 200                 205

Val Ile Asp His Ile Ile Val Ser Gln Glu Ser Lys
    210                 215                 220

<210> SEQ ID NO 26
<211> LENGTH: 475
<212> TYPE: PRT
<213> ORGANISM: Sus scrofa

<400> SEQUENCE: 26
```

```
Thr Lys Phe Tyr Thr Asp Ala Val Glu Ala Val Lys Asp Ile Pro Asn
1               5                   10                  15

Gly Ala Thr Val Leu Val Gly Gly Phe Gly Leu Cys Gly Ile Pro Glu
            20                  25                  30

Asn Leu Ile Gly Ala Leu Leu Lys Thr Gly Val Lys Glu Leu Thr Ala
                35                  40                  45

Val Ser Asn Asn Ala Gly Val Asp Asn Phe Gly Leu Gly Leu Leu Leu
    50                  55                  60

Gln Ser Lys Gln Ile Lys Arg Met Ile Ser Ser Tyr Val Gly Glu Asn
65                  70                  75                  80

Ala Glu Phe Glu Arg Gln Tyr Leu Ala Gly Glu Leu Glu Val Glu Leu
                85                  90                  95

Thr Pro Gln Gly Thr Leu Ala Glu Arg Ile Arg Ala Gly Gly Ala Gly
                100                 105                 110

Val Pro Ala Phe Tyr Thr Ser Thr Gly Tyr Gly Thr Leu Val Gln Glu
                115                 120                 125

Gly Gly Ser Pro Ile Lys Tyr Asn Lys Asp Gly Ser Ile Ala Ile Ala
            130                 135                 140

Ser Lys Pro Arg Glu Val Arg Glu Phe Asn Gly Gln His Phe Ile Leu
145                 150                 155                 160

Glu Glu Ala Ile Arg Gly Asp Phe Ala Leu Val Lys Ala Trp Lys Ala
                165                 170                 175

Asp Gln Ala Gly Asn Val Thr Phe Arg Lys Ser Ala Arg Asn Phe Asn
            180                 185                 190

Leu Pro Met Cys Lys Ala Ala Glu Thr Thr Val Val Glu Val Glu Glu
            195                 200                 205

Ile Val Asp Ile Gly Ser Phe Ala Pro Glu Asp Ile His Ile Pro Lys
            210                 215                 220

Ile Tyr Val His Arg Leu Val Lys Gly Glu Lys Tyr Glu Lys Arg Ile
225                 230                 235                 240

Glu Arg Leu Ser Val Arg Lys Glu Ser Gly Lys Leu Gly Asp Asn Val
                245                 250                 255

Arg Glu Arg Ile Ile Lys Arg Ala Ala Leu Glu Phe Glu Asp Gly Met
            260                 265                 270

Tyr Ala Asn Leu Gly Ile Gly Ile Pro Leu Leu Ala Ser Asn Phe Ile
            275                 280                 285

Ser Pro Asn Met Thr Val His Leu Gln Ser Glu Asn Gly Ile Leu Gly
            290                 295                 300

Leu Gly Pro Tyr Pro Leu Gln Asn Glu Val Asp Ala Asp Leu Ile Asn
305                 310                 315                 320

Ala Gly Lys Glu Thr Val Thr Val Leu Pro Gly Ala Ser Tyr Phe Ser
                325                 330                 335

Ser Asp Glu Ser Phe Ala Met Ile Arg Gly Gly His Val Asn Leu Thr
            340                 345                 350

Met Leu Gly Ala Met Gln Val Ser Lys Tyr Gly Asp Leu Ala Asn Trp
            355                 360                 365

Met Ile Pro Gly Lys Leu Val Lys Gly Met Gly Gly Ala Met Asp Leu
            370                 375                 380

Val Ser Ser Ala Lys Thr Lys Val Val Thr Met Glu His Ser Ala
385                 390                 395                 400

Lys Gly Asn Ala His Lys Ile Met Glu Lys Cys Thr Leu Pro Leu Thr
                405                 410                 415

Gly Lys Gln Cys Val Asn Arg Ile Ile Thr Glu Lys Ala Val Phe Asp
```

```
                420             425             430
Val Asp Arg Lys Lys Gly Leu Thr Leu Ile Glu Leu Trp Glu Gly Leu
            435                 440                 445

Thr Val Asp Asp Ile Lys Lys Ser Thr Gly Cys Asp Phe Ala Val Ser
            450                 455                 460

Pro Lys Leu Ile Pro Met Gln Gln Val Thr Thr
465                 470                 475

<210> SEQ ID NO 27
<211> LENGTH: 481
<212> TYPE: PRT
<213> ORGANISM: Sus scrofa

<400> SEQUENCE: 27

Thr Lys Phe Tyr Thr Asp Ala Val Glu Ala Val Lys Asp Ile Pro Asn
1               5                   10                  15

Gly Ala Thr Val Leu Val Gly Gly Phe Gly Leu Ala Gly Ile Pro Glu
            20                  25                  30

Asn Leu Ile Gly Ala Leu Leu Lys Thr Gly Val Lys Glu Leu Thr Ala
            35                  40                  45

Val Ser Asn Asn Ala Gly Val Asp Asn Phe Gly Leu Gly Leu Leu Leu
50                  55                  60

Gln Ser Lys Gln Ile Lys Arg Met Ile Ser Ser Tyr Val Gly Glu Asn
65                  70                  75                  80

Ala Glu Phe Glu Arg Gln Tyr Leu Ala Gly Glu Leu Glu Val Glu Leu
                85                  90                  95

Thr Pro Gln Gly Thr Leu Ala Glu Arg Ile Arg Ala Gly Gly Ala Gly
            100                 105                 110

Val Pro Ala Phe Tyr Thr Ser Thr Gly Tyr Gly Thr Leu Val Gln Glu
            115                 120                 125

Gly Gly Ser Pro Ile Lys Tyr Asn Lys Asp Gly Ser Ile Ala Ile Ala
130                 135                 140

Ser Lys Pro Arg Glu Val Arg Glu Phe Asn Gly Gln His Phe Ile Leu
145                 150                 155                 160

Glu Glu Ala Ile Arg Gly Asp Phe Ala Leu Val Lys Ala Trp Lys Ala
                165                 170                 175

Asp Gln Ala Gly Asn Val Thr Phe Arg Lys Ser Ala Arg Asn Phe Asn
            180                 185                 190

Leu Pro Met Cys Lys Ala Ala Glu Thr Thr Val Val Glu Val Glu Glu
            195                 200                 205

Ile Val Asp Ile Gly Ser Phe Ala Pro Glu Asp Ile His Ile Pro Lys
210                 215                 220

Ile Tyr Val His Arg Leu Val Lys Gly Glu Lys Tyr Glu Lys Arg Ile
225                 230                 235                 240

Glu Arg Leu Ser Val Arg Lys Glu Glu Asp Val Lys Thr Arg Ser Gly
                245                 250                 255

Lys Leu Gly Asp Asn Val Arg Glu Arg Ile Ile Lys Arg Ala Ala Leu
            260                 265                 270

Glu Phe Glu Asp Gly Met Tyr Ala Asn Leu Gly Ile Gly Ile Pro Leu
            275                 280                 285

Leu Ala Ser Asn Phe Ile Ser Pro Asn Met Thr Val His Leu Gln Ser
290                 295                 300

Glu Asn Gly Ile Leu Gly Leu Gly Pro Tyr Pro Leu Gln Asn Glu Val
305                 310                 315                 320
```

```
Asp Ala Asp Leu Ile Asn Ala Gly Lys Glu Thr Val Thr Val Leu Pro
            325                 330                 335

Gly Ala Ser Tyr Phe Ser Ser Asp Glu Ser Phe Ala Met Ile Arg Gly
        340                 345                 350

Gly His Val Asn Leu Thr Met Leu Gly Ala Met Gln Val Ser Lys Tyr
        355                 360                 365

Gly Asp Leu Ala Asn Trp Met Ile Pro Gly Lys Leu Val Lys Gly Met
370                 375                 380

Gly Gly Ala Met Asp Leu Val Ser Ser Ala Lys Thr Lys Val Val Val
385                 390                 395                 400

Thr Met Glu His Ser Ala Lys Gly Asn Ala His Lys Ile Met Glu Lys
                405                 410                 415

Cys Thr Leu Pro Leu Thr Gly Lys Gln Cys Val Asn Arg Ile Ile Thr
            420                 425                 430

Glu Lys Ala Val Phe Asp Val Asp Arg Lys Lys Gly Leu Thr Leu Ile
            435                 440                 445

Glu Leu Trp Glu Gly Leu Thr Val Asp Asp Ile Lys Lys Ser Thr Gly
            450                 455                 460

Cys Asp Phe Ala Val Ser Pro Lys Leu Ile Pro Met Gln Gln Val Thr
465                 470                 475                 480

Thr
```

<210> SEQ ID NO 28
<211> LENGTH: 481
<212> TYPE: PRT
<213> ORGANISM: Sus scrofa

<400> SEQUENCE: 28

```
Thr Lys Phe Tyr Thr Asp Ala Val Glu Ala Val Lys Asp Ile Pro Asn
1               5                   10                  15

Gly Ala Thr Val Leu Val Gly Gly Phe Gly Leu Ser Gly Ile Pro Glu
            20                  25                  30

Asn Leu Ile Gly Ala Leu Leu Lys Thr Gly Val Lys Glu Leu Thr Ala
        35                  40                  45

Val Ser Asn Asn Ala Gly Val Asp Asn Phe Gly Leu Gly Leu Leu Leu
50                  55                  60

Gln Ser Lys Gln Ile Lys Arg Met Ile Ser Ser Tyr Val Gly Glu Asn
65                  70                  75                  80

Ala Glu Phe Glu Arg Gln Tyr Leu Ala Gly Glu Leu Glu Val Glu Leu
                85                  90                  95

Thr Pro Gln Gly Thr Leu Ala Glu Arg Ile Arg Ala Gly Gly Ala Gly
            100                 105                 110

Val Pro Ala Phe Tyr Thr Ser Thr Gly Tyr Gly Thr Leu Val Gln Glu
        115                 120                 125

Gly Gly Ser Pro Ile Lys Tyr Asn Lys Asp Gly Ser Ile Ala Ile Ala
130                 135                 140

Ser Lys Pro Arg Glu Val Arg Glu Phe Asn Gly Gln His Phe Ile Leu
145                 150                 155                 160

Glu Glu Ala Ile Arg Gly Asp Phe Ala Leu Val Lys Ala Trp Lys Ala
                165                 170                 175

Asp Gln Ala Gly Asn Val Thr Phe Arg Lys Ser Ala Arg Asn Phe Asn
            180                 185                 190

Leu Pro Met Cys Lys Ala Ala Glu Thr Thr Val Val Glu Val Glu Glu
        195                 200                 205
```

```
Ile Val Asp Ile Gly Ser Phe Ala Pro Glu Asp Ile His Ile Pro Lys
    210                 215                 220

Ile Tyr Val His Arg Leu Val Lys Gly Glu Lys Tyr Glu Lys Arg Ile
225                 230                 235                 240

Glu Arg Leu Ser Val Arg Lys Glu Asp Val Lys Thr Arg Ser Gly
                245                 250                 255

Lys Leu Gly Asp Asn Val Arg Glu Arg Ile Ile Lys Arg Ala Ala Leu
            260                 265                 270

Glu Phe Glu Asp Gly Met Tyr Ala Asn Leu Gly Ile Gly Ile Pro Leu
        275                 280                 285

Leu Ala Ser Asn Phe Ile Ser Pro Asn Met Thr Val His Leu Gln Ser
    290                 295                 300

Glu Asn Gly Ile Leu Gly Leu Gly Pro Tyr Pro Leu Gln Asn Glu Val
305                 310                 315                 320

Asp Ala Asp Leu Ile Asn Ala Gly Lys Glu Thr Val Thr Val Leu Pro
                325                 330                 335

Gly Ala Ser Tyr Phe Ser Ser Asp Glu Ser Phe Ala Met Ile Arg Gly
            340                 345                 350

Gly His Val Asn Leu Thr Met Leu Gly Ala Met Gln Val Ser Lys Tyr
        355                 360                 365

Gly Asp Leu Ala Asn Trp Met Ile Pro Gly Lys Leu Val Lys Gly Met
370                 375                 380

Gly Gly Ala Met Asp Leu Val Ser Ser Ala Lys Thr Lys Val Val Val
385                 390                 395                 400

Thr Met Glu His Ser Ala Lys Gly Asn Ala His Lys Ile Met Glu Lys
                405                 410                 415

Cys Thr Leu Pro Leu Thr Gly Lys Gln Cys Val Asn Arg Ile Ile Thr
            420                 425                 430

Glu Lys Ala Val Phe Asp Val Asp Arg Lys Lys Gly Leu Thr Leu Ile
        435                 440                 445

Glu Leu Trp Glu Gly Leu Thr Val Asp Asp Ile Lys Lys Ser Thr Gly
    450                 455                 460

Cys Asp Phe Ala Val Ser Pro Lys Leu Ile Pro Met Gln Gln Val Thr
465                 470                 475                 480

Thr

<210> SEQ ID NO 29
<211> LENGTH: 489
<212> TYPE: PRT
<213> ORGANISM: Homo sapiens

<400> SEQUENCE: 29

Met Thr Lys Phe Tyr Thr Asp Pro Val Glu Ala Val Lys Asp Ile Pro
1               5                   10                  15

Asp Gly Ala Thr Val Leu Val Gly Gly Phe Gly Leu Cys Gly Ile Pro
            20                  25                  30

Glu Asn Leu Ile Asp Ala Leu Leu Lys Thr Gly Val Lys Gly Leu Thr
        35                  40                  45

Ala Val Ser Asn Asn Ala Gly Val Asp Asn Phe Gly Leu Gly Leu Leu
    50                  55                  60

Leu Arg Ser Lys Gln Ile Lys Arg Met Val Ser Ser Tyr Val Gly Glu
65                  70                  75                  80

Asn Ala Glu Phe Glu Arg Gln Tyr Leu Ser Gly Glu Leu Glu Val Glu
                85                  90                  95
```

Leu Thr Pro Gln Gly Thr Leu Ala Glu Arg Ile Arg Ala Gly Gly Ala
            100                 105                 110

Gly Val Pro Ala Phe Tyr Thr Pro Thr Gly Tyr Gly Thr Leu Val Gln
        115                 120                 125

Glu Gly Gly Ser Pro Ile Lys Tyr Asn Lys Asp Gly Ser Val Ala Ile
    130                 135                 140

Ala Ser Lys Pro Arg Glu Val Arg Glu Phe Asn Gly Gln His Phe Ile
145                 150                 155                 160

Leu Glu Glu Ala Ile Thr Gly Asp Phe Ala Leu Val Lys Ala Trp Lys
                165                 170                 175

Ala Asp Arg Ala Gly Asn Val Ile Phe Arg Lys Ser Ala Arg Asn Phe
            180                 185                 190

Asn Leu Pro Met Cys Lys Ala Ala Glu Thr Thr Val Glu Val Glu
        195                 200                 205

Glu Ile Val Asp Ile Gly Ala Phe Ala Pro Glu Asp Ile His Ile Pro
    210                 215                 220

Gln Ile Tyr Val His Arg Leu Ile Lys Gly Lys Tyr Glu Lys Arg
225                 230                 235                 240

Ile Glu Arg Leu Ser Ile Arg Lys Glu Gly Asp Gly Glu Ala Lys Ser
                245                 250                 255

Ala Lys Pro Gly Asp Asp Val Arg Glu Arg Ile Ile Lys Arg Ala Ala
            260                 265                 270

Leu Glu Phe Glu Asp Gly Met Tyr Ala Asn Leu Gly Ile Gly Ile Pro
        275                 280                 285

Leu Leu Ala Ser Asn Phe Ile Ser Pro Asn Ile Thr Val His Leu Gln
    290                 295                 300

Ser Glu Asn Gly Val Leu Gly Leu Gly Pro Tyr Pro Arg Gln His Glu
305                 310                 315                 320

Ala Asp Ala Asp Leu Ile Asn Ala Gly Lys Glu Thr Val Thr Ile Leu
                325                 330                 335

Pro Gly Ala Ser Phe Phe Ser Ser Asp Glu Ser Phe Ala Met Ile Arg
            340                 345                 350

Gly Gly His Val Asp Leu Thr Met Leu Gly Ala Met Gln Val Ser Lys
        355                 360                 365

Tyr Gly Asp Leu Ala Asn Trp Met Ile Pro Gly Lys Met Val Lys Gly
    370                 375                 380

Met Gly Gly Ala Met Asp Leu Val Ser Ser Ala Lys Thr Lys Val Val
385                 390                 395                 400

Val Thr Met Glu His Ser Ala Lys Gly Asn Ala His Lys Ile Met Glu
                405                 410                 415

Lys Cys Thr Leu Pro Leu Thr Gly Lys Gln Cys Val Asn Arg Ile Ile
            420                 425                 430

Thr Glu Lys Ala Val Phe Asp Val Asp Lys Lys Gly Leu Thr Leu
        435                 440                 445

Ile Glu Leu Trp Glu Gly Leu Thr Val Asp Val Gln Lys Ser Thr
    450                 455                 460

Gly Cys Asp Phe Ala Val Ser Pro Lys Leu Met Pro Met Gln Gln Ile
465                 470                 475                 480

Ala Asn Ala Glu Asn Leu Tyr Phe Gln
                485

<210> SEQ ID NO 30
<211> LENGTH: 488
<212> TYPE: PRT

<213> ORGANISM: Sus scrofa

<400> SEQUENCE: 30

```
Thr Lys Phe Tyr Thr Asp Ala Val Glu Ala Val Lys Asp Ile Pro Asn
1               5                   10                  15
Gly Ala Thr Val Leu Val Gly Gly Phe Gly Leu Cys Gly Ile Pro Glu
            20                  25                  30
Asn Leu Ile Gly Ala Leu Leu Lys Thr Gly Val Lys Glu Leu Thr Ala
        35                  40                  45
Val Ser Asn Asn Ala Gly Val Asp Asn Phe Gly Leu Gly Leu Leu Leu
    50                  55                  60
Gln Ser Lys Gln Ile Lys Arg Met Ile Ser Ser Tyr Val Gly Glu Asn
65                  70                  75                  80
Ala Glu Phe Glu Arg Gln Tyr Leu Ala Gly Glu Leu Glu Val Glu Leu
                85                  90                  95
Thr Pro Gln Gly Thr Leu Ala Glu Arg Ile Arg Ala Gly Gly Ala Gly
            100                 105                 110
Val Pro Ala Phe Tyr Thr Ser Thr Gly Tyr Gly Thr Leu Val Gln Glu
        115                 120                 125
Gly Gly Ser Pro Ile Lys Tyr Asn Lys Asp Gly Ser Ile Ala Ile Ala
    130                 135                 140
Ser Lys Pro Arg Glu Val Arg Glu Phe Asn Gly Gln His Phe Ile Leu
145                 150                 155                 160
Glu Glu Ala Ile Arg Gly Asp Phe Ala Leu Val Lys Ala Trp Lys Ala
                165                 170                 175
Asp Gln Ala Gly Asn Val Thr Phe Arg Lys Ser Ala Arg Asn Phe Asn
            180                 185                 190
Leu Pro Met Cys Lys Ala Ala Glu Thr Thr Val Val Glu Val Glu Glu
        195                 200                 205
Ile Val Asp Ile Gly Ser Phe Ala Pro Glu Asp Ile His Ile Pro Lys
    210                 215                 220
Ile Tyr Val His Arg Leu Val Lys Gly Glu Lys Tyr Glu Lys Arg Ile
225                 230                 235                 240
Glu Arg Leu Ser Val Arg Lys Glu Glu Asp Val Lys Thr Arg Ser Gly
                245                 250                 255
Lys Leu Gly Asp Asn Val Arg Glu Arg Ile Ile Lys Arg Ala Ala Leu
            260                 265                 270
Glu Phe Glu Asp Gly Met Tyr Ala Asn Leu Gly Ile Gly Ile Pro Leu
        275                 280                 285
Leu Ala Ser Asn Phe Ile Ser Pro Asn Met Thr Val His Leu Gln Ser
    290                 295                 300
Glu Asn Gly Ile Leu Gly Leu Gly Pro Tyr Pro Leu Gln Asn Glu Val
305                 310                 315                 320
Asp Ala Asp Leu Ile Asn Ala Gly Lys Glu Thr Val Thr Val Leu Pro
                325                 330                 335
Gly Ala Ser Tyr Phe Ser Ser Asp Glu Ser Phe Ala Met Ile Arg Gly
            340                 345                 350
Gly His Val Asn Leu Thr Met Leu Gly Ala Met Gln Val Ser Lys Tyr
        355                 360                 365
Gly Asp Leu Ala Asn Trp Met Ile Pro Gly Lys Leu Val Lys Gly Met
    370                 375                 380
Gly Gly Ala Met Asp Leu Val Ser Ser Ala Lys Thr Lys Val Val Val
385                 390                 395                 400
```

```
Thr Met Glu His Ser Ala Lys Gly Asn Ala His Lys Ile Met Glu Lys
                405                 410                 415
Cys Thr Leu Pro Leu Thr Gly Lys Gln Cys Val Asn Arg Ile Ile Thr
            420                 425                 430
Glu Lys Ala Val Phe Asp Val Asp Arg Lys Lys Gly Leu Thr Leu Ile
        435                 440                 445
Glu Leu Trp Glu Gly Leu Thr Val Asp Asp Ile Lys Lys Ser Thr Gly
450                 455                 460
Cys Asp Phe Ala Val Ser Pro Lys Leu Ile Pro Met Gln Gln Leu Glu
465                 470                 475                 480
His His His His His His His
                485

<210> SEQ ID NO 31
<211> LENGTH: 481
<212> TYPE: PRT
<213> ORGANISM: Sus scrofa

<400> SEQUENCE: 31

Thr Lys Phe Tyr Thr Asp Ala Val Glu Ala Val Lys Asp Ile Pro Asn
1               5                   10                  15
Gly Ala Thr Val Leu Val Gly Gly Phe Gly Leu Cys Gly Ile Pro Glu
            20                  25                  30
Asn Leu Ile Gly Ala Leu Leu Lys Thr Gly Val Lys Glu Leu Thr Ala
        35                  40                  45
Val Ser Asn Asn Ala Gly Val Asp Asn Phe Gly Leu Gly Leu Leu Leu
    50                  55                  60
Gln Ser Lys Gln Ile Lys Arg Met Ile Ser Ser Tyr Val Gly Glu Asn
65                  70                  75                  80
Ala Glu Phe Glu Arg Gln Tyr Leu Ala Gly Glu Leu Glu Val Glu Leu
                85                  90                  95
Thr Pro Gln Gly Thr Leu Ala Glu Arg Ile Arg Ala Gly Gly Ala Gly
            100                 105                 110
Val Pro Ala Phe Tyr Thr Ser Thr Gly Tyr Gly Thr Leu Val Gln Glu
        115                 120                 125
Gly Gly Ser Pro Ile Lys Tyr Asn Lys Asp Gly Ser Ile Ala Ile Ala
    130                 135                 140
Ser Lys Pro Arg Glu Val Arg Glu Phe Asn Gly Gln His Phe Ile Leu
145                 150                 155                 160
Glu Glu Ala Ile Arg Gly Asp Phe Ala Leu Val Lys Ala Trp Lys Ala
                165                 170                 175
Asp Gln Ala Gly Asn Val Thr Phe Arg Lys Ser Ala Arg Asn Phe Asn
            180                 185                 190
Leu Pro Met Cys Lys Ala Ala Glu Thr Thr Val Val Glu Val Glu Glu
        195                 200                 205
Ile Val Asp Ile Gly Ser Phe Ala Pro Glu Asp Ile His Ile Pro Lys
    210                 215                 220
Ile Tyr Val His Arg Leu Val Lys Gly Glu Lys Tyr Glu Lys Arg Ile
225                 230                 235                 240
Glu Arg Leu Ser Val Arg Lys Glu Glu Asp Val Lys Thr Arg Ser Gly
                245                 250                 255
Lys Leu Gly Asp Asn Val Arg Glu Arg Ile Ile Lys Arg Ala Ala Leu
            260                 265                 270
Glu Phe Glu Asp Gly Met Tyr Ala Asn Leu Gly Ile Gly Ile Pro Leu
        275                 280                 285
```

```
Leu Ala Ser Asn Phe Ile Ser Pro Asn Met Thr Val His Leu Gln Ser
            290                 295                 300

Glu Asn Gly Ile Leu Gly Leu Gly Pro Tyr Pro Leu Gln Asn Glu Val
305                 310                 315                 320

Asp Ala Asp Leu Ile Asn Ala Gly Lys Glu Thr Val Thr Val Leu Pro
                325                 330                 335

Gly Ala Ser Tyr Phe Ser Ser Asp Glu Ser Phe Ala Met Ile Arg Gly
            340                 345                 350

Gly His Val Asn Leu Thr Met Leu Gly Ala Met Gln Val Ser Lys Tyr
        355                 360                 365

Gly Asp Leu Ala Asn Trp Met Ile Pro Gly Lys Leu Val Lys Gly Met
    370                 375                 380

Gly Gly Ala Met Asp Leu Val Ser Ser Ala Lys Thr Lys Val Val Val
385                 390                 395                 400

Thr Met Glu His Ser Ala Lys Gly Asn Ala His Lys Ile Met Glu Lys
                405                 410                 415

Cys Thr Leu Pro Leu Thr Gly Lys Gln Cys Val Asn Arg Ile Ile Thr
            420                 425                 430

Glu Lys Ala Val Phe Asp Val Asp Arg Lys Lys Gly Leu Thr Leu Ile
        435                 440                 445

Glu Leu Trp Glu Gly Leu Thr Val Asp Asp Ile Lys Lys Ser Thr Gly
    450                 455                 460

Cys Asp Phe Ala Val Ser Pro Lys Leu Ile Pro Met Gln Gln Val Thr
465                 470                 475                 480

Thr

<210> SEQ ID NO 32
<211> LENGTH: 481
<212> TYPE: PRT
<213> ORGANISM: Sus scrofa
<220> FEATURE:
<221> NAME/KEY: MOD_RES
<222> LOCATION: (72)..(72)
<223> OTHER INFORMATION: Any amino acid
<220> FEATURE:
<221> NAME/KEY: MOD_RES
<222> LOCATION: (195)..(195)
<223> OTHER INFORMATION: Any amino acid
<220> FEATURE:
<221> NAME/KEY: MOD_RES
<222> LOCATION: (278)..(278)
<223> OTHER INFORMATION: Any amino acid
<220> FEATURE:
<221> NAME/KEY: MOD_RES
<222> LOCATION: (298)..(298)
<223> OTHER INFORMATION: Any amino acid
<220> FEATURE:
<221> NAME/KEY: MOD_RES
<222> LOCATION: (349)..(349)
<223> OTHER INFORMATION: Any amino acid
<220> FEATURE:
<221> NAME/KEY: MOD_RES
<222> LOCATION: (359)..(359)
<223> OTHER INFORMATION: Any amino acid
<220> FEATURE:
<221> NAME/KEY: MOD_RES
<222> LOCATION: (363)..(363)
<223> OTHER INFORMATION: Any amino acid
<220> FEATURE:
<221> NAME/KEY: MOD_RES
<222> LOCATION: (375)..(375)
<223> OTHER INFORMATION: Any amino acid
<220> FEATURE:
<221> NAME/KEY: MOD_RES
<222> LOCATION: (384)..(384)
```

```
<223> OTHER INFORMATION: Any amino acid
<220> FEATURE:
<221> NAME/KEY: MOD_RES
<222> LOCATION: (388)..(388)
<223> OTHER INFORMATION: Any amino acid
<220> FEATURE:
<221> NAME/KEY: MOD_RES
<222> LOCATION: (402)..(402)
<223> OTHER INFORMATION: Any amino acid
<220> FEATURE:
<221> NAME/KEY: MOD_RES
<222> LOCATION: (414)..(414)
<223> OTHER INFORMATION: Any amino acid
<220> FEATURE:
<221> NAME/KEY: MOD_RES
<222> LOCATION: (476)..(476)
<223> OTHER INFORMATION: Any amino acid

<400> SEQUENCE: 32

Thr Lys Phe Tyr Thr Asp Ala Val Glu Ala Val Lys Asp Ile Pro Asn
1               5                   10                  15

Gly Ala Thr Val Leu Val Gly Gly Phe Gly Leu Cys Gly Ile Pro Glu
            20                  25                  30

Asn Leu Ile Gly Ala Leu Leu Lys Thr Gly Val Lys Glu Leu Thr Ala
        35                  40                  45

Val Ser Asn Asn Ala Gly Val Asp Asn Phe Gly Leu Gly Leu Leu Leu
    50                  55                  60

Gln Ser Lys Gln Ile Lys Arg Xaa Ile Ser Ser Tyr Val Gly Glu Asn
65                  70                  75                  80

Ala Glu Phe Glu Arg Gln Tyr Leu Ala Gly Glu Leu Glu Val Glu Leu
                85                  90                  95

Thr Pro Gln Gly Thr Leu Ala Glu Arg Ile Arg Ala Gly Gly Ala Gly
            100                 105                 110

Val Pro Ala Phe Tyr Thr Ser Thr Gly Tyr Gly Thr Leu Val Gln Glu
        115                 120                 125

Gly Gly Ser Pro Ile Lys Tyr Asn Lys Asp Gly Ser Ile Ala Ile Ala
    130                 135                 140

Ser Lys Pro Arg Glu Val Arg Glu Phe Asn Gly Gln His Phe Ile Leu
145                 150                 155                 160

Glu Glu Ala Ile Arg Gly Asp Phe Ala Leu Val Lys Ala Trp Lys Ala
                165                 170                 175

Asp Gln Ala Gly Asn Val Thr Phe Arg Lys Ser Ala Arg Asn Phe Asn
            180                 185                 190

Leu Pro Xaa Cys Lys Ala Ala Glu Thr Thr Val Val Glu Val Glu Glu
        195                 200                 205

Ile Val Asp Ile Gly Ser Phe Ala Pro Glu Asp Ile His Ile Pro Lys
    210                 215                 220

Ile Tyr Val His Arg Leu Val Lys Gly Glu Lys Tyr Glu Lys Arg Ile
225                 230                 235                 240

Glu Arg Leu Ser Val Arg Lys Glu Glu Asp Val Lys Thr Arg Ser Gly
                245                 250                 255

Lys Leu Gly Asp Asn Val Arg Glu Arg Ile Ile Lys Arg Ala Ala Leu
            260                 265                 270

Glu Phe Glu Asp Gly Xaa Tyr Ala Asn Leu Gly Ile Gly Ile Pro Leu
        275                 280                 285

Leu Ala Ser Asn Phe Ile Ser Pro Asn Xaa Thr Val His Leu Gln Ser
    290                 295                 300

Glu Asn Gly Ile Leu Gly Leu Gly Pro Tyr Pro Leu Gln Asn Glu Val
305                 310                 315                 320
```

```
Asp Ala Asp Leu Ile Asn Ala Gly Lys Glu Thr Val Thr Val Leu Pro
            325                 330                 335

Gly Ala Ser Tyr Phe Ser Ser Asp Glu Ser Phe Ala Xaa Ile Arg Gly
            340                 345                 350

Gly His Val Asn Leu Thr Xaa Leu Gly Ala Xaa Gln Val Ser Lys Tyr
            355                 360                 365

Gly Asp Leu Ala Asn Trp Xaa Ile Pro Gly Lys Leu Val Lys Gly Xaa
            370                 375                 380

Gly Gly Ala Xaa Asp Leu Val Ser Ser Ala Lys Thr Lys Val Val Val
385                 390                 395                 400

Thr Xaa Glu His Ser Ala Lys Gly Asn Ala His Lys Ile Xaa Glu Lys
            405                 410                 415

Cys Thr Leu Pro Leu Thr Gly Lys Gln Cys Val Asn Arg Ile Ile Thr
            420                 425                 430

Glu Lys Ala Val Phe Asp Val Asp Arg Lys Lys Gly Leu Thr Leu Ile
            435                 440                 445

Glu Leu Trp Glu Gly Leu Thr Val Asp Asp Ile Lys Lys Ser Thr Gly
            450                 455                 460

Cys Asp Phe Ala Val Ser Pro Lys Leu Ile Pro Xaa Gln Gln Val Thr
465                 470                 475                 480

Thr

<210> SEQ ID NO 33
<211> LENGTH: 241
<212> TYPE: PRT
<213> ORGANISM: Bacillus subtilis

<400> SEQUENCE: 33

Ser Asn Ala Met Gly Lys Val Leu Ser Ser Lys Glu Ala Ala Lys
1               5                   10                  15

Leu Ile His Asp Gly Asp Thr Leu Ile Ala Gly Gly Phe Gly Leu Cys
            20                  25                  30

Gly Ile Pro Glu Gln Leu Ile Leu Ser Ile Arg Asp Gln Gly Val Lys
            35                  40                  45

Asp Leu Thr Val Val Ser Asn Asn Cys Gly Val Asp Asp Trp Gly Leu
        50                  55                  60

Gly Leu Leu Leu Ala Asn Lys Gln Ile Lys Lys Met Ile Ala Ser Tyr
65                  70                  75                  80

Val Gly Glu Asn Lys Ile Phe Glu Arg Gln Phe Leu Ser Gly Glu Leu
                85                  90                  95

Glu Val Glu Leu Val Pro Gln Gly Thr Leu Ala Glu Arg Ile Arg Ala
            100                 105                 110

Gly Gly Ala Gly Ile Pro Gly Phe Tyr Thr Ala Thr Gly Val Gly Thr
            115                 120                 125

Ser Ile Ala Glu Gly Lys Glu His Lys Thr Phe Gly Gly Arg Thr Tyr
        130                 135                 140

Val Leu Glu Arg Gly Ile Thr Gly Asp Val Ala Ile Val Lys Ala Trp
145                 150                 155                 160

Lys Ala Asp Thr Met Gly Asn Leu Ile Phe Arg Lys Thr Ala Arg Asn
                165                 170                 175

Phe Asn Pro Ile Ala Ala Met Ala Gly Lys Ile Thr Ile Ala Glu Ala
            180                 185                 190

Glu Glu Ile Val Glu Ala Gly Glu Leu Asp Pro Asp His Ile His Thr
            195                 200                 205
```

```
Pro Gly Ile Tyr Val Gln His Val Val Leu Gly Ala Ser Gln Glu Lys
    210             215                 220
Arg Ile Glu Lys Arg Thr Val Gln Gln Ala Ser Gly Lys Gly Glu Ala
225             230                 235                 240
Lys
```

POLYPEPTIDES FOR CARBON-CARBON BOND FORMATION AND USES THEREOF

This application claims priority to U.S. Provisional Patent Application No. 62/255,276, filed Nov. 13, 2015.

SEQUENCE LISTING

The instant application contains a Sequence Listing which has been submitted electronically in ASCII format and is hereby incorporated by reference in its entirety. Said ASCII copy, created on Nov. 8, 2016, is named 12444_6013-00000_SL.txt and is 113,030 bytes in size.

TECHNICAL FIELD

This disclosure provides multifunctional polypeptides. This disclosure provides polypeptides having a β-ketothiolase and CoA transferase activities and variants thereof. The disclosure provides methods for C—C bond formation useful for biosynthesizing thioesters of 3-keto-acids and derivatives thereof via condensation of acetyl-CoA with alkanoic, (substituted) alkenoic or hydroxy- or haloacids or their CoA esters. These 3-keto-acyl-CoA esters are useful for, for example, the microbial or biocatalytic production of industrially important compounds including straight chain fatty acids, ω-alkenoic acids, ω-hydroxy fatty acids, alkanes, alkenes, ketones, and as precursors for butadiene and isoprene. For example, 3-oxopent-4-enoyl-CoA and 4-methyl-3-oxopent-4-enoyl-CoA can be prepared using such polypeptides. This invention also relates to methods for producing 3-butene-2-ol and 3-methyl-3-butene-2-ol from 3-oxo-pent-4-enoic acid and 4-methyl-3-oxopent-4-enoic acid, respectively using an alcohol dehydrogenase or a phenylacetaldehyde reductase or using recombinant host cells expressing one or more such polypeptides.

BACKGROUND

Biosynthetic thiolases catalyse carbon-carbon bond formation via a thioester-dependent Claisen-condensation reaction mechanism. This is an essential first step of many biosynthetic pathways relying on the stepwise assembly of carbon backbones from 2- and 3-carbon metabolites, including fatty acids and lipids, polyketides, isoprenoids, cholesterol, steroid hormones and ketone bodies. Many of these compounds are industrially important chemicals due to their biological activity or potential application as building blocks or substrates for the production of bulk chemicals and pharmaceuticals (Klein, M. (2009) *Enzyme and Microbial Technology*, 45, p. 361-366).

Biosynthetic thiolases (EC 2.3.1.9) such as BktB from *Ralstonia eutropha* are also involved in poly-hydroxalkanoate biosynthesis, and serve to condense either two acetyl-CoA's to form acetoacetyl-CoA in polyhydroxybutyrate (PHB) biosynthesis or to condense acetyl-CoA with propionyl-CoA or butyryl-CoA to form valeryl-CoA or hexanoyl-CoA (Kim, Eun-Jung et al., 2014, *Biochemical and Biophysical Research Communications*, 444, 3, p. 365-369).

Sustainable production of advanced biofuels and chemicals from renewable feedstocks requires metabolic engineering of microorganisms to synthesise longer carbon chain length compounds from 2- and 3-carbon metabolic intermediates. Invariably, this requires C—C-bond formation by biosynthetic thiolases. For example, reversal of the β-oxidation cycle provides a platform for the synthesis of fatty acids and fatty acid-derived chemicals, using biosynthetic thiolases to initiate and reverse the cycle so that the carbon backbone is extended rather than degraded (Clomburg, James et al., 2015, *Metabolic Engineering* 28, p. 202-212). This reverse β-oxidation cycle can be used to generate a diverse range of products (Cintolesi, Angela et al., 2014, *Metabolic engineering* 23, p. 100-115; Dellomonaco, 2011, *Nature*, vol 476, p. 355-359). The intermediates of the reverse β-oxidation cycle can be removed from the cycle to form 3-keto-fatty acids or the corresponding methyl ketones via decarboxylation, medium chain length polyesters, fatty aldehydes, fatty alcohols, fatty acids, alkanes, and alkenes (Yu, Ai-Qun, 2014, *Frontiers in Bioengineering and Biotechnology*, Vol 2, article 78).

The products from the reverse β-oxidation cycle can also be transferred from the reverse β-oxidation cycle to the fatty acid biosynthesis (FAS) cycle by employing enzymes that transfer the acyl-phosphopantetheine group from acyl-CoA to apo-ACP such as sfp-type PPTase (phosphopantetheinyl transferases) (*Methods in Enzymology*, Volume 458, Chapter 10; Beld, Joris et al., 2014, *Nat. Prod. Rep.* 31, 61-108). The fatty-acyl-ACP's can similarly be removed from the FAS cycle by a variety of enzymes to produce fatty acids and fatty-acid derived chemicals such as hydroxy fatty acids, fatty aldehydes, fatty alcohols, alkenes, and dicarboxylic acids (Janβen & Steinbüchel, 2014, *Biotechnology for Biofuels*, 7:7).

Supplying 3-keto-acyl-ACP substrates produced by biosynthetic thiolases followed by transfer of the acyl-phosphopantetheine group to apo-ACP, also provides an alternative entry of 3-keto-acyl-ACP's into the FAS cycle not relying on KAS III type β-ketoacyl-ACP synthases (EC 2.3.1.180, FabH) that require malonyl-ACP as extender to improve the overall carbon and energy efficiency of product synthesis (Dellomonaco, 2011, *Nature*, vol 476, p. 355-359).

Enzymes that are capable of C—C bond formation to condense acetyl-CoA with acids or CoA activated acids to form 3-keto-acyl-CoA esters, such as biosynthetic thiolases, are thus essential enzymes, not only in the synthesis of fatty acids and fatty acid-derived chemicals by providing the 3-keto-acyl-CoA or 3-keto-acyl-ACP intermediates to either the reverse β-oxidation or the FAS cycle, but also in polyhydroxyalkanoate biosynthesis and in the production of fermentation products such as butanol, butyric acid, acetone and hydrogen by clostridia (Klein, M. 2009. *Enzyme and Microbial Technology*, 45, 361-366), and many other biochemical pathways such as isoprenoids and polyketides.

However, all known biosynthetic thiolases have certain limitations. For example, they require two cysteine residues for their catalytic mechanism. In the acyl transfer step, Cys 378 protonates the CoA leaving group, and the acetyl group is transferred to Cys 89. In the subsequent Claisen condensation reaction, the deprotonated Cys378 abstracts the proton of the C2 atom of acetyl-CoA, facilitating its nucleophilic attack on the carbonyl carbon of the acetyl group that is covalently bound to the Cys 89 sulfur atom, which leads to C—C bond formation and release of the acyl group from Cys 89. This two-step "ping-pong" mechanism is also found in the biosynthetic thiolases involved in PHA biosynthesis of haloarchae, but in this case, Cys 89 is replaced by a Ser, leading to a Ser-His-Cys catalytic triad rather than a Cys-His-Cys triad found in other thiolases (Hou, Jing et al., 2013, Applied and Environmental Microbiology, Vol 79, number 17, p 5104-5111). Substrates with electrophilic groups, such as acrylic acid thioesters and haloacetyl-CoA analogs, irreversibly inactivate biosynthetic thiolases through both acylation of Cys 89 and alkylation of Cys 378 (Palmer, M. A. et al., J Biol Chem, 264 (1991), pp. 15293-15297; Palmer, M. A. et al., J Biol Chem, 266 (1991), pp. 8369-8375; Davis, Jeffrey T. et al., J Biol Chem, 262 (1987) pp. 90-96). For further example, biosynthetic thiolases are restricted to short chain substrates (C4 or shorter) such as acetyl-CoA, propanoyl-CoA, and butanoyl-CoA. Therefore, the longest acyl chain accepted by biosynthetic thiolases consist of only 4 carbon atoms due to the shape of the substrate binding pocket (Modis, Yorgo and Wiernga, Rik K. 1999, Structure, Vol 7 no. 10 p. 1279-1290).

SUMMARY

It is of interest to provide enzymes capable of C—C bond formation to form 3-keto-acyl thioesters, not only to supplement the available biosynthetic thiolases, but also to overcome their limitations: (1) inactivation by electrophilic substrates such as acrylic acid, methacrylic acid, or ω-hydroxy-acid thioesters; and (2) inability to condense acetyl-CoA with substrates of chain length greater than C4. Surprisingly, the inventors have discovered enzymes that can overcome these limitations, which will allow the diversification of chemicals that can be obtained via 3-keto-acyl-CoA intermediates. These chemicals include precursors of bulk chemicals such as butadiene and isoprene, polyhydroxyalkanoate pathways intermediates and products, chemicals derived from fatty acid metabolism (both from reverse β-oxidation and fatty acid biosynthesis), as well as chemicals derived from polyketide and isoprenoid pathways, as well as clostridial fermentation products.

This document is based at least in part on the discovery that it is possible to use CoA transferases from EC 2.8.3.- to catalyze not only CoA transfer, but also Claisen type condensation associated with biosynthetic thiolases, to produce 3-keto-acyl-CoA esters from the condensation of acetyl-CoA with alkanoic, (substituted) alkenoic, hydroxy- or halo-acids or their CoA esters.

In one aspect, this document provides a method to produce 3-keto acids of carbon chain length n+2 by providing cells expressing enzymes from EC 2.8.3.- with straight chain alkanoic acids of carbon chain length n (n>2) such as acetate, propionate, butyrate, pentanoic acid, hexanoic acid, and the like, or branched chain alkanoic acids such as isobutyrate, isovaleric acid, and pivalic acid, in addition to a carbon source suitable for growth to provide acetyl-CoA.

In one aspect, this document provides a method to produce 3-keto acids of carbon chain length n+2 by providing cells expressing enzymes from EC 2.8.3.- with straight chain alkenoic acids of carbon chain length n (n>2) such as acrylic acid, 2-propenoic acid, 3-butenoic acid, 4-pentenoic acid, 5-hexenoic acid, 6-hepteneoic acid, crotonic acid, and the like, or branched chain alkenoic acids such as methacrylic acid, 3-methyl-3-butenoic acid, 4-methyl-4-pentenoic acid, 5-methyl-5-hexenoic acid, and the like, in addition to a carbon source suitable for growth, to provide acetyl-CoA.

In one aspect, this document provides a method to produce 3-keto acids of carbon chain length n+2 by providing cells expressing enzymes from EC 2.8.3.- with hydroxy- or halo-acids of carbon chain length n (n>2) such as 3-hydroxypropionic acid, 4-hydroxybutyric acid, 5-hydroxyvaleric acid, 6-hydroxy-caproic acid, or the corresponding halogen substituted acid, and the like, in addition to a carbon source suitable for growth to provide acetyl-CoA.

In another aspect, both the acetyl-CoA and the acid partner for the condensation reaction (or its activated CoA ester) are derived from a fermentable carbon source, either via a naturally occurring pathway or via an engineered pathway. As an example, acryloyl-CoA, methacryloyl-CoA, propanoyl-CoA, and butanoyl-CoA are naturally occurring metabolites in many organisms, and their intracellular production can be improved by metabolic engineering strategies. (Pathways leading to acryloyl-CoA and propanoyl-CoA had been described in PCT Application PCT/US2014/048606.)

In another aspect, the 3-keto-acyl-CoA product of the condensation reaction is converted to the free acid by a CoA transferase or a thioesterase.

This document is based at least in part on the discovery that it is possible to construct a biochemical pathway for producing butadiene utilizing a polypeptide having both β-ketothiolase and CoA transferase activity, where that polypeptide can both (i) transfer a Coenzyme A (CoA) moiety from a CoA source such as acetyl-CoA to a short

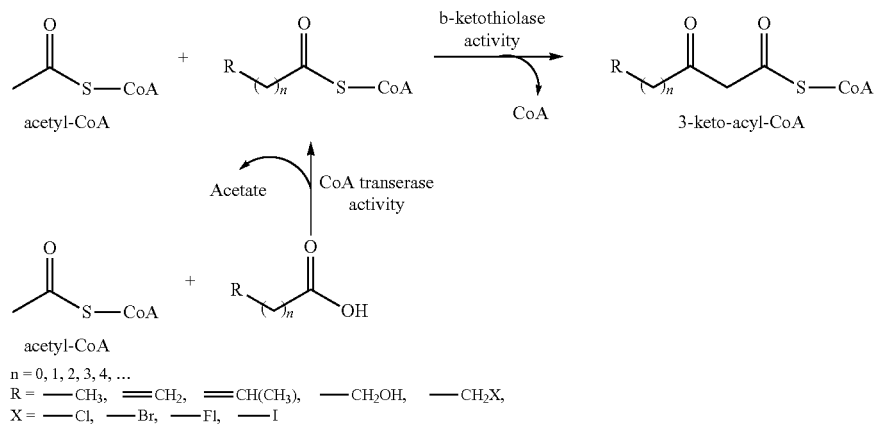

chain alkyl or alkenyl carboxylate such as acrylate, propionate, or butyrate, and salt forms thereof (e.g., sodium acrylate, sodium propionate, or sodium butyrate) (referred to as CoA transferase activity) and (ii) condense a short-chain acyl-CoA such as acryloyl-CoA, propionyl-CoA, or butyryl-CoA with an acetyl-CoA moiety (referred to as β-ketothiolase activity).

In one aspect, this document provides polypeptides with dual CoA transferase and β-ketothiolase activity. In one embodiment, the polypeptide having both CoA transferase and β-ketothiolase activities is classified under EC 2.8.3.-, for example under EC 2.8.3.8. In one embodiment, the polypeptide having both CoA transferase and β-ketothiolase activities has at least 95% sequence identity to the amino acid sequence set forth in any one of SEQ ID NO: 1, 4, 5, 6, 7, 8, and 9. Also provided are variants of polypeptides having both CoA transferase and β-ketothiolase activities wherein either or both of these activities have been increased, decreased, or abolished via introduction of mutations.

In one aspect, this document provides methods of producing 3-oxopent-4-enoyl-CoA using a polypeptide that has both CoA transferase and β-ketothiolase activities. In one embodiment, said methods can further comprise converting 3-oxopent-4-enoyl-CoA to 3-oxopent-4-enoate. In one embodiment, said methods can further comprise converting 3-oxopent-4-enoate to 3-buten-2-one. In one embodiment, said methods can further comprise converting 3-buten-2-one to 3-buten-2-ol. In one embodiment, said methods can further comprise converting 3-buten-2-ol to 1,3-butadiene.

In one aspect, this document provides methods of producing 3-oxo-acyl-CoA compounds using a polypeptide that has both CoA transferase and β-ketothiolase activities.

In one aspect, this document provides methods of producing 3-oxo-enoyl-CoA compounds using a polypeptide that has both CoA transferase and β-ketothiolase activities.

In one aspect, this document provides methods of producing 3-oxo-hydroxyacyl-CoA compounds using a polypeptide that has both CoA transferase and β-ketothiolase activities. In some embodiments, said 3-oxo-hydroxyacyl-CoA compounds can be further converted to nylon compounds.

In one aspect, methods described in this document may be performed in a non-naturally occurring host.

In one aspect, this document provides hosts capable of producing 3-oxopent-4-enoyl-CoA, said hosts comprising at least one exogenous nucleic acid encoding a polypeptide that has both CoA transferase and β-ketothiolase activities. In one aspect, this document provides hosts capable of producing 1,3-butadiene, said hosts comprising at least one exogenous nucleic acid encoding a polypeptide that has both CoA transferase and β-ketothiolase activities.

In one aspect, this document provides hosts capable of producing 3-oxo-acyl-CoA compounds, said hosts comprising at least one exogenous nucleic acid encoding a polypeptide that has both CoA transferase and β-ketothiolase activities.

In one aspect, this document provides hosts capable of producing 3-oxo-enoyl-CoA compounds, said hosts comprising at least one exogenous nucleic acid encoding a polypeptide that has both CoA transferase and β-ketothiolase activities.

In one aspect, this document provides hosts capable of producing 3-oxo-hydroxyacyl-CoA compounds, said hosts comprising at least one exogenous nucleic acid encoding a polypeptide that has both CoA transferase and β-ketothiolase activities.

In one aspect, the principal carbon source for the methods and hosts described in this document derives from a biological feedstock. In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

In one aspect, the principal carbon source for the methods and hosts described in this document derives from a non-biological feedstock. In some embodiments, the non-biological feedstock can be or can derive from natural gas, syngas, $CO_2/H_2$, methanol, ethanol, benzoate, non-volatile residue (NVR), or a caustic wash waste stream from cyclohexane oxidation processes, or terephthalic acid/isophthalic acid mixture waste streams.

In some embodiments, the host microorganism's tolerance to high concentrations of one or more of 3-oxopent-4-enoyl-CoA, 3-oxopentanoyl-CoA, 3-oxohexanoyl-CoA, 3-buten-2-one, 3-butene-2-ol, or butadiene is improved through continuous cultivation in a selective environment.

In some embodiments, the host microorganism's biochemical network is attenuated or augmented to (1) ensure the intracellular availability of acetyl-CoA, (2) create an NADH or NADPH imbalance that may only be balanced via the formation of one or more of 3-oxopent-4-enoyl-CoA, 3-oxopentanoyl-CoA, 3-oxohexanoyl-CoA, 3-buten-2-one, 3-butene-2-ol, or butadiene, (3) prevent degradation of central metabolites, central precursors leading to and including 3-oxopent-4-enoyl-CoA, 3-oxopentanoyl-CoA, 3-oxohexanoyl-CoA, 3-buten-2-one, 3-butene-2-ol, or butadiene, and (4) ensure efficient efflux from the cell.

In some embodiments, a cultivation strategy is used to achieve anaerobic, micro-aerobic, or aerobic cultivation conditions.

In some embodiments, the cultivation strategy includes limiting nutrients, such as limiting nitrogen, phosphate, or oxygen.

In some embodiments, one or more of 3-oxopent-4-enoyl-CoA, 3-oxopentanoyl-CoA, 3-oxohexanoyl-CoA, 3-buten-2-one, 3-butene-2-ol, or butadiene are produced by a single type of microorganism, e.g., a non-naturally occurring host, such as a recombinant host, containing one or more exogenous nucleic acids, using, for example, a fermentation strategy.

Any of the non-naturally occurring hosts can be a prokaryote such as a prokaryote from a genus selected from the group consisting of *Eschenchia, Clostridia, Corynebacteria, Cupriavidus, Pseudomonas, Delftia, Bacilluss, Lactobacillus, Lactococcus*, and *Rhodococcus*. For example, the prokaryote can be selected from the group consisting of *Escherichia coli, Clostridium Ijungdahlii, Clostridium autoethanogenum, Clostridium kluyvenri, Corynebacterium glutamicum, Cupriavidus necator, Cupriavidus metallidurans, Pseudomonas fluorescens, Pseudomonas putida, Pseudomonas oleavorans, Delftia acidovorans, Bacillus subtillis, Lactobacillus delbruekii, Lactococcus lactis*, and *Rhodococcus equi*. Such prokaryotes also can be sources of genes for constructing recombinant host cells described herein that are capable of producing one or more of 3-oxopent-4-enoyl-CoA, 3-oxopentanoyl-CoA, 3-oxohexanoyl-CoA, 3-buten-2-one, 3-butene-2-ol, and butadiene.

Any of the non-naturally occurring hosts can be a eukaryote such as a eukaryote from a genus selected from the group consisting of *Aspergillus, Saccharomyces, Pichia, Yarrowia, Issatchenkia, Debaryomyces, Arxula*, and *Kluyveromyces*. For example, the eukaryote can be selected from the group consisting of *Aspergillus niger, Saccharomyces cerevisiae, Pichia pastoris, Yarrowia lipolytica, Issathenkia orientalis, Debaryomyces hansenii, Arxula adenoinivorans*, and *Kluyveromyces lactis*. Such eukaryotes also can be sources of genes for constructing recombinant host cells described herein that are capable of producing one or more of 3-oxopent-4-enoyl-CoA, 3-oxopentanoyl-CoA, 3-oxohexanoyl-CoA, 3-buten-2-one, 3-butene-2-ol, and butadiene.

This document also features a biochemical network comprising a polypeptide with both β-ketothiolase and CoA transferase activities, for example a polypeptide classified under EC 2.8.3.8, propenoate, acetyl Co-A, propenoyl-CoA, and 3-oxopent-4-enoyl-CoA, wherein the polypeptide enzymatically condenses propenoate and acetyl-CoA to propenoyl-CoA and converts propenoyl-CoA to 3-oxopent-4-enoyl-CoA. The biochemical network further can include a CoA transferase, a decarboxylase, an alcohol dehydrogenase, a phenylacetaldehyde reductase, a linalool dehydratase, and combinations thereof to enzymatically convert 3-oxopent-4-enoyl-CoA to butadiene.

This document also features a means for producing 3-oxopent-4-enoyl-CoA, wherein the means enzymatically condense propenoate and acetyl-CoA to propenoyl-CoA and convert propenoyl-CoA to 3-oxopent-4-enoyl-CoA. The means can include a polypeptide with both β-ketothiolase and CoA transferase activities, for example a polypeptide classified under EC 2.8.3.8. The means further can include one or more polypeptides for enzymatically converting 3-oxopent-4-enoyl-CoA to butadiene. The means can include a CoA transferase, a decarboxylase, an alcohol dehydrogenase, a phenylacetaldehyde reductase, a linalool dehydratase, and combinations thereof.

This document also features a step for obtaining 3-oxopent-4-enoyl-CoA using a polypeptide with both β-ketothiolase and CoA transferase activities, for example a polypeptide classified under EC 2.8.3.8.

In another aspect, this document features a composition comprising propenoate, acetyl-CoA, propenoyl-CoA, bio-derived 3-oxopent-4-enoyl-CoA, and a polypeptide with both β-ketothiolase and CoA transferase activities and classified under EC 2.8.3.8. The composition can be acellular or cellular.

In another aspect, this document features a composition comprising bio-derived 3-oxopent-4-enoyl-CoA, 3-oxopentanoyl-CoA, 3-oxohexanoyl-CoA, 3-buten-2-one, 3-butene-2-ol, or butadiene. The composition can be acellular or cellular.

In another aspect, this document features bio-derived or fermentation-derived 3-oxopent-4-enoyl-CoA, produced by the method of enzymatically condensing propenoate and acetyl-CoA to propenoyl-CoA, and converting propenoyl-CoA to 3-oxopent-4-enoyl-CoA using a polypeptide with both β-ketothiolase and CoA transferase activities, for example a polypeptide classified under EC 2.8.3.8.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. For example, see PCT/US2014/048606 (thiolases from archae), U.S. Pat. No. 9,422,580 (e.g., FIGS. 3, 5, and 9), and U.S. Pat. No. 9,422,578 (e.g., FIG. 9), teaching, for example, propenoyl-CoA condensation with acetyl-CoA to form 3-oxopent-4-enoyl-CoA; and the thiolase reaction between 4-hydroxybutarate and acetyl-CoA to form 3-oxo-6-hydroxyhexanoyl-CoA, as depicted in various aspects in U.S. Application Ser. No. 62/079,903; the thiolase reaction between acetyl-CoA and saturated alkanoic acids depicted in, for example, U.S. application Ser. Nos. 62/255,303 and 62/079,903. Some thiolases such as PaaJ are well known in the art. In case of conflict, the present specification, including definitions, will control. In addition, the materials, methods, and examples are illustrative only and not intended to be limiting. The details of one or more embodiments of the disclosure are set forth in the accompanying drawings and the description below. Other features, objects, and advantages of the disclosure will be apparent from the description and drawings, and from the claims. The word "comprising" in the claims may be replaced by "consisting essentially of" or with "consisting of," according to standard practice in patent law.

DESCRIPTION OF DRAWINGS

FIG. 1B shows four exemplary biochemical pathways to produce 3-keto-acyl-CoA esters from condensation of acetyl-CoA with an (i) alkanoic, (ii) alkenoic, (iii) hydroxy-, or (iv) halo-acid using a polypeptide with both β-ketothiolase and CoA transferase activities.

FIG. 1C shows four exemplary biochemical pathways to produce 3-keto-acyl-CoA esters from condensation of acetyl-CoA with a salt of an (i) alkanoic, (ii) alkenoic, (iii) hydroxy-, or (iv) halo-acid using a polypeptide with both β-ketothiolase and CoA transferase activities.

FIG. 2A contains the amino acid sequences of a *Clostridium propionicum* acetate CoA transferase (YdiF) (see GenBank Accession No. Q9L3F7, SEQ ID NO: 1); FIG. 2B contains the amino acid sequences of a modified *Clostridium propionicum* acetate CoA transferase (SEQ ID NO: 2); FIG. 2C contains the amino acid sequences of a modified *Clostridium propionicum* acetate CoA transferase containing an E324G mutation (SEQ ID NO: 3); FIG. 2D contains the amino acid sequences of a modified *Clostridium propionicum* acetate CoA transferase containing an E324L mutation (SEQ ID NO: 4) and a *Peptostreptococcaceae* acetate CoA-transferase (Uniprot Accession No. U2L5C9, SEQ ID NO: 5); FIG. 2E contains the amino acid sequences of a Firmicutes bacterium acetate CoA-transferase (Uniprot Accession No. R5ADR5, SEQ ID NO: 6) and a *Megasphaera elsdenii* acetate CoA-transferase (Uniprot Accession No. G0VND6, SEQ ID NO: 7); FIG. 2F contains the amino acid sequences of a *Dyadobacter fermentans* Acetyl-CoA acetyltransferase (Uniprot Accession No. C6VTZ3, SEQ ID NO: 8) and a *Salmonella enterica* subsp. *houtenaeserovar* acetate CoA-transferase (Uniprot Accession No. V1HBS2, SEQ ID NO: 9); FIG. 2G contains the amino acid sequences of an *Escherichia coli* acetyl-CoA:acetoacetyl-CoA transferase encoded by atoAD (GenBank Accession Nos. AAC75282.1 (beta subunit) and AAC75281.1 (alpha subunit), SEQ ID NOs:10 and 11, respectively); FIG. 2H contains the amino acid sequences of a *Pseudomonas putida* 3-oxoacid CoA-transferase encoded by pcalJ (GenBank Accession No. ACA73091.1 (A subunit) and ACA73090.1 (B subunit), SEQ ID NO: 12 and 13, respectively), a *Chromobacterium violaceum* acetoacetate decarboxylase (GenBank Accession No. AAQ61181.1, SEQ ID NO: 14), and a *Clostridium acetobutylicum* acetoacetate decarboxylase (Genbank Accession No. AAA63761.1, SEQ ID NO: 15); FIG. 2I contains the amino acid sequences of a *Nocardia rhamnosiphila* alcohol dehydrogenase (GenBank Accession No. WP_030525792, SEQ ID NO: 16) and a *Rhodococcus* sp. ST-10 phenylacetaldehyde reductase (Uniprot Accession No. Q9ZN85, SEQ ID NO: 17); FIG. 2J contains the amino acid sequences of a *Castellaniella defragrans* linalool dehydratase (Uniprot Accession No. E1XUJ2, SEQ ID NO: 18) and a *Clostridium aminobutyricum* CoA-transferase (Uniprot Accession No. Q9RM86, SEQ ID NO: 19); and FIG. 2K contains the amino acid sequences of a *Candida parapsilosis* carbonyl reductase (Uniprot Accession No. B2KJ46, SEQ ID NO: 20).

DETAILED DESCRIPTION

Figure 1A:
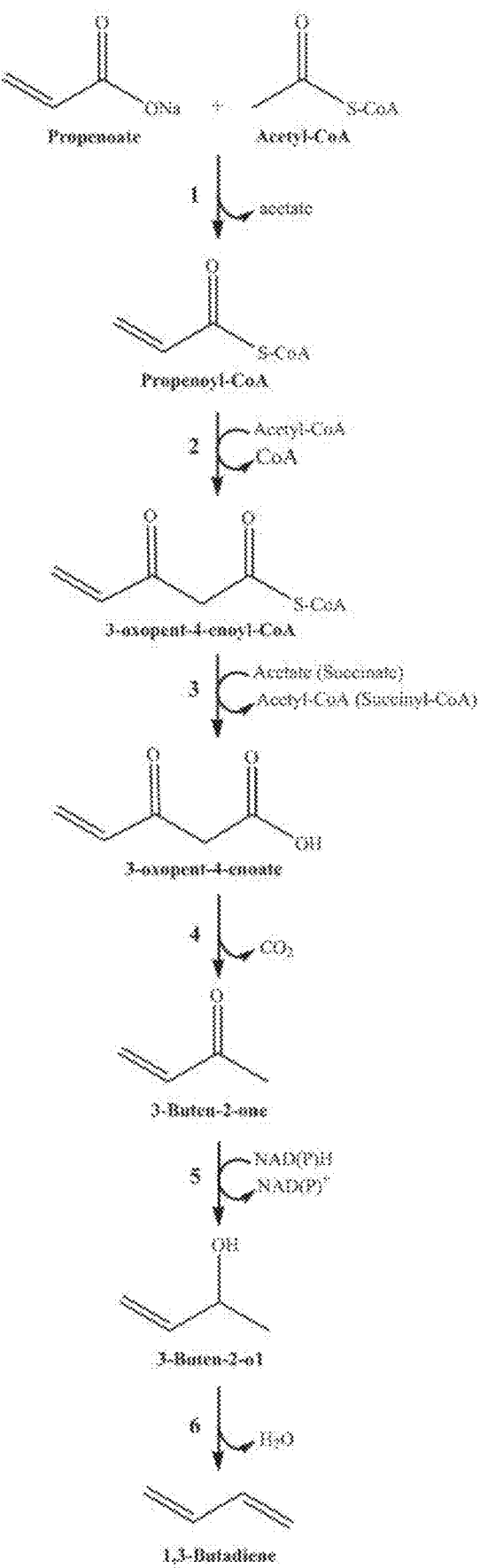
FIG. 1A is a schematic of an exemplary biochemical pathway leading to butadiene from propenoate (also known as acrylate) using (1) a polypeptide with both β-ketothiolase and CoA transferase activities; (2) a CoA transferase; (3) a decarboxylase; (4) an alcohol dehydrogenase or phenylacetaldehyde reductase; and (5) a linalool dehydratase.
Figure 3:
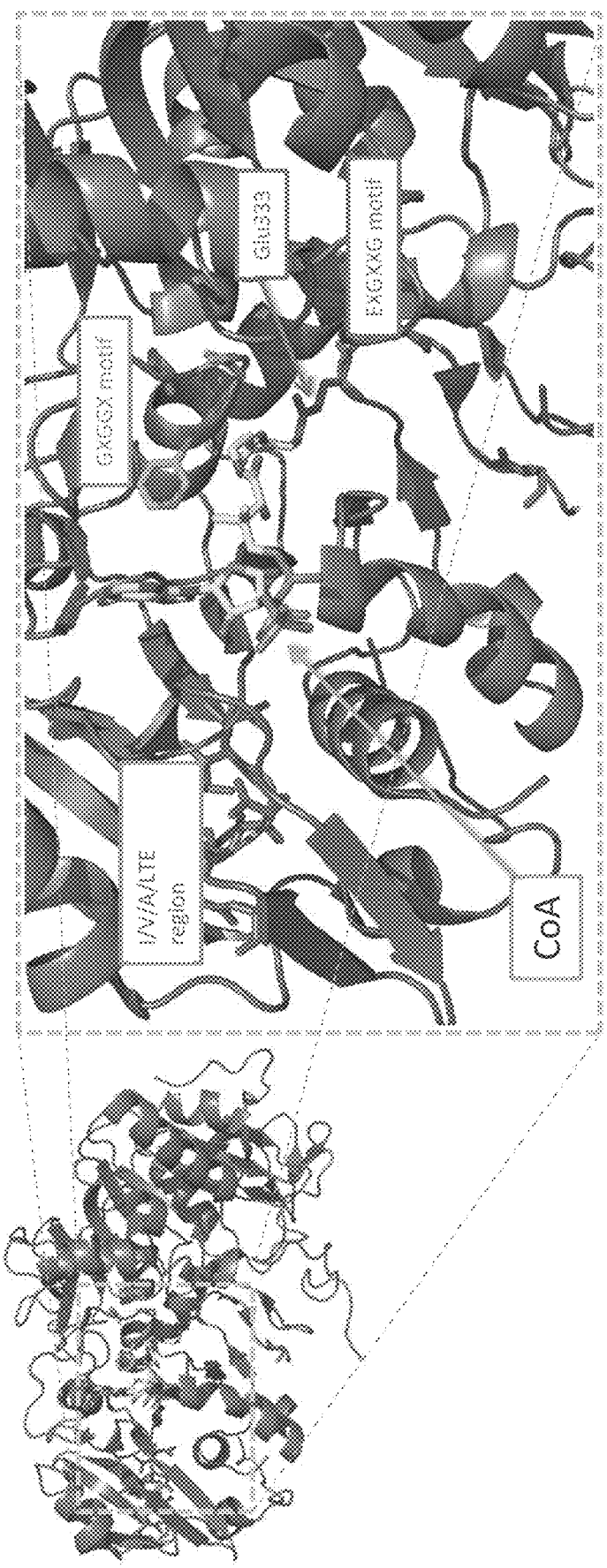
FIG. 3 is a graphical representation of the secondary and tertiary structure of an *E. coli* YdiF and potential CoA transferase active site.

In general, this document provides enzymes, non-naturally occurring pathways, cultivation strategies, feedstocks, non-naturally occurring host microorganisms, and attenuations to the host's biochemical network, for producing 3-oxopent-4-enoyl-CoA, 3-butene-2-one, 3-butene-2-ol, and/or butadiene from propenoate (also known as acrylate) or a salt form thereof (e.g., sodium propenoate) and acetyl-CoA using a polypeptide with both β-ketothiolase and CoA transferase activities.

Also provided are enzymes, non-naturally occurring pathways, cultivation strategies, feedstocks, non-naturally occurring host microorganisms, and attenuations to the host's biochemical network, for producing 3-oxo-acyl-CoA compounds of formula (IIa), such as 3-oxo-pentanoyl-CoA or 3-oxo-hexanoyl-CoA, from carboxylic acids of formula (Ia) or salt forms thereof (such as sodium propionate or sodium butyrate), and acetyl-CoA using a polypeptide with both β-ketothiolase and CoA transferase activities.

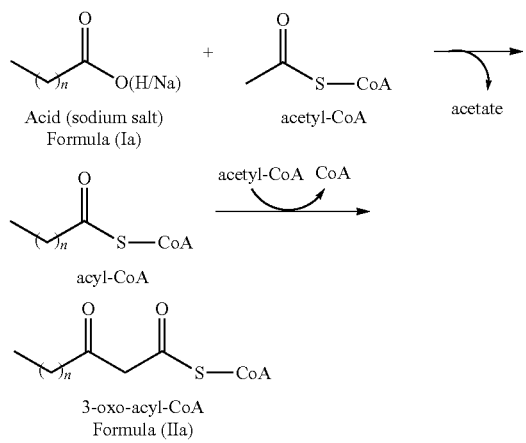

Also provided are enzymes, non-naturally occurring pathways, cultivation strategies, feedstocks, non-naturally occurring host microorganisms, and attenuations to the host's biochemical network, for producing 3-oxo-enoyl-CoA compounds of formula (IIb), such as 3-oxo-pent-4-enoyl-CoA, 3-oxo-hex-5-enoyl-CoA, 3-oxo-hept-6-enoyl-CoA, or 3-oxo-non-8-enoyl-CoA, from unsaturated carboxylic acids of formula (Ib), such as propenoate, 3-butenoate, 4-pentenoate, or 6-heptenoate, or salt forms thereof, and acetyl-CoA using a polypeptide with both β-ketothiolase and CoA transferase activities.

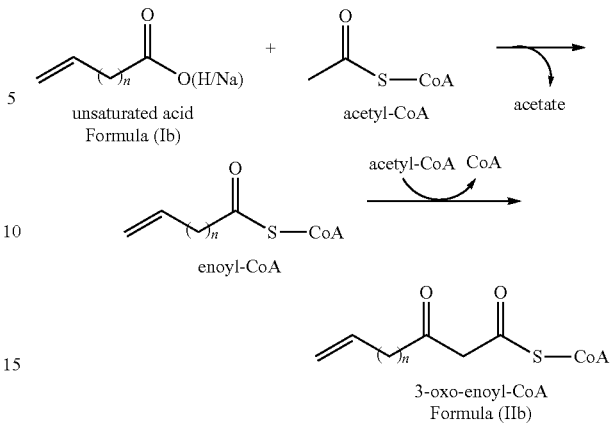

Also provided are enzymes, non-naturally occurring pathways, cultivation strategies, feedstocks, non-naturally occurring host microorganisms, and attenuations to the host's biochemical network, for producing 3-oxo-hydroxyacyl-CoA compounds of formula (IIc), such as 3-oxo-5-hydroxypentanoyl-CoA, 3-oxo-6-hydroxyhexanoyl-CoA, or 3-oxo-7-hydroxyheptanoyl-CoA, from hydroxy-substituted carboxylic acids of formula (Ic) or salt forms thereof (such as 3-hydroxypropionic acid, 4-hydroxybutyric acid, or 5-hydroxypentanoic acid), and acetyl-CoA using a polypeptide with both β-ketothiolase and CoA transferase activities.

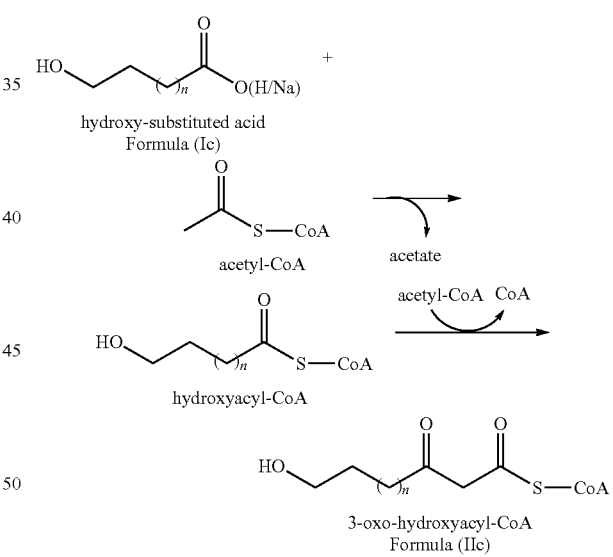

As used herein, the term "central precursor" is used to denote any metabolite in any metabolic pathway shown herein leading to the synthesis of propenoyl-CoA, 3-oxopent-4-enoyl-CoA, 3-butene-2-one, 3-butene-2-ol, or butadiene. The term "central metabolite" is used herein to denote a metabolite that is produced in all microorganisms to support growth.

Host microorganisms described herein can include endogenous pathways that can be manipulated such that propenoyl-CoA, 3-oxopent-4-enoyl-CoA, 3-butene-2-one, 3-butene-2-ol, or butadiene can be produced. In an endogenous pathway, the host microorganism naturally expresses all of the enzymes catalyzing the reactions within that pathway. A host microorganism containing an engineered pathway does not naturally express all of the enzymes catalyzing the reactions within that pathway but has been engineered such that all of the enzymes within the pathway are expressed in the host.

The term "exogenous" as used herein with reference to a nucleic acid (or a protein) and a host refers to a nucleic acid that does not occur in (and cannot be obtained from) a cell of that particular type as it is found in nature (or a protein encoded by such a nucleic acid). Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature, provided the nucleic acid as a whole does not exist in nature. For example, a nucleic acid molecule containing a genomic DNA sequence within an expression vector is a non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be a non-naturally-occurring nucleic acid. It follows that genomic DNA fragments produced by PCR or restriction endonuclease treatment as well as cDNAs are considered to be non-naturally-occurring nucleic acids since they exist as separate molecules not found in nature. It also follows that any nucleic acid containing a promoter sequence and polypeptide-encoding sequence (e.g., cDNA or genomic DNA) in an arrangement not found in nature is a non-naturally-occurring nucleic acid. A nucleic acid that is naturally-occurring can be exogenous to a particular host microorganism. For example, an entire chromosome isolated from a cell of yeast "x" is an exogenous nucleic acid with respect to a cell of yeast "y" once that chromosome is introduced into a cell of yeast "y."

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a cell of that same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, one or more of the following enzymes may be expressed in the host: a polypeptide with both β-ketothiolase and CoA transferase activities, a decarboxylase, a CoA transferase, an alcohol dehydrogenase, a carbonyl reductase, a phenylacetaldehyde reductase, and a linalool dehydratase. For example, a recombinant host can include a polypeptide with both CoA transferase and β-ketothiolase activities; a recombinant host can include a polypeptide with both CoA transferase and β-ketothiolase activities and a decarboxylase; a recombinant host can include a polypeptide with both CoA transferase and β-ketothiolase activities and a CoA transferase; a recombinant host can include a polypeptide with both CoA transferase and β-ketothiolase activities and an alcohol dehydrogenase or a phenylacetaldehyde reductase; a recombinant host can include a CoA transferase with both CoA transferase and β-ketothiolase activities and a linalool dehydratase; a recombinant host can include a polypeptide with both CoA transferase and β-ketothiolase activities, a CoA transferase, and a decarboxylase; a recombinant host can include a polypeptide with both CoA transferase and β-ketothiolase activities, a decarboxylase, and an alcohol dehydrogenase or a phenylacetaldehyde reductase; a recombinant host can include a polypeptide with both CoA transferase and β-ketothiolase activities, a decarboxylase, and a linalool dehydratase; a recombinant host can include a polypeptide with both CoA transferase and β-ketothiolase activities, a CoA transferase, and a linalool dehydratase; a recombinant host can include a polypeptide with both CoA transferase and β-ketothiolase activities, a CoA transferase, a decarboxylase, and a linalool dehydratase; a recombinant host can include a polypeptide with both CoA transferase and β-ketothiolase activities, a CoA transferase, a decarboxylase, an alcohol dehydrogenase, and a linalool dehydratase, or a recombinant host can include a polypeptide with both CoA transferase and β-ketothiolase activities, a CoA transferase, a decarboxylase, a phenylacetaldehyde reductase, and a linalool dehydratase.

For example, a recombinant host can include an exogenous polypeptide with both CoA transferase and β-ketothiolase activities and produce 3-oxopentanoyl-CoA from propionate (e.g., sodium propionate) and acetyl-CoA.

For example, a recombinant host can include an exogenous polypeptide with both CoA transferase and β-ketothiolase activities and produce 3-oxohexanoyl-CoA from butyrate (e.g., sodium butyrate) and acetyl-CoA.

For example, a recombinant host can include an exogenous polypeptide with both CoA transferase and β-ketothiolase activities and produce 3-oxo-hex-5-enoyl-CoA from 3-butenoate (e.g., sodium 3-butenoate) and acetyl-CoA.

For example, a recombinant host can include an exogenous polypeptide with both CoA transferase and β-ketothiolase activities and produce 3-oxo-hept-6-enoyl-CoA from 4-pentenoate (e.g., sodium 4-pentenoate) and acetyl-CoA.

For example, a recombinant host can include an exogenous polypeptide with both CoA transferase and β-ketothiolase activities and produce 3-oxo-non-8-enoyl-CoA from 6-heptenoate (e.g., sodium 6-heptenoate) and acetyl-CoA.

For example, a recombinant host can include an exogenous polypeptide with both CoA transferase and β-ketothiolase activities and produce 3-oxo-5-hydroxypentanoyl-CoA from 3-hydroxypropionic acid (e.g., sodium 3-hydroxypropionate) and acetyl-CoA. 3-oxo-5-hydroxypentanoyl-CoA is a useful intermediate for preparing nylon 5 compounds.

For example, a recombinant host can include an exogenous polypeptide with both CoA transferase and β-ketothiolase activities and produce 3-oxo-6-hydroxyhexanoyl-CoA from 4-hydroxybutyric acid (e.g., sodium 4-hydroxybutyrate) and acetyl-CoA. 3-oxo-6-hydroxyhexanoyl-CoA is a useful intermediate for preparing nylon 6 compounds. For example, 3-oxo-6-hydroxyhexanoyl-CoA can be converted to 6-hydroxyhexanoic acid, which can be converted to one or more of adipic acid, 6-aminohexanoic acid, hexamethylenediamine, caprolactam, and 1,6-hexanediol using one or more isolated enzymes such as dehydrogenases, reductases, hydratases, thioesterases, monooxygenases, and transaminases or using recombinant host cells expressing one or more such enzymes. For example, 3-oxo-6-hydroxyhexanoyl-CoA can be converted to one or more of adipic acid, 6-aminohexanoic acid, hexamethylenediamine, caprolactam, and 1,6-hexanediol according to methods described in U.S. Provisional Patent Application No. 62/079,903, whose disclosure is incorporated in its entirety by reference herein.

For example, a recombinant host can include an exogenous polypeptide with both CoA transferase and β-ketothiolase activities and produce 3-oxo-7-hydroxyheptanoyl-CoA from 5-hydroxypentanoic acid (e.g., sodium 5-hydroxypentanoate) and acetyl-CoA. 3-oxo-7-hydroxyheptanoyl-CoA is a useful intermediate for preparing nylon 7 compounds.

For example, a recombinant host can include an exogenous polypeptide with both CoA transferase and β-ketothiolase activities and produce 3-oxopent-4-enoyl-CoA from acrylate (e.g., sodium acrylate) and acetyl-CoA. 3-oxopent-4-enoyl-CoA can be converted to 3-butene-2-one and/or butadiene.

For example, a recombinant host can include an exogenous polypeptide with both CoA transferase and β-ketothiolase activities and an exogenous CoA transferase, and produce 3-oxopent-4-enoate, which can be converted to 3-butene-2-one, 3-buten-2-ol, and/or butadiene.

For example, a recombinant host can include an exogenous polypeptide with both CoA transferase and β-ketothiolase activities, an exogenous CoA transferase, and an exogenous decarboxylase and produce 3-butene-2-one, which can be converted to 3-butene-2-ol or butadiene.

For example, a recombinant host can include an exogenous polypeptide with both CoA transferase and β-ketothiolase activities, an exogenous CoA transferase, an exogenous decarboxylase, and an exogenous alcohol dehydrogenase or an exogenous phenylacetaldehyde reductase, and produce 3-butene-2-ol, which can be converted to butadiene.

For example, a recombinant host can include an exogenous polypeptide with both CoA transferase and β-ketothiolase activities, an exogenous CoA transferase, an exogenous decarboxylase, an exogenous alcohol dehydrogenase or an exogenous phenylacetaldehyde reductase, and an exogenous linalool dehydratase, and produce butadiene. In some embodiments, a recombinant host can include an exogenous polypeptide with both CoA transferase and β-ketothiolase activities, an exogenous CoA transferase, an exogenous decarboxylase, an exogenous alcohol dehydrogenase, and an exogenous linalool dehydratase, and produce butadiene. In some embodiments, a recombinant host can include an exogenous polypeptide with both CoA transferase and β-ketothiolase activities, an exogenous CoA transferase, an exogenous decarboxylase, an exogenous phenylacetaldehyde reductase, and an exogenous linalool dehydratase, and produce butadiene.

For example, a recombinant host can include an exogenous alcohol dehydrogenase or an exogenous phenylacetaldehyde reductase, and an exogenous linalool dehydratase, and produce butadiene.

Within an engineered pathway, the enzymes can be from a single source, i.e., from one species or genera, or can be from multiple sources, i.e., from different species or genera. Nucleic acids encoding the enzymes described herein have been identified from various organisms and are readily available in publicly available databases such as GenBank or EMBL.

Any of the enzymes described herein that can be used for production of one or more of 3-oxopentanoyl-CoA, 3-oxohexanoyl-CoA, 3-oxopent-4-enoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, 3-butene-2-ol, and/or butadiene, in vitro or in a recombinant host, can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of the corresponding wild-type enzyme. It will be appreciated that the sequence identity can be determined on the basis of the mature enzyme (e.g., with any signal sequence removed) or on the basis of the immature enzyme (e.g., with any signal sequence included). It also will be appreciated that the initial methionine residue may or may not be present on any of the enzyme sequences described herein.

For example, a polypeptide with both CoA transferase and β-ketothiolase activities described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Clostridium propionicum* (YdiF) (see GenBank Accession No. Q9L3F7, SEQ ID NO: 1), a *Clostridium aminobutyricum* (see GenBank Accession No. Q9RM86, SEQ ID NO: 19, a *Peptostreptococcaceae* (see Uniprot Accession No. U2L5C9, SEQ ID NO: 5); a Firmicutes bacterium (see Uniprot Accession No. R5ADR5, SEQ ID NO: 6), a *Megasphaera elsdenii* (see Uniprot Accession No. GOVND6, SEQ ID NO: 7), or a *Salmonella enterica* subsp. *houtenaeserovar* (see Uniprot Accession No. V1HBS2, SEQ ID NO: 9) acetate CoA transferase, or a modified *Clostridium propionicum* acetate CoA transferase having the amino acid sequence set forth in SEQ ID NO: 2. See FIG. 2.

For example, a CoA transferase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Escherichia coli* acetyl-CoA:acetoacetyl-CoA transferase encoded by atoAD (see GenBank Accession Nos. AAC75282.1 (beta subunit) and AAC75281.1 (alpha subunit), SEQ ID NOs: 10 and 11, respectively) or a *Pseudomonas putida* 3-oxoacid CoA-transferase encoded by pcaIJ (see Genbank Accession No. ACA73091.1 (A subunit) and ACA73090.1 (B subunit), SEQ ID NO: 12 and 13, respectively).

For example, a decarboxylase described herein such as an acetoacetate decarboxylase can have at least 70% sequence identity (homology) (e.g., at least 75%, 80%, 85%, 90%, 95%, 97%, 98%, 99%, or 100%) to the amino acid sequence of a *Chromobacterium violaceum* acetoacetate decarboxylase (see Genbank Accession No. AAQ61181.1, SEQ ID NO: 14) or a *Clostridium acetobutylicum* acetoacetate decarboxylase (Genbank Accession No. AAA63761.1, SEQ ID NO: 15). See, FIG. 2.

For example, an alcohol dehydrogenase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Nocardia rhamnosiphila* (for example GenBank Accession No. WP_030525792, SEQ ID NO: 16) alcohol dehydrogenase.

For example, a phenylacetaldehyde reductase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Rhodococcus* sp. ST-10 (for example GenBank Accession No. BAD51480, SEQ ID NO: 17) phenylacetaldehyde reductase.

For example, a linalool dehydratase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Castellaniella defragrans* (for example GenBank Accession No. CBW30776, SEQ ID NO: 18) linalool dehydratase. In one embodiment, a linalool dehydratase described herein can be a mutant of the linalool dehydratase from *Castellaniella defragrans*, for example one of the mutants described in U.S. Provisional Patent Application No. 62/126,279, whose disclosure is incorporated in its entirety by reference herein, or one of the mutants described in U.S. Provisional Patent Applications No. 62/126,299 or 62/126,315, whose disclosure is incorporated in its entirety by reference herein.

For example, a carbonyl reductase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Candida parapsilosis* (for example GenBank Accession No. AFD29185.1, SEQ ID NO: 20) carbonyl reductase.

The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be followed for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least 30%, 40%, 50%, 60%, 70%, 75%, 80%, 85%, 90%, 95%, 98%, 99%, 100%, or even greater than 100%) of the activity of the corresponding mature, full-length, wild-type protein. The functional fragment can generally, but not always, be comprised of a continuous region of the protein, wherein the region has functional activity.

Figure 4:
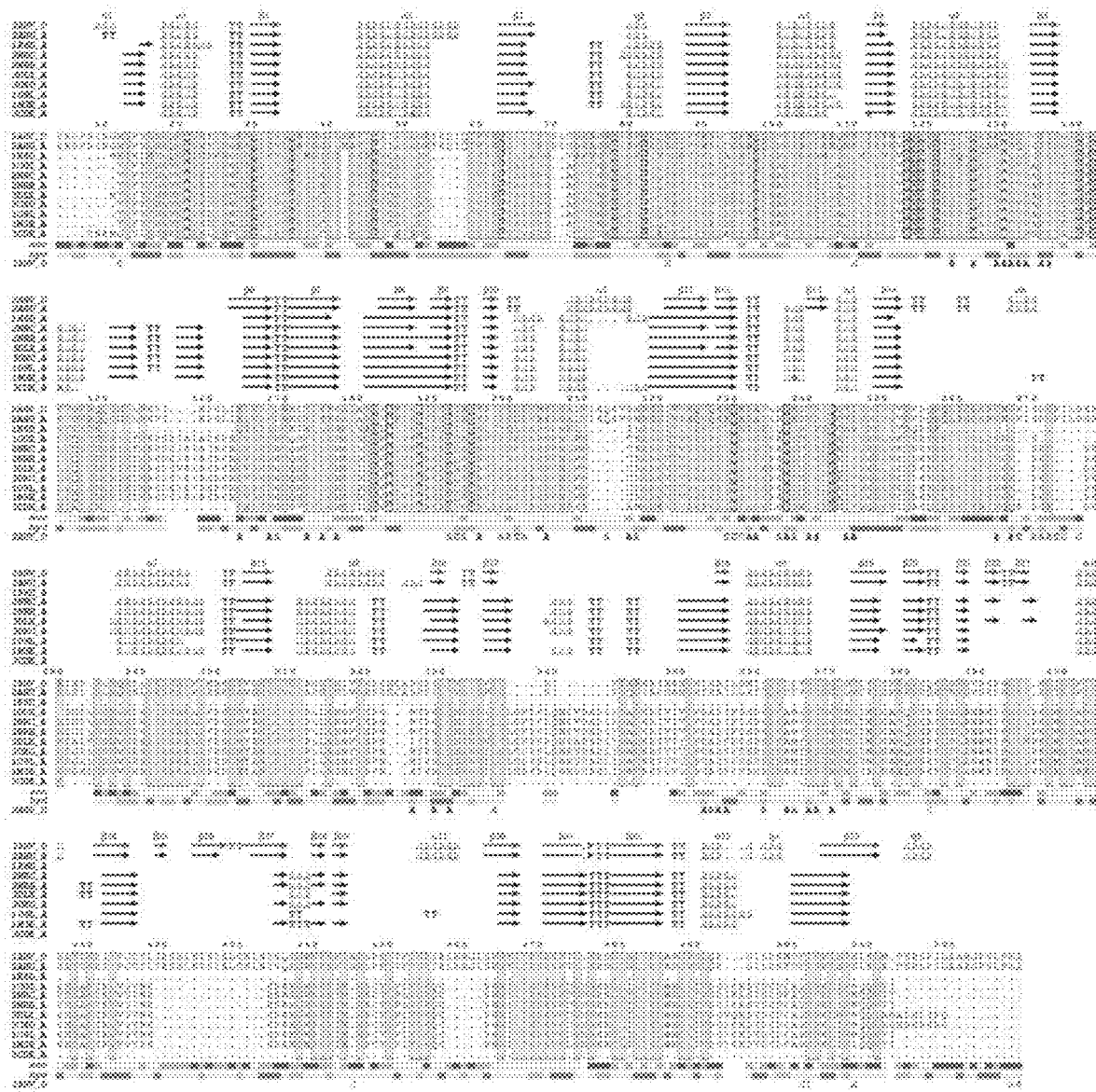
FIG. 4 reports the sequence alignment of *E. coli* 2AHV YdiF and 16 other polypeptides (SEQ ID NOS 23-33, respectively, in order of appearance).

The secondary structure of a known *E. coli* YdiF was analyzed along with that of other polypeptides known or expected to have dual CoA transferase and β-ketothiolase activities. A sequence alignment chart is provided in FIG. 4.

At least three conserved amino acid sequence motifs are thought to be associated with thiolase activity in polypeptides having dual CoA transferase and 3-ketothiolase activities: a EXGXXG motif, a GXGG(A/F) motif, and a I/V/A/LTE motif. See FIG. 4. The EXGXXG motif is associated with a turn between two beta sheets in the secondary structure of polypeptides having dual CoA transferase and β-ketothiolase activities. The GXGG(A/F) motif is associated with a strand before an alpha helix in the secondary structure of polypeptides having dual CoA transferase and β-ketothiolase activities. The I/V/A/LTE motif is associated with a strand between two beta sheets in the secondary structure of polypeptides having dual CoA transferase and β-ketothiolase activities.

All CoA transferases identified herein as having thiolase activity share the I/V/A/LTE motif. On this basis CoA transferase from *N. thermophilus* is likely to have ketothiolase activity if expressed in a thermophilic host and tested at elevated reaction temperature.

In at least one embodiment, the polypeptide having both CoA transferase and β-ketothiolase activities is a CoA transferase whose amino acid sequence includes the motifs EXGXXG and GXGG(A/F). In at least one embodiment, the polypeptide having both CoA transferase and β-ketothiolase activities is a CoA transferase whose amino acid sequence includes the motif I/V/A/LTE.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine, and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Any substitution of one member of the above-mentioned polar, basic, or acidic groups by another member of the same group can be deemed a conservative substitution. By contrast, a nonconservative substitution is a substitution of one amino acid for another with dissimilar characteristics.

In some embodiments, one or more mutations can be introduced into the polypeptide with both CoA transferase and β-ketothiolase activities (e.g., SEQ ID NOs: 1, 2, 5, 6, 7, 8, 9, 19) without impacting either activity. For example, a polypeptide with both CoA transferase and β-ketothiolase activities can have a substitution at one or more of positions 38, 60, 112, 258, and 390 without impacting either the CoA transferase or β-ketothiolase activity. For example, a polypeptide with both CoA transferase and β-ketothiolase activities can have a substitution of an alanine for any of the following residues: the serine at position 38, the serine at position 60, the cysteine at position 112, the cysteine at position 258, or the cysteine at position 390 of SEQ ID NO: 1, without affecting the β-ketothiolase or CoA transferase activity of the polypeptide. Residues 38, 60, 112, 258, and 390 have homology to the active site of other known β-ketothiolases. For example, a polypeptide with both CoA transferase and β-ketothiolase activities can have a substitution of a glycine for the glutamic acid at position 324 of SEQ ID NO:1 and maintain both activities. Position 324 was identified as the active site of the polypeptide for its CoA transferase activity. See, Selmer et al., *Eur. J. Biochem.*, 269:372-380 (2002).

In some embodiments, one or more mutations can be introduced into the polypeptide with both CoA transferase and β-ketothiolase activities to reduce or abolish one of the activities, as the active sites are independent of each other. For example, a polypeptide with both CoA transferase and β-ketothiolase activities can have a substitution of a leucine for the glutamic acid at position 324 of SEQ ID NO:1 to reduce the CoA transferase activity while maintaining the β-ketothiolase activity.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine (SEQ ID NO: 21), hemagglutinin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation, or ER or Golgi apparatus retention signals. Heterologous sequences can be of varying length and in some cases can be a longer sequences than the full-length target proteins to which the heterologous sequences are attached.

Engineered hosts can naturally express none or some (e.g., one or more, two or more, three or more, four or more, five or more, or six or more) of the enzymes of the pathways described herein. Thus, a pathway within an engineered host can include all exogenous enzymes, or can include both endogenous and exogenous enzymes. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. As described herein, recombinant hosts can include nucleic acids encoding one or more of a polypeptide with both β-ketothiolase and CoA transferase activities, an alcohol dehydrogenase, a phenylacetaldehyde reductase, a decarboxylase, and a linalool dehydratase as described herein.

In addition, the production of 3-oxopentanoyl-CoA, 3-oxohexanoyl-CoA, 3-oxopent-4-enoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, 3-butene-2-ol, and/or butadiene can be performed in vitro with the appropriate substrates (e.g., a short chain alkyl or alkenyl carboxylate or salt forms thereof such as sodium acrylate, sodium propioanate, or sodium butyrate, and a CoA source such as acetyl CoA) and using one or more of the isolated enzymes described herein, using a lysate (e.g., a cell lysate) from a host microorganism as a source of the enzymes, or using a plurality of lysates from different host microorganisms as the source of the enzymes.

The reactions of the pathways described herein can be performed in one or more host strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from any of the above types of host cells and used in a purified or semi-purified form. Moreover, such extracts include lysates (e.g. cell lysates) that can be used as sources of relevant enzymes. In the methods provided by the document, all the steps can be performed in host cells, all the steps can be performed using extracted enzymes, or some of the steps can be performed in cells and others can be performed using extracted enzymes.

Enzymes Generating Butadiene

As depicted in FIG. 1, butadiene can be biosynthesized from propenoate, for example sodium propenoate. Propenoate and acetyl-CoA can be condensed to propenoyl-CoA using a polypeptide with both CoA transferase and β-ketothiolase activities, for example a polypeptide classified under EC 2.8.3.-, for example a polypeptide classified under 2.8.3.8. For example, a polypeptide with both CoA transferase and β-ketothiolase activities can be classified under EC 2.8.3.8 such as the polypeptides from *Clostridium propionicum, Peptostreptococcaceae*, a Firmicutes bacterium, or a *Megasphaera elsdenii*, or classified under 2.8.3.-, such as the polypeptide from *Clostridium aminobutyricum*. Propenoyl-CoA can be converted to 3-oxopent-4-enoyl-CoA using a polypeptide with both CoA transferase and β-ketothiolase activities, for example a polypeptide classified under EC 2.8.3.-, for example a polypeptide classified under 2.8.3.8, for example the polypeptides from *Clostridium propionicum, Peptostreptococcaceae*, a Firmicutes bacterium, a *Megasphaera elsdenii*, or a *Salmonella enterica* subsp. *houtenaeserovar*. See, e.g., SEQ ID NOs: 1 and 5-9. See Table 1 for examples of such transferases. For example, the polypeptide with both CoA transferase and β-ketothiolase activities can be the product of the YdiF gene from *C. propionicum*.

In other embodiments, a polypeptide with both CoA transferase and β-ketothiolase activities can be classified under EC 2.8.3.1, EC 2.8.3.10, EC 2.8.3.11, EC 2.8.3.12, EC 2.8.3.13, EC 2.8.3.15, EC 2.8.3.16, EC 2.8.3.17, EC 2.8.3.18, EC 2.8.3.19, EC 2.8.3.20, EC 2.8.3.21, EC 2.8.3.5, EC 2.8.3.6, or EC 2.8.3.9. See Table 2 for examples of such transferases.

TABLE 1

| EC | Uniprot Gene Accession Number | Enzyme | Organism |
| --- | --- | --- | --- |
| 2.8.3.8 | Q9L3F7 | Acetate/Propionate CoA-transferase | Clostridium propionicum |
| 2.8.3.8 | V1HBS2 | Acetate CoA-transferase YdiF | Salmonella enterica subsp. houtenaeserovar |
| 2.8.3.8 | U2L5C9 | Acetate CoA-transferase YdiF | Peptostreptococcaceae bacterium oral taxon |
| 2.8.3.8 | R5ADR5 | Acetate CoA-transferase YdiF | Firmicutes bacterium CAG |
| 2.8.3.8 | G0VND6 | Acetate CoA-transferase YdiF | Megasphaera elsdenii DSM 20460 |

TABLE 2

| EC | Uniprot Gene Accession Number | Enzyme | Organism |
| --- | --- | --- | --- |
| 2.8.3.10 | J1G510 | Acetyl-CoA hydrolase/transferase | Citrobacter sp. A1 |
| 2.8.3.18 | B3EY95 | Succinyl-CoA:acetate CoA-transferase | Acetobacter aceti |
| 2.8.3.20 | A9WGE3 | Succinyl-CoA-D-citramalate CoA-transferase | Chloroflexus aurantiacus |
| 2.8.3.— | Q9RM86 | 4-Hydroxybutyrate-CoA transferase | Clostridium aminobutyricum |

In some embodiments, a CoA-transferase classified under, for example, EC 2.8.3.- (e.g., EC 2.8.3.8 or EC 2.8.3.6) such as the gene products of AtoAD (see SEQ ID NOs: 10 and 11) or pcaIJ (see SEQ ID NOs: 12 and 13) is used to hydrolyze the CoA moiety and convert 3-oxopent-4-enoyl-CoA to 3-oxopent-4-enoate.

In some embodiments, a decarboxylase such as an acetoacetate decarboxylase classified, for example, under EC 4.1.1.4 can be used to remove the carboxy group from 3-oxopent-4-enoate to produce 3-buten-2-one. For example, a suitable acetoacetate decarboxylase can have at least 70% sequence identity to the amino acid sequence set forth in SEQ ID NO: 14 or SEQ ID NO: 15. This reaction also can occur spontaneously.

In some embodiments, an alcohol dehydrogenase classified under EC 1.1.1.- such as an alcohol dehydrogenase from *Nocardia rhamnosiphila* can be used to convert 3-buten-2-one to 3-buten-2-ol. For example, a suitable alcohol dehydrogenase can have at least 70% sequence identity to the amino acid sequence set forth in SEQ ID NO: 16.

In some embodiments, a carbonyl reductase classified under EC 1.1.1.184 such as the carbonyl reductase from *Candida parapsilosis* can be used to convert 3-buten-2-one to 3-buten-2-ol. For example, a suitable carbonyl reductase can have at least 70% sequence identity to the amino acid sequence set forth in SEQ ID NO:20.

In some embodiments, a phenylacetaldehyde reductase classified under EC 1.2.1.39 such as an phenylacetaldehyde reductase from *Rhodococcus* sp. ST-10 can be used to convert 3-buten-2-one to 3-buten-2-ol. For example, a suitable phenylacetaldehyde reductase can have at least 70% sequence identity to the amino acid sequence set forth in SEQ ID NO: 17.

In some embodiments, a dehydratase enzyme classified in EC 4.2.1.-, such as linalool dehydratase classified, for example, under EC 4.2.1.127, for example a *Castellaniella defragrans* linalool dehydratase, can be used to convert 3-buten-2-ol to butadiene. For example, a suitable linalool dehydratase can have at least 70% sequence identity to the amino acid sequence set forth in SEQ ID NO: 18.

Biochemical Pathways to Butadiene

In some embodiments, propenoate, for example sodium propenoate, and acetyl-CoA are condensed to propenoyl-CoA using a polypeptide with both CoA transferase and β-ketothiolase activities, for example an enzyme classified under EC 2.8.3.-, for example an enzyme classified under 2.8.3.8; then propenoyl-CoA is converted to 3-oxopent-4-enoyl-CoA using a polypeptide with both CoA transferase and β-ketothiolase activities, for example an enzyme classified under EC 2.8.3.-, for example an enzyme classified under 2.8.3.8; followed by conversion of 3-oxopent-4-enoyl-CoA to 3-oxopent-4-enoate by a CoA transferase classified, for example, under 2.8.3.8 or EC 2.8.3.6; followed by conversion of 3-oxopent-4-enoate to 3-butene-2-one either spontaneously or by a decarboxylase classified, for example, under EC 4.1.1.4; followed by conversion of 3-butene-2-one to 3-buten-2-ol by an alcohol dehydrogenase classified, for example, under EC 1.1.1.-, or a phenylacetaldehyde reductase classified, for example, under EC 1.2.1.39; followed by conversion of 3-buten-2-ol to 1,3-butadiene by a linalool dehydratase classified, for example, under EC 4.2.1.127.

Cultivation Strategy

In some embodiments, one or more of 3-oxopent-4-enoyl-CoA, 3-oxopentanoyl-CoA, 3-oxohexanoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, 3-buten-2-ol, and butadiene are biosynthesized in a recombinant host using anaerobic, aerobic, or micro-aerobic cultivation conditions. In some embodiments, the cultivation strategy entails nutrient limitation such as nitrogen, phosphate, or oxygen limitation.

In some embodiments, a cell retention strategy using, for example, ceramic hollow fiber membranes can be employed to achieve and maintain a high cell density during either fed-batch or continuous fermentation.

In some embodiments, the principal carbon source fed to the fermentation in the synthesis of one or more of 3-oxopent-4-enoyl-CoA, 3-oxopentanoyl-CoA, 3-oxohexanoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, 3-buten-2-ol, and butadiene can derive from biological or non-biological feedstocks.

In some embodiments, the biological feedstock can be, or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli*, *Cupriavidus neca-*

*tor, Pseudomonas oleavorans, Pseudomonas putida*, and *Yarrowia lipolytica* (Lee et al., *Appl. Biochem. Biotechnol.*, 2012, 166:1801-1813; Yang et al., *Biotechnology for Biofuels*, 2012, 5:13; Meijnen et al., *Appl. Microbiol. Biotechnol.*, 2011, 90:885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, 2011, supra; Martin and Prather, *J. Biotechnol.*, 2009, 139:61-67).

The efficient catabolism of lignin-derived aromatic compounds such as benzoate analogues has been demonstrated in several microorganisms such as *Pseudomonas putida* and *Cupriavidus necator* (Bugg et al., *Current Opinion in Biotechnology*, 2011, 22, 394-400; Pérez-Pantoja et al., *FEMS Microbiol. Rev.*, 2008, 32, 736-794).

The efficient utilization of agricultural waste, such as olive mill waste water, has been demonstrated in several microorganisms, including *Yarrowia lipolytica* (Papanikolaou et al., *Bioresour. Technol.*, 2008, 99(7):2419-2428).

The efficient utilization of fermentable sugars such as monosaccharides and disaccharides derived from cellulosic, hemicellulosic, cane and beet molasses, cassava, corn, and other agricultural sources has been demonstrated for several microorganism such as *Escherichia coli, Corynebacterium glutamicum, Lactobacillus delbrueckii* and *Lactococcus lactis* (see, e.g., Hermann et al, *J. Biotechnol.*, 2003, 104:155-172; Wee et al., *Food Technol. Biotechnol.*, 2006, 44(2): 163-172; Ohashi et al., *J. Bioscience and Bioengineering*, 1999, 87(5):647-654).

The efficient utilization of furfural, derived from a variety of agricultural lignocellulosic sources, has been demonstrated for *Cupriavidus necator* (Li et al., *Biodegradation*, 2011, 22:1215-1225).

In some embodiments, the non-biological feedstock can be or can derive from natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

The efficient catabolism of methanol has been demonstrated for the methylotrophic yeast *Pichia pastoris*.

The efficient catabolism of ethanol has been demonstrated for *Clostridium kluyvenri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., Energy, Sustainability and Society, 2012, 2:11).

The efficient catabolism of syngas has been demonstrated for numerous microorganisms, such as *Clostridium ljungdahlii* and *Clostridium autoethanogenum* (Köpke et al., Applied and Environmental Microbiology, 2011, 77(15): 5467-5475).

The efficient catabolism of the non-volatile residue waste stream from cyclohexane processes has been demonstrated for numerous microorganisms, such as *Delftia acidovorans* and *Cupriavidus necator* (Ramsay et al., Applied and Environmental Microbiology, 1986, 52(1):152-156).

In some embodiments, the host microorganism is a prokaryote. For example, the prokaryote can be a bacterium from the genus *Escherichia* such as *Escherichia coli*; from the genus *Clostridia* such as *Clostridium ljungdahlii, Clostridium autoethanogenum* or *Clostridium kluyveri*; from the genus *Corynebacteria* such as *Corynebacterium glutamicum*; from the genus *Cupriavidus* such as *Cupriavidus necator*, or *Cupriavidus metallidurans*; from the genus *Pseudomonas* such as *Pseudomonas fluorescens, Pseudomonas putida*, or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing one or more of 3-oxopent-4-enoyl-CoA, 3-oxopentanoyl-CoA, 3-oxohexanoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, 3-butene-2-ol, and butadiene.

In some embodiments, the host microorganism is a eukaryote. For example, the eukaryote can be a filamentous fungus, e.g., one from the genus *Aspergillus* such as *Aspergillus niger*. Alternatively, the eukaryote can be a yeast, e.g., one from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing 3-oxopent-4-enoyl-CoA, 3-oxopentanoyl-CoA, 3-oxohexanoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, 3-butene-2-ol, and/or butadiene.

Metabolic Engineering

The present document provides methods involving less than all the steps described for all the pathways disclosed herein. Such methods can involve, for example, one, two, three, four, five, six, seven, eight, nine, ten, eleven, twelve or more of such steps. Where less than all the steps are included in such a method, the first, and in some embodiments the only, step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host. This document provides host cells of any of the genera and species listed and genetically engineered to express one or more (e.g., two, three, four, five, six, seven, eight, nine, 10, 11, 12, or more) recombinant forms of any of the enzymes recited in the document. Thus, for example, the host cells can contain exogenous nucleic acids encoding enzymes catalyzing one or more of the steps of any of the pathways described herein.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described as accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different cofactors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined here can be gene dosed, i.e., overexpressed, into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to 3-oxopent-4-enoyl-CoA, 3-oxopentanoyl-CoA, 3-oxohexanoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, 3-butene-2-ol, and/or butadiene.

Attenuation strategies include, but are not limited to: the use of transposons, homologous recombination (double cross-over approach), mutagenesis, enzyme inhibitors, and RNAi interference.

In some embodiments, fluxomic, metabolomic, and transcriptomal data can be utilized to inform or support genome-scale system biology techniques, thereby devising genome scale attenuation or knockout strategies in directing carbon flux to 3-oxopent-4-enoyl-CoA, 3-oxopentanoyl-CoA, 3-oxohexanoyl-CoA, 3-oxo-hex-5-enoyl-CoA, 3-oxo-hept-6-enoyl-CoA, 3-oxo-non-8-enoyl-CoA, 3-oxo-6-hydroxyhexanoyl-CoA, 3-butene-2-one, 3-butene-2-ol, and/or butadiene.

In some embodiments, the host microorganism's tolerance to high concentrations of 3-oxopent-4-enoyl-CoA, 3-oxopentanoyl-CoA, 3-oxohexanoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, and/or butadiene can be improved through continuous cultivation in a selective environment.

In some embodiments, the host microorganism's endogenous biochemical network can be attenuated or augmented to (1) ensure the intracellular availability of acetyl-CoA and 2-oxoglutarate, (2) create an NADH or NADPH imbalance that may only be balanced via the formation of one or more of 3-oxopent-4-enoyl-CoA, 3-butene-2-one, and butadiene, (3) prevent degradation of central metabolites, or central precursors leading to and including one or more of 3-oxopent-4-enoyl-CoA, 3-oxopentanoyl-CoA, 3-oxohexanoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, 3-butene-2-ol, and butadiene and/or (4) ensure efficient efflux from the cell.

In some embodiments requiring intracellular availability of acetyl-CoA for 3-oxopent-4-enoyl-CoA, 3-oxopentanoyl-CoA, 3-oxohexanoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, 3-butene-2-ol, and/or butadiene synthesis, endogenous enzymes catalyzing the hydrolysis of acetyl-CoA such as short-chain length thioesterases can be attenuated in the host organism.

In some embodiments requiring the intracellular availability of acetyl-CoA for 3-oxopent-4-enoyl-CoA, 3-oxopentanoyl-CoA, 3-oxohexanoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, 3-butene-2-ol, and/or butadiene synthesis, an endogenous phosphotransacetylase generating acetate such as pta can be attenuated (Shen et al., *Appl. Environ. Microbiol.*, 2011, 77(9):2905-2915).

In some embodiments requiring the intracellular availability of acetyl-CoA for 3-oxopent-4-enoyl-CoA, 3-oxopentanoyl-CoA, 3-oxohexanoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, and/or butadiene synthesis, an endogenous gene in an acetate synthesis pathway encoding an acetate kinase, such as ack, can be attenuated.

In some embodiments requiring the intracellular availability of acetyl-CoA and NADH for 3-oxopent-4-enoyl-CoA, 3-butene-2-one, 3-butene-2-ol, and/or butadiene synthesis, an endogenous gene encoding an enzyme that catalyzes the degradation of pyruvate to lactate such as lactate dehydrogenase encoded by ldhA can be attenuated (Shen et al., 2011, supra).

In some embodiments, enzymes that catalyze anaplerotic reactions such as PEP carboxylase and/or pyruvate carboxylase can be overexpressed in the host organism.

In some embodiments requiring the intracellular availability of acetyl-CoA and NADH for 3-oxopent-4-enoyl-CoA, 3-butene-2-one, 3-butene-2-ol, and/or butadiene synthesis, endogenous genes encoding enzymes, such as menaquinol-fumarate oxidoreductase, that catalyze the degradation of phophoenolpyruvate to succinate such as frdBC can be attenuated (see, e.g., Shen et al., 2011, supra).

In some embodiments requiring the intracellular availability of acetyl-CoA and NADH for 3-oxopent-4-enoyl-CoA, 3-butene-2-one, 3-butene-2-ol, and/or butadiene synthesis, an endogenous gene encoding an enzyme that catalyzes the degradation of acetyl-CoA to ethanol such as the alcohol dehydrogenase encoded by adhE can be attenuated (Shen et al., 2011, supra).

In some embodiments, where pathways require excess NADH co-factor for 3-oxopent-4-enoyl-CoA, 3-butene-2-one, 3-butene-2-ol, and/or butadiene synthesis, a recombinant formate dehydrogenase gene can be overexpressed in the host organism (Shen et al., 2011, supra).

In some embodiments, where pathways require excess NADH co-factor for 3-oxopent-4-enoyl-CoA, 3-butene-2-one, 3-butene-2-ol, and/or butadiene synthesis, a recombinant NADH-consuming transhydrogenase can be attenuated.

In some embodiments, an endogenous gene encoding an enzyme that catalyzes the degradation of pyruvate to ethanol such as pyruvate decarboxylase can be attenuated.

In some embodiments requiring the intracellular availability of acetyl-CoA for 3-oxopent-4-enoyl-CoA, 3-oxopentanoyl-CoA, 3-oxohexanoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, 3-butene-2-ol, and/or butadiene synthesis, a recombinant acetyl-CoA synthetase such as the gene product of acs can be overexpressed in the microorganism (Satoh et al., *J. Bioscience and Bioengineering*, 2003, 95(4):335-341).

In some embodiments, carbon flux can be directed into the pentose phosphate cycle to increase the supply of NADPH by attenuating an endogenous glucose-6-phosphate isomerase (EC 5.3.1.9).

In some embodiments, carbon flux can be redirected into the pentose phosphate cycle to increase the supply of NADPH by overexpression a 6-phosphogluconate dehydrogenase and/or a transketolase (Lee et al., 2003, *Biotechnology Progress*, 19(5), 1444-1449).

In some embodiments, where pathways require excess NADPH co-factor in the synthesis of 3-oxopent-4-enoyl-CoA, 3-butene-2-one, 3-butene-2-ol, and/or butadiene, a gene such as UdhA encoding a puridine nucleotide transhydrogenase can be overexpressed in the host organisms (Brigham et al., *Advanced Biofuels and Bioproducts*, 2012, Chapter 39, 1065-1090).

In some embodiments, where pathways require excess NADPH co-factor in the synthesis of 3-oxopent-4-enoyl-CoA, 3-butene-2-one, 3-butene-2-ol, and/or butadiene, a recombinant glyceraldehyde-3-phosphate-dehydrogenase gene such as GapN can be overexpressed in the host organisms (Brigham et al., 2012, supra).

In some embodiments, where pathways require excess NADPH co-factor in the synthesis of 3-oxopent-4-enoyl-CoA, 3-butene-2-one, 3-butene-2-ol, and/or butadiene, a recombinant malic enzyme gene such as maeA or maeB can be overexpressed in the host organisms (Brigham et al., 2012, supra).

In some embodiments, where pathways require excess NADPH co-factor in the synthesis of 3-oxopent-4-enoyl-CoA, 3-butene-2-one, 3-butene-2-ol, and/or butadiene, a recombinant glucose-6-phosphate dehydrogenase gene such as zwf can be overexpressed in the host organisms (Lim et al., *J. Bioscience and Bioengineering*, 2002, 93(6), 543-549).

In some embodiments, where pathways require excess NADPH co-factor in the synthesis of 3-oxopent-4-enoyl-CoA, 3-butene-2-one, 3-butene-2-ol, and/or butadiene, a recombinant fructose 1,6 diphosphatase gene such as fbp can be overexpressed in the host organisms (Becker et al., *J. Biotechnol.*, 2007, 132:99-109).

In some embodiments, where pathways require excess NADPH co-factor in the synthesis of 3-oxopent-4-enoyl-CoA, 3-butene-2-one, 3-butene-2-ol, and/or butadiene, endogenous triose phosphate isomerase (EC 5.3.1.1) can be attenuated.

In some embodiments, where pathways require excess NADPH co-factor in the synthesis of 3-oxopent-4-enoyl-CoA, 3-butene-2-one, 3-butene-2-ol, and/or butadiene, a recombinant glucose dehydrogenase such as the gene product of gdh can be overexpressed in the host organism (Satoh et al., *J. Bioscience and Bioengineering*, 2003, 95(4):335-341).

In some embodiments, endogenous enzymes facilitating the conversion of NADPH to NADH can be attenuated, such as the NADH generation cycle that may be generated via inter-conversion of glutamate dehydrogenases classified under EC 1.4.1.2 (NADH-specific) and EC 1.4.1.4 (NADPH-specific).

In some embodiments, an endogenous glutamate dehydrogenase (EC 1.4.1.3) that utilizes both NADH and NADPH as co-factors can be attenuated.

In some embodiments using hosts that naturally accumulate polyhydroxyalkanoates, the endogenous polymer synthase enzymes can be attenuated in the host strain.

In some embodiments, enzymes such as a pimeloyl-CoA dehydrogenase classified under, EC 1.3.1.62; an acyl-CoA dehydrogenase classified, for example, under EC 1.3.8.7, EC 1.3.8.1, or EC 1.3.99.-; and/or a butyryl-CoA dehydrogenase classified, for example, under EC 1.3.8.6, that degrade central metabolites and central precursors leading to and including 3-oxopent-4-enoyl-CoA, 3-butene-2-one, 3-butene-2-ol, and/or butadiene can be attenuated.

In some embodiments, endogenous enzymes activating 3-oxopent-4-enoyl-CoA, 3-butene-2-one, 3-butene-2-ol, and/or butadiene precursors via Coenzyme A esterification such as CoA-ligases (e.g., an adipyl-CoA synthetase) classified under, for example, EC 6.2.1.- can be attenuated.

In some embodiments, the efflux of 3-oxopent-4-enoyl-CoA, 3-butene-2-one, 3-butene-2-ol, and/or butadiene across the cell membrane to the extracellular media can be enhanced or amplified by genetically engineering structural modifications to the cell membrane or increasing any associated transporter activity for 3-oxopent-4-enoyl-CoA, 3-butene-2-one, 3-butene-2-ol, and/or butadiene.

Producing 3-Oxopent-4-Enoyl-CoA, 3-Oxopentanoyl-CoA, 3-Oxohexanoyl-CoA, 3-Oxo-Hex-5-Enoyl-CoA, 3-Oxo-Hept-6-Enoyl-CoA, 3-Oxo-Non-8-Enoyl-CoA, 3-Oxo-5-Hydroxypentanoyl-CoA, 3-Oxo-6-Hydroxyhexanoyl-CoA, 3-Oxo-7-Hydroxyheptanoyl-CoA, 3-Butene-2-One, 3-Butene-2-Ol, or Butadiene Using a Recombinant Host Typically, one or more of 3-oxopent-4-enoyl-CoA, 3-oxopentanoyl-CoA, 3-oxohexanoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, 3-butene-2-ol, or butadiene can be produced by providing a host microorganism and culturing the provided microorganism with a culture medium containing a suitable carbon source as described above. In general, the culture media and/or culture conditions can be such that the microorganisms grow to an adequate density and produce 3-oxopent-4-enoyl-CoA, 3-oxopentanoyl-CoA, 3-oxohexanoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, 3-butene-2-ol, and/or butadiene efficiently. For large-scale production processes, any method can be used such as those described elsewhere (Manual of Industrial Microbiology and Biotechnology, $2^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of 3-oxopent-4-enoyl-CoA, 3-oxopentanoyl-CoA, 3-oxohexanoyl-CoA, 3-oxo-hex-5-enoyl-CoA, 3-oxo-hept-6-enoyl-CoA, 3-oxo-non-8-enoyl-CoA, 3-oxo-5-hydroxypentanoyl-CoA, 3-oxo-6-hydroxyhexanoyl-CoA, 3-oxo-7-hydroxyheptanoyl-CoA, 3-butene-2-one, 3-butene-2-ol, and/or butadiene. Once produced, any method can be used to isolate 3-oxopent-4-enoyl-CoA, 3-butene-2-one, and/or butadiene. For example, 3-oxopent-4-enoyl-CoA, 3-butene-2-one, 3-butene-2-ol, and/or butadiene can be recovered selectively from the fermentation broth via adsorption processes. The resulting eluate may be further concentrated via evaporation, crystallized via evaporative and/or cooling crystallization, and the crystals recovered via centrifugation. Distillation may be employed to achieve the desired product purity.

The invention will be further described in the following examples, which do not limit the scope of the invention described in the claims.

EXAMPLES

Example 1: Preparation of YdiF Mutants

YdiF mutants were prepared using the relevant primers to introduce the mutated bases via the Quick change lightning kit (Agilent, code product: 210518-5), and cloned into *E. coli*. In addition, all the proteins used in this experiment have the following extra amino acids added in the N-terminal extremity of the original protein sequence (SEQ ID NO:1): MGHHHHHHSSGLVPRGS. Those additional amino acids correspond to: two amino acids (M and G), a 6×His-tag followed by a 3 amino acids linker (SSG), and a specific proteolytic cleavage site (thrombin site, underlined) (SEQ ID NO: 22). All the sequences were confirmed by DNA sequencing.

From a fresh LB plate containing the desired clone transformant, one colony (or small scratch) was picked to inoculate 25 mL of LB supplemented with the relevant antibiotic and the pre-culture was incubated overnight at 37° C., 230 rpm. The following morning, the TB auto-induced medium (Merck/Code product: 71491-5) was prepared by mixing 60 g TB/L supplemented with 10 mL Glycerol/L of TB and microwaved during 3+2 minutes at full power. The TB was cooled down before use and splitting it in sterile flasks. Then, the pre-culture incubated overnight in LB was centrifuged and the supernatant discarded. The obtained pellet was resuspended with 5 mL of freshly prepared TB medium and used to inoculate 500 mL of TB dispensed in sterile flasks and supplemented with the appropriate antibiotic. The inoculated medium was incubated at 28° C. for at least 20 h, 230 rpm.

The culture was centrifuged at least at 3000 g/20 min/4° C. and the pellet used immediately or stored at −80'C.

The pellets (fresh or thawed) were resuspended in 10 to 20 mL of Buffer A (50 mM Hepes+150 mM NaCl+40 mM Imidazole+5% Glycerol–pH 7.5). The resuspended cells were then sonicated in ice for, 5 min at 37% Amplitude with 5" ON and 15" OFF sonication pulse. The sonicated cells were centrifuged for at least 20 min at 15500 g and 4° C. The supernatant containing the soluble fraction of proteins was recovered, filtered using 0.45 or 0.2 um filters, and used for His-trap protein purification.

The filtered soluble fraction of proteins obtained after extraction of proteins by sonication was used for His-tag protein purification. A 1 mL His-trap (GE Healthcare/Code product: 17-5319-01) column was equilibrated with 5-10 volumes column (VC) using Buffer A*. The soluble fraction of proteins was loaded onto the His-trap column manually using a syringe and 5-10 VC of Buffer A were used to wash the His-trap column. 5-10 VC of Buffer B** were used to elute the His-tag protein directly to a 4 or 20 mL centrifugal filtration unit (VWR/Code product: 512-2850) with a relevant cut-off (5 kD).

The centrifugal filtration unit was centrifuged at 3500 g/5° C. to a volume lower than 400 uL concentrate. Around 3 mL of Buffer C*** was added to the concentrate and the centrifugal filtration unit was again centrifuged at 3500 g/5° C. to a volume lower than 400 uL. This step was made to remove most of the imidazole used in Buffer B to elute the His-tag.

The concentrate of pure enzyme was recovered and Buffer C was used to top-up to the desired volume.

The concentration was checked using a Nanodrop spectrophotometer.

* Buffer A=50 mM Hepes+150 mM NaCl+40 mM Imidazole+5% (v/v) Glycerol–pH 7.5
** Buffer B=Buffer A+400 mM Imidazole–pH7.5
*** Buffer C=Buffer A without Imidazole–pH7.5

Example 2: Biotransformation Using YdiF or Mutants

Acetyl-CoA was used at a final concentration of 1.5 mM and 30 mM of the substrate being studied (e.g. carboxylic acid salts, such as sodium acrylate) or 1.5 mM of propionyl-CoA in 50 mM Hepes buffer (pH 7.5). The reaction was started by addition of 0.5 mg/mL of YdiF pure protein or mutants to a final volume of 250 µL and incubated for 1 to 10 hours at 30° C.

Two controls were made from similar mixture except that the enzymes were inactivated by heating-up at 95° C. for 20 min or they were replaced by Buffer C.

All samples were prepared in triplicate and spun down at 15000 g for 20 min at 4° C. Detection of the thiol product (e.g. acryloyl-CoA) synthesized from CoA-transferase activity and the keto-thiol product (e.g. 3-oxopent-4-enoyl-CoA) due to putative thiolase activity of YdiF (or homologues) was carried out by Liquid Chromatography coupled to a qTof-Mass spectrometry (in positive mode), using a C18 column (Zorbax Eclipse C18, 2.1×50 mm, 1.8µ, Agilent, code product: 959757-902) and a gradient of 10 mM ammonium acetate and acetonitrile as mobile phase.

Propionyl-CoA and butyryl-CoA (from Sigma-Aldrich) were used as authentic standards of the some of the reactions and were analyzed by LC-qTof-MS under the same conditions mentioned above.

Example 3: Evaluation of Potential Active Sites

Mutations were introduced as described in Example 1 at the following positions previously found to be potentially involved in the active site of other β-ketothiolases: C258A, S60A, C112A, S38A, C390A. Activity of the mutant enzymes was studied as described in Example 2. None of the mutations abolished the transferase and thiolase activity of YdiF.

Mutations were introduced as described in Example 1 to replace the glutamate in position 324 of YdiF (see Selmer et al., 2002) with glycine (mutant E324G) or leucine (E324L). Activity of the mutant enzymes was studied as described in Example 2. Abolition of transferase activity in these mutants showed that the glutamate at position 324 is present in the active site involved in the transferase activity of YdiF. The activity of mutant E324L was only partially abolished in comparison to mutant E324G, possibly due to a steric effect of the glutamate in the active site. Providing the mutant E324G with propionyl-CoA and acetyl-CoA showed the presence of the keto-thiol product (3-oxopentanoyl-CoA), consistent with the transferase activity and the β-ketothiolase activity of YdiF being independent and the involvement of separate active sites for those activities.

It was concluded the active site involved in the thiolase activity of YdiF presents new features in comparison to the β-ketothiolases already known. Oligomerisation of YdiF may also create an active site at the interfaces.

Example 4

YdiF from *Clostridium propionicum* belongs to the enzymatic class EC2.8.3.8. Other members of this enzyme class with similar structural features to YdiF, as well as proteins with a CoA-transferase activity from close-by enzymatic classes, were screened for dual transferase/ketothiolase activity as described in Example 2. Acetyl-CoA and sodium acrylate were provided as substrates. LC-MS was used to detect the thiol-product (propenoyl-CoA) synthesized via the transferase activity and the ketothiol-product (3-oxopent-4-enoyl-CoA) synthesized via the thiolase activity, as described in Example 2. Results are presented in Table 3.

Example 5

To study the substrate specificity of YdiF, several commercially available substrates were provided to YdiF (and homologues) in combination with acetyl-CoA, as described in Example 2. LC-MS was used to detect the thiol-product synthesized via the transferase activity and the ketothiol-product synthesized via the thiolase activity. Results are presented in Table 4.

Dual transferase/ketothiolase activity was observed with use of C3- and C4-saturated substrates as well as with medium-length unsaturated substrates, without obvious inhibition effects due to any of the products. 4-Hydroxybutyrate was used as a substrate with acetyl-CoA for protein 244 and the corresponding products from the transferase and ketothiolase activities of protein 244 were detected.

TABLE 3

| EC | Gene (Uniprot) | Bdigene | Protein | Organism | Solubility | thiol-product | ketothiol-product |
|---|---|---|---|---|---|---|---|
| 2.8.18 | Q9L3F7 | 237 | Acetate/Propionate CoA-transferase | *Clostridium propionicum* | ✓ | ✓ | ✓ |
| 2.8.3.8 | V1HBS2 | 271 | Acetate CoA-transferase YdiF | *Salmonella enterica* subsp. *houtenaeserovar* | ✓ | ✓ | ✓ |
| 2.8.18 | U2L5C9 | 272 | Acetate CoA-transferase YdiF | *Peptostreptococcaceae bacterium oral taxon* | ✓ | ✓ | ✓ |
| 2.8.3.8 | R5ADR5 | 273 | Acetate CoA-transferase YdiF | *Firmicutes bacterium* CAG | ✓ | ✓ | ✓ |
| 2.8.3.8 | G0VND6 | 274 | Acetate CoA-transferase YdiF | *Megasphaera elsdenii* DSM 20460 | ✓ | ✓ | ✓ |
| 2.8.1.16 | C6VTZ3 | 275 | Acetyl-CoA acetyltransferase | *Dyadobacter fermentans* | ✓ | x | x |
| 2.3.116/ 2.3.1.9 | S7V863 | 276 | 3-ketoacyl-CoA thiolase | *Cyclobacterium gasimii* M12-11B | ✓ | ✓ | x |
| 2.8.3- | Q9RM86 | 0244 | 4-Hydroxybutyrate-CoA transferase | *Clostridium aminobutyricum* | ✓ | ✓ | ✓ |
| 2.8.3.1 | K3RRN6 | 0336 | Propionate CoA-transferase | *Escherichia coli* EC1865 | ✓ | ✓ | x |
| 2.8.3.10 | J1G510 | 0337 | Acetyl-CoA hydrolase/transferase | *Citrobacter* sp. A1 | ✓ | ✓ | ✓ |
| 2.8.3.11 | T1CV65 | 0338 | CoA-transferase family III | mine drainage metagenome | x | x | x |
| 2.8.3.12 | Q0AWW8 | 0339 | Glutaconate CoA-transferase | *Syntrophomonas wolfei* subsp. *wolfei* | x | x | x |
| 2.8.3.13 | Q7TNE1 | 0340 | Succinate--hydroxymethylglutarate CoA-transferase | *Mus musculus* (Mouse) | x | x | x |
| 2.8.3.16 | Q0K0H8 | 0342 | Formyl-CoA: oxalate CoA-transferase | *Cupriavidus necator* H16 | ✓ | x | x |
| 2.8.3.17 | Q93AM1 | 0343 | E-cinnamoyl-CoA: R-phenyilactate CoA transferase | *Clostridium sporogenes* | ✓ | x | x |
| 2.8.3.18 | B3EY95 | 0344 | Succinyl-CoA: acetate CoA-transferase | *Acetobacter aceti* | ✓ | ✓ | ✓ |
| 2.8.3.20 | A9WGE3 | 0345 | Succinyl-CoA--D-citramalate CoA-transferase | *Chloroflexus aurantiacus* | ✓ | ✓ | ✓ |
| 2.8.3.5 | P56006 | 0346 | Succinyl-CoA: 3-ketoacid coenzyme A transferase subunit A | *Helicobacter pylori* | ✓ | x | x |
| 2.8.3.6/-5/-8 | B8CRZ0 | 0347 | 3-oxoacid CoA-transferase | *Shewanella piezotolerans* | x | x | x |
| 2.8.3.9 | B2A667 | 0348 | Butyryl-CoA: acetate CoA transferase | *Natranaerobius thermophilus* | ✓ | x | x |

TABLE 4

| enzyme | YdiF (237) | | | | | | Protein 244 |
|---|---|---|---|---|---|---|---|
| substrate | propionate | butyrate | 3-butenoate | 4-pentenoate | 6-heptenoate | 2-hexenoate | 4-Hydroxybutyrate |
| thiol-product | ✓ | ✓ | ✓ | ✓ | ✓ | ✓ | ✓ |
| ketothiol-product | ✓ | ✓ | ✓ | ✓ | ✓ | ✓ | ✓ |

Additional Exemplary Embodiments

In one embodiment is provided a method of producing 3-oxopent-4-enoyl-CoA comprising enzymatically converting propenoate to 3-oxopent-4-enoyl-CoA using a polypeptide that has both CoA transferase and β-ketothiolase activities.

In one embodiment is provided a method of producing 3-keto-acyl-CoA esters, said method comprising the step of enzymatically condensing acetyl-CoA with any of an alkanoic acid, an alkenoic acid, a hydroxyacid or a haloacid using a polypeptide that has both CoA transferase and β-ketothiolase activities.

In one embodiment the alkanoic acid may be selected from straight chain alkanoic acids of carbon chain length n (n>2) such as acetate, propionate, butyrate, pentanoic acid, hexanoic acid and the like, or branched chain alkanoic acids such as isobutyrate, isovaleric acid or pivalic acid.

In one embodiment the alkenoic acid may be selected from straight chain alkenoic acids of carbon chain length n (wherein n>2) such as acrylic acid, 2-propenoic acid, 3-butenoic acid, 4-pentenoic acid, 5-hexenoic acid, 6-hepteneoic acid, crotonic acid, and the like, or branched chain alkenoic acids such as methacrylic acid, 3-methyl-3-butenoic acid, 4-methyl-4-pentenoic acid, and 5-methyl-5-hexenoic acid, and the like.

In one embodiment the hydroxyacid may be selected from hydroxyacids of carbon chain length n (wherein n>2) such as 3-hydroxypropionic acid, 4-hydroxybutyric acid, 5-hydroxyvaleric acid, and 6-hydroxy-caproic acid.

In one embodiment the haloacid may be selected from haloacids of carbon chain length n (wherein n>2) such as 3-halopropionic acid, 4-halobutyric acid, 5-halovaleric acid, and 6-halocaproic acid.

In one embodiment the method comprises the step of enzymatically condensing acetyl-CoA with the respective CoA ester of any of said alkanoic acid, said alkenoic acid, said hydroxyacid, or said haloacid using a polypeptide that has both CoA transferase and β-ketothiolase activities.

In one embodiment the 3-keto-acyl-CoA ester is converted to its respective free acid by a CoA transferase or a thioesterase.

In one embodiment the polypeptide that has both CoA transferase and β-ketothiolase activities is classified under EC 2.8.3.-.

In one embodiment the polypeptide that has both CoA transferase and β-ketothiolase activities is classified under EC 2.8.3.8.

In one embodiment the polypeptide that has both CoA transferase and β-ketothiolase activities is from *Salmonella enterica*, *Peptostreptococcaceae* bacterium, Firmicutes bacterium, *Megasphaera elsdenii*, *Salmonella enterica* subsp. *houtenaeserovar*, *Clostridium aminobutyricum*, or *Clostridium propionicum*.

In one embodiment the polypeptide that has both CoA transferase and β-ketothiolase activities has at least 95% sequence identity to the amino acid sequence set forth in any one of SEQ ID No: 1, 4, 5, 6, 7, 8, and 9.

In one embodiment the polypeptide that has both CoA transferase and β-ketothiolase activities has an amino acid substitution at one or more of positions 38, 60, 112, 258, and 390 of SEQ ID NO: 1.

In one embodiment the polypeptide that has both CoA transferase and β-ketothiolase activities is a CoA transferase whose amino acid sequence includes the motif I/V/A/LTE.

In one embodiment the polypeptide that has both CoA transferase and β-ketothiolase activities is a CoA transferase whose amino acid sequence includes the motifs EXGXXG and GXGG(A/F).

In one embodiment is provided a method of producing 3-oxopent-4-enoyl-CoA comprising: enzymatically converting propenoate to 3-oxopent-4-enoyl-CoA using a polypeptide that has both CoA transferase and β-ketothiolase activities; and enzymatically converting 3-oxopent-4-enoyl-CoA to 3-oxopent-4-enoate, for example using a CoA-transferase, for example a CoA-transferase classified under EC 2.8.3.6 or EC 2.8.3.8.

In one embodiment is provided a method of producing 3-oxopent-4-enoyl-CoA comprising: enzymatically converting propenoate to 3-oxopent-4-enoyl-CoA using a polypeptide that has both CoA transferase and β-ketothiolase activities; enzymatically converting 3-oxopent-4-enoyl-CoA to 3-oxopent-4-enoate; and enzymatically converting 3-oxopent-4-enoate to 3-buten-2-one, for example using a decarboxylase, for example a decarboxylase classified under EC 4.1.1.4.

In one embodiment is provided a method of producing 3-oxopent-4-enoyl-CoA comprising: enzymatically converting propenoate to 3-oxopent-4-enoyl-CoA using a polypeptide that has both CoA transferase and β-ketothiolase activities; enzymatically converting 3-oxopent-4-enoyl-CoA to 3-oxopent-4-enoate; enzymatically converting 3-oxopent-4-enoate to 3-buten-2-one; and enzymatically converting 3-buten-2-one to 3-buten-2-ol, for example using an alcohol dehydrogenase or a phenylacetaldehyde reductase. In one embodiment the alcohol dehydrogenase has at least 95% sequence identity to the amino acid sequence set forth in SEQ ID NO:16. In one embodiment the phenylacetaldehyde reductase has at least 95% sequence identity to the amino acid sequence set forth in SEQ ID NO:17.

In one embodiment is provided a method of producing 3-oxopent-4-enoyl-CoA comprising: enzymatically converting propenoate to 3-oxopent-4-enoyl-CoA using a polypeptide that has both CoA transferase and β-ketothiolase activities; enzymatically converting 3-oxopent-4-enoyl-CoA to 3-oxopent-4-enoate; enzymatically converting 3-oxopent-4-enoate to 3-buten-2-one; enzymatically converting 3-buten-2-one to 3-buten-2-ol; and enzymatically converting 3-buten-2-ol to 1,3 butadiene, for example using a linalool dehydratase, for example a linalool dehydratase classified under EC 4.2.1.127, or using a dehydratase classified under EC 4.2.1.-. In one embodiment the linalool dehydratase has at least 95% sequence identity to the amino acid sequence set forth in SEQ ID NO:18. In one embodiment the dehydratase has greater than 95% sequence identity to the 5-aminovaleryl-CoA dehydratase from *C. viride* or to a dehydratase classified under EC 4.2.1.- from species such as *Aquincola tertiaricarbonis* or *Methylibium petroleiphilum* PM1.

In one embodiment is provided a method of producing 3-oxo-acyl-CoA compounds of formula (IIa), said method comprising enzymatically converting a carboxylic acid of formula (Ia) to a 3-oxo-acyl-CoA compound of formula (IIa)

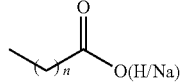

Formula (Ia)

-continued

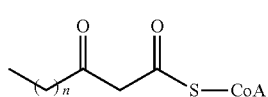

Formula (IIa)

using a polypeptide that has both CoA transferase and β-ketothiolase activities.

In one embodiment is provided a method of producing 3-oxo-enoyl-CoA compounds of formula (IIb), said method comprising enzymatically converting an unsaturated carboxylic acid of formula (Ib) to a 3-oxo-enoyl-CoA compound of formula (IIb):

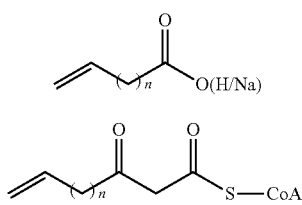

Formula (Ib)

Formula (IIb)

using a polypeptide that has both CoA transferase and β-ketothiolase activities.

In one embodiment is provided a method of producing 3-oxo-hydroxyacyl-CoA compounds of formula (IIc), said method comprising enzymatically converting a hydroxyl-substituted carboxylic acid of formula (Ic) to a 3-oxo-hydroxyacyl-CoA compound of formula (IIc):

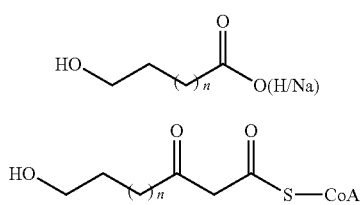

Formula (Ic)

Formula (IIc)

using a polypeptide that has both CoA transferase and β-ketothiolase activities. In one embodiment the 3-oxo-hydroxyacyl-CoA compound of formula (IIc) is converted to a nylon compound.

In one embodiment 4-hydroxybutyric acid, or a salt thereof, is enzymatically converted to 3-oxo-6-hydroxyhexanoyl-CoA using a polypeptide that has both CoA transferase and β-ketothiolase activities. In one embodiment 3-oxo-6-hydroxyhexanoyl-CoA is enzymatically converted to 6-hydroxyhexanoic acid, and 6-hydroxyhexanoic acid is enzymatically converted to one or more of adipic acid, 6-aminohexanoic acid, hexamethylenediamine, caprolactam, and 1,6-hexanediol using one or more isolated enzymes selected from dehydrogenases, reductases, hydratases, thioesterases, monooxygenases, and transaminases.

In one embodiment 3-hydroxypropionic acid, or a salt thereof, is enzymatically converted to 3-oxo-5-hydroxypentanoyl-CoA using a polypeptide that has both CoA transferase and β-ketothiolase activities.

In one embodiment 5-hydroxypentanoic acid, or a salt thereof, is enzymatically converted to 3-oxo-7-hydroxyheptanoyl-CoA using a polypeptide that has both CoA transferase and β-ketothiolase activities.

In one embodiment is provided a method as described above wherein said method is performed in a non-naturally occurring host, for example a recombinant host.

In one embodiment is provided a non-naturally occurring host capable of producing 3-oxopent-4-enoyl-CoA, said host comprising at least one exogenous nucleic acid encoding a polypeptide having both CoA transferase and β-ketothiolase activities.

In one embodiment is provided a non-naturally occurring host capable of producing 1,3-butadiene, said host comprising at least one exogenous nucleic acid encoding a polypeptide having both CoA transferase and β-ketothiolase activities.

In one embodiment is provided a non-naturally occurring host capable of producing 3-oxo-acyl-CoA compounds of formula (IIa), said host comprising at least one exogenous nucleic acid encoding a polypeptide having both CoA transferase and 3-ketothiolase activities.

In one embodiment is provided a non-naturally occurring host capable of producing 3-oxo-enoyl-CoA compounds of formula (IIb), said host comprising at least one exogenous nucleic acid encoding a polypeptide having both CoA transferase and β-ketothiolase activities.

In one embodiment is provided a non-naturally occurring host capable of producing 3-oxo-hydroxyacyl-CoA compounds of formula (IIc), said host comprising at least one exogenous nucleic acid encoding a polypeptide having both CoA transferase and β-ketothiolase activities.

In one embodiment is provided a non-naturally occurring host capable of producing nylon compounds, said host comprising at least one exogenous nucleic acid encoding a polypeptide having both CoA transferase and β-ketothiolase activities.

In one embodiment the host is cultured under aerobic, anaerobic, or micro-aerobic cultivation conditions.

In one embodiment the host is cultured under conditions of nutrient limitation.

In one embodiment the host is retained using a ceramic hollow fiber membrane.

In one embodiment the principal carbon source derives from a biological feedstock, for example a biological feedstock such as, or deriving from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste.

In one embodiment the principal carbon source derives from a non-biological feedstock, for example a non-biological feedstock such as, or deriving from, natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

In one embodiment the host is a prokaryotic host, for example from the genus *Escherichia, Clostridia, Corynebacteria, Cupriavidus, Pseudomonas, Delftia, Bacillus, Lactobacillus, Lactococcus,* or *Rhodococcus*. In one embodiment the host is *Escherichia coli, Clostridium ljungdahlii, Clostridium autoethanogenum, Clostridium kluyveri, Corynebacterium glutamicum, Cupriavidus necator, Cupriavidus metallidurans, Pseudomonas fluorescens, Pseudomonas putida, Pseudomonas oleavorans, Delftia acidovorans, Bacillus subtillis, Lactobacillus delbrueckii, Lactococcus lactis,* or *Rhodococcus equi*.

In one embodiment the host is a eukaryotic host, for example from the genus *Aspergillus, Saccharomyces, Pichia, Yarrowia, Issatchenkia, Debaryomyces, Arxula,* or *Kluyveromyces*. In one embodiment the host is *Aspergillus niger, Saccharomyces cerevisiae, Pichia pastoris, Yarrowia lipolytica, Issathenkia orientalis, Debaryomyces hansenii, Arxula adenoinivorans,* or *Kluyveromyces lactis*.

In one embodiment the host is capable of producing 1,3-butadiene and comprises an exogenous alcohol dehydrogenase or an exogenous phenylacetaldehyde reductase, and an exogenous linalool dehydratase. In one embodiment the alcohol dehydrogenase has at least 95% sequence identity to the amino acid sequence set forth in SEQ ID NO:16. In one embodiment the phenylacetaldehyde reductase has at least 95% sequence identity to the amino acid sequence set forth in SEQ ID NO:17. In one embodiment the linalool dehydratase has at least 95% sequence identity to the amino acid sequence set forth in SEQ ID NO:18.

In one embodiment is provided a composition comprising 3-oxopent-4-enoyl-CoA synthesized by a method described above.

In one embodiment is provided a composition comprising butadiene synthesized by a method described above.

In one embodiment is provided method for producing bio-derived 3-oxopent-4-enoyl-CoA, comprising culturing or growing a host described above under conditions and for a sufficient period of time to produce bio-derived 3-oxopent-4-enoyl-CoA.

In one embodiment is provided a method for producing bio-derived butadiene, comprising culturing or growing a host described above under conditions and for a sufficient period of time to produce bio-derived butadiene.

In one embodiment is provided a variant polypeptide having at least 95% sequence identity to the amino acid sequence of a wild-type enzyme set forth in any of SEQ NOs: 1, 5, 6, 7, 8, and 9, and comprising at least one mutation to the wild-type enzyme. In one embodiment the at least one mutation results in an increase in the transferase activity, the β-ketothiolase activity, or both activities of the wild-type enzyme.

In one embodiment the at least one mutation results in a decrease in or a loss of the transferase activity or the β-ketothiolase activity of the wild-type enzyme. In one embodiment the mutation is a deletion of at least one amino acid. In one embodiment the mutation is an addition of at least one amino acid. In one embodiment the mutation is a substitution of at least one amino acid, for example a conservative substitution.

In one embodiment is provided a variant polypeptide having the amino acid sequence set forth in SEQ ID NO:1 with an amino acid other than a serine at position 38, an amino acid other than a serine at position 60, an amino acid other than a cysteine at position 112, an amino acid other than a cysteine at position 258, or an amino acid other than a cysteine at position 390. In one embodiment the variant polypeptide comprises an alanine at position 38, an alanine at position 60, an alanine at position 112, or an alanine at position 390 of SEQ ID NO: 1.

In one embodiment is provided a variant polypeptide having the amino acid sequence set forth in SEQ ID NO:1 with an amino acid other than glutamic acid at position 324. In one embodiment the variant polypeptide comprises a leucine at position 324. In one embodiment the variant polypeptide comprises a glycine at position 324.

In one embodiment is provided a variant polypeptide having an amino acid sequence comprising the motifs I/V/A/LTE, EXGXXG, and GXGG(A/F).

In one embodiment the at least one mutation results in the presence of an XXGXXG motif where an EXGXXG motif was present in the wild-type enzyme.

In one embodiment the at least one mutation does not affect the β-ketothiolase activity of the wild-type enzyme.

In one embodiment is provided a bio-derived, bio-based, or fermentation-derived product comprising: (a) a composition comprising at least one bio-derived, bio-based, or fermentation-derived compound prepared (i) using a host described herein, (ii) using a variant polypeptide described herein, or (iii) according to a method described herein, or any combination thereof; (b) a bio-derived, bio-based, or fermentation-derived polymer or resin, for example styrene-butadiene-rubber, poly-butadiene, styrene-butadiene latex, acrylonitrile-butadiene-styrene resin, nitrile rubber, adiponitrile, or nylon compounds, comprising the bio-derived, bio-based, or fermentation-derived composition or compound of (a), or any combination thereof; (c) a molded substance obtained by molding the bio-derived, bio-based, or fermentation-derived polymer or resin of (b), or any combination thereof; (d) a bio-derived, bio-based, or fermentation-derived formulation comprising the bio-derived, bio-based, or fermentation-derived composition or compound of (a), bio-derived, bio-based, or fermentation-derived polymer or resin of (b), or bio-derived, bio-based, or fermentation-derived molded substance of (c), or any combination thereof, or (e) a bio-derived, bio-based, or fermentation-derived semi-solid or a non-semi-solid stream, comprising the bio-derived, bio-based, or fermentation-derived composition or compound of (a), bio-derived, bio-based, or fermentation-derived polymer or resin of (b), bio-derived, bio-based, or fermentation-derived formulation of (d), or bio-derived, bio-based, or fermentation-derived molded substance of (c), or any combination thereof.

In one embodiment is provided a method of producing 3-oxopent-4-enoyl-CoA, said method comprising: providing propenoate; and providing a means for enzymatically converting propenoate to 3-oxopent-4-enoyl-CoA, wherein the means comprises both CoA transferase and β-ketothiolase activities.

In one embodiment is provided a method of producing butadiene, said method comprising: (a) providing propenoate; (b) providing a means for enzymatically converting propenoate to 3-oxopent-4-enoyl-CoA, wherein the means comprises both CoA transferase and β-ketothiolase activities; (c) enzymatically converting 3-oxopent-4-enoyl-CoA to 3-oxopent-4-enoate using a CoA-transferase; (d) enzymatically converting 3-oxopent-4-enoate to 3-buten-2-one using a decarboxylase; (e) enzymatically converting 3-buten-2-one to 3-buten-2-ol using an alcohol dehydrogenase or a phenylacetaldehyde reductase; and (f) enzymatically converting 3-buten-2-ol to 1,3 butadiene using a linalool dehydratase.

In one embodiment is provided a non-naturally occurring host capable of producing butadiene, said host comprising: (a) a means for enzymatically converting propenoate to 3-oxopent-4-enoyl-CoA, wherein the means comprises both CoA transferase and β-ketothiolase activities; (b) at least one exogenous nucleic acid encoding a CoA-transferase; (c) at least one exogenous nucleic acid encoding a decarboxylase; (d) at least one exogenous nucleic acid encoding an alcohol dehydrogenase or a phenylacetaldehyde reductase; and (e) at least one exogenous nucleic acid encoding a linalool dehydratase.

In one embodiment is provided a non-naturally occurring host capable of producing 3-oxo-acyl-CoA compounds of formula (IIa), said host comprising: (a) a carboxylic acid of formula (Ia), or a salt form thereof; and (b) a means for enzymatically converting the carboxylic acid of formula (Ia) to a 3-oxo-acyl-CoA compound of formula (IIa), wherein the means comprises both CoA transferase and β-ketothiolase activities.

In one embodiment is provided a non-naturally occurring host capable of producing 3-oxo-enoyl-CoA compounds of formula (IIb), said host comprising: (a) an unsaturated carboxylic acid of formula (Ib), or a salt form thereof; and (b) a means for enzymatically converting the unsaturated carboxylic acid of formula (Ib) to a 3-oxo-enoyl-CoA compound of formula (IIb), wherein the means comprises both CoA transferase and β-ketothiolase activities.

In one embodiment is provided a non-naturally occurring host capable of producing 3-oxo-hydroxyacyl-CoA compounds of formula (IIc), said host comprising: (a) a hydroxy-substituted carboxylic acid of formula (Ic), or a salt form thereof; and (b) a means for enzymatically converting the hydroxy-substituted carboxylic acid of formula (Ic) to a 3-oxo-hydroxyacyl-CoA compound of formula (IIc), wherein the means comprises both CoA transferase and β-ketothiolase activities.

In one embodiment is provided a polypeptide-substrate complex comprising: (a) a polypeptide having at least 95% sequence identity to the amino acid sequence set forth in any one of SEQ ID No: 1, 3, 4, 5, 6, 7, 8, and 9; and (b) an acyl-CoA compound; wherein said polypeptide has β-ketothiolase activity but no CoA-transferase activity.

In one embodiment is provided a polypeptide-substrate complex comprising: (a) a polypeptide having the amino acid sequence set forth in any one of SEQ ID No: 3 and 4; and (b) an acyl-CoA compound; wherein said polypeptide has 3-ketothiolase activity but no CoA-transferase activity.

In one embodiment is provided a polypeptide-substrate complex comprising: (a) a polypeptide having the amino acid sequence set forth in any one of SEQ ID No: 3 and 4; and (b) an acyl-CoA compound; wherein said polypeptide has 3-ketothiolase activity but reduced CoA-transferase activity compared to a polypeptide having the amino acid sequence set forth in any one of SEQ ID No: 1, 5, 6, 7, 8, and 9.

In one embodiment is provided a polypeptide having β-ketothiolase activity, wherein said polypeptide does not comprise a ser-his-his and does not comprise a cys-his-cys triad. In one embodiment the polypeptide also has CoA-transferase activity. In one embodiment the polypeptide has β-ketothiolase activity but no CoA-transferase activity.

In one embodiment is provided a polypeptide having at least 95% sequence identity to the amino acid sequence set forth in any one of SEQ ID No: 1, 5, 6, 7, 8, and 9, wherein the amino acid sequence of said polypeptide includes the motif I/V/A/LTE. In one embodiment the amino acid sequence of said polypeptide includes at least one of the motifs EXGXXG and GXGG(A/F). In one embodiment the amino acid sequence of said polypeptide includes both of the motifs EXGXXG and GXGG(A/F).

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of producing 3-keto-acyl-CoA esters, said method comprising the step of enzymatically condensing acetyl-CoA with a hydroxyacid using a polypeptide that has both CoA transferase and β-ketothiolase activities, wherein said polypeptide has at least 90% sequence identity to the amino acid sequence set forth in any one of SEQ ID No: 1, 4, 5, 6, 7, 8, and 9.

2. The method of claim 1, wherein said hydroxyacid has a carbon chain length n (wherein n>2) and is selected from the group consisting of 3-hydroxypropionic acid, 4-hydroxybutyric acid, 5-hydroxyvaleric acid, and 6-hydroxycaproic acid.

3. The method of claim 1, wherein the 3-keto-acyl-CoA ester is converted to its respective free acid by a CoA transferase.

4. The method of claim 1, wherein said polypeptide is classified under EC 2.8.3.-.

5. The method of claim 1, wherein said polypeptide is from *Salmonella enterica*, *Peptostreptococcaceae* bacterium, Firmicutes bacterium, *Megasphaera elsdenii*, *Salmonella enterica* subsp. *houtenaeserovar*, *Clostridium aminobutyricum*, or *Clostridium propionicum*.

6. The method of claim 1, wherein said polypeptide has at least 95% sequence identity to the amino acid sequence set forth in any one of SEQ ID No: 1, 4, 5, 6, 7, 8, and 9 and exhibits both CoA transferase and β-ketothiolase activities.

7. The method of claim 1, wherein said polypeptide has an amino acid substitution at at least one of position 38, 60, 112, 258, and 390 of SEQ ID NO: 1.

8. A method of producing 3-oxo-hydroxyacyl-CoA compounds of formula (IIc), said method comprising enzymatically converting a hydroxyl-substituted carboxylic acid of formula (Ic) to a 3-oxo-hydroxyacyl-CoA compound of formula (IIc):

Formula (Ic)

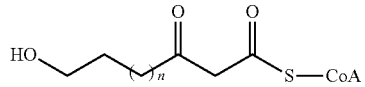

Formula (IIc)

using a polypeptide that has both CoA transferase and β-ketothiolase activities, wherein said polypeptide has at least 90% sequence identity to the amino acid sequence set forth in any one of SEQ ID No: 1, 4, 5, 6, 7, 8, and 9 and exhibits both CoA transferase and β-ketothiolase activities.

* * * * *